United States Patent
Shah et al.

(10) Patent No.: US 11,793,789 B2
(45) Date of Patent: *Oct. 24, 2023

(54) TREATMENT OF OPHTHALMOLOGICAL CONDITIONS USING BUFFER-FREE OPHTHALMOLOGICAL COMPOSITIONS OF KETOROLAC AND PHENYLEPHRINE

(71) Applicant: Somerset Therapeutics, LLC, Hollywood, FL (US)

(72) Inventors: Mandar V. Shah, Rockaway, NJ (US); Kumaresan Parthasarathi, Dayton, NJ (US); Ilango Subramanian, Warren, NJ (US); Veerappan Subramanian, Warren, NJ (US); Aman Trehan, Hillsborough, NJ (US)

(73) Assignee: Somerset Therapeutics, LLC, Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/871,924

(22) Filed: Jul. 23, 2022

(65) Prior Publication Data
US 2023/0044398 A1 Feb. 9, 2023

Related U.S. Application Data

(60) Provisional application No. 63/225,321, filed on Jul. 23, 2021.

(51) Int. Cl.
| | |
|---|---|
| *A61K 31/407* | (2006.01) |
| *A61K 9/00* | (2006.01) |
| *A61K 31/137* | (2006.01) |
| *A61K 47/02* | (2006.01) |

(52) U.S. Cl.
CPC .......... *A61K 31/407* (2013.01); *A61K 9/0048* (2013.01); *A61K 31/137* (2013.01); *A61K 47/02* (2013.01)

(58) Field of Classification Search
CPC ... A61K 31/137; A61K 31/407; A61K 9/0048
See application file for complete search history.

(56) References Cited

U.S. PATENT DOCUMENTS

| | | |
|---|---|---|
| 4,550,022 A | 10/1985 | Garabedian et al. |
| 8,173,707 B2 | 5/2012 | Demopulos et al. |
| 8,586,633 B2 | 11/2013 | Demopulos et al. |
| 9,066,856 B2 | 6/2015 | Demopulos et al. |
| 9,278,101 B2 | 3/2016 | Demopulos et al. |
| 9,399,040 B2 | 7/2016 | Demopulos et al. |
| 9,486,406 B2 | 11/2016 | Demopulos et al. |
| 9,855,246 B2 | 1/2018 | Demopulos et al. |
| 2008/0050335 A1 | 2/2008 | Faour et al. |
| 2018/0147214 A1 | 5/2018 | Ostrow et al. |

FOREIGN PATENT DOCUMENTS

| | | |
|---|---|---|
| WO | 199408602 | 4/1994 |
| WO | 199516435 | 6/1995 |

OTHER PUBLICATIONS

Gonzalez-Salinas et al., "Patient considerations in cataract surgery—the role of combined therapy using phenylephrine and ketorolac", Patient Preference and Adherence, vol. 10, pp. 1795-1801 (2016).*
Malhotra et al., "Effect of preservative, antioxidant and viscolizing agents in vitro transcorneal permeation of ketorolac tromethamine", Indian Journal of Experiment Biology, vol. 40, No. 5, pp. 555-559 (2002).*
Omeros Corporation, Omidria® Product Label, Revised Dec. 2017.

* cited by examiner

*Primary Examiner* — Kevin E Weddington
(74) *Attorney, Agent, or Firm* — Transformative Legal, LLC; Len S. Smith; Denise M. Brown

(57) ABSTRACT

This invention provides novel compositions comprising an anti-inflammatory agent and a mydriatic agent suitable for intraocular use, particularly ketorolac or pharmaceutically salts thereof and phenylephrine or pharmaceutically salts thereof, which are free of any buffering agent and yet, surprisingly, maintain stability for significant periods of time (e.g., at least about 3 months). The present invention also relates to a process of preparing such compositions and use thereof, e.g., in combination with intraocular ophthalmologic irrigation solutions.

11 Claims, No Drawings

TREATMENT OF OPHTHALMOLOGICAL CONDITIONS USING BUFFER-FREE OPHTHALMOLOGICAL COMPOSITIONS OF KETOROLAC AND PHENYLEPHRINE

RELATED APPLICATIONS/PRIORITY

This patent application claims priority to U.S. Provisional Patent Application No. 63/225,321 filed Jul. 23, 2021, entitled "BUFFER-FREE, STABLE OPHTHALMOLOGICAL COMPOSITIONS OF KETOROLAC AND PHENYLEPHRINE AND APPLICATIONS THEREOF". This application claims the benefit of priority to, and incorporates by reference the entirety of, this above-referenced priority application.

FIELD OF THE INVENTION

The invention primarily relates to ophthalmological compositions comprising ketorolac compounds and phenylephrine compounds, methods of preparing such compositions, and methods of their use.

BACKGROUND OF THE INVENTION

People place a remarkably high value on vision and eye health. As such, considerable time and resources are spent on ophthalmic product research and development.

Ocular tissue is one of the most complex and sensitive tissues in the human body, with the pH being a crucial property. Under normal conditions, healthy human ocular tissue maintains a pH of approximately 7.0-7.3. See, e.g., Coles, in "Coles W H, Jaros P A. Dynamics of ocular surface pH." Br J Ophthalmol. 1984 August; 68(8):549-52 (finding, e.g., the mean pH within a large-scale study of eye physiology to be 7.11).

Several conditions and diseases can negatively affect eye health. Exemplary disorders of the anterior portion of the eye include cataracts, glaucoma, lens damage, infection, and inflammation. Disorders of the eye can lead to the need for ocular surgical procedures such as, e.g., cataract or lens replacement surgery.

In both treatment of eye conditions and as an adjunct to surgical procedures, topical ophthalmological formulations are often administered. Ophthalmological products directed to controlling intraocular pressure levels, such as, e.g., products comprising beta adrenergic receptor antagonists and alpha-2 adrenergic receptor agonists, have been developed and are widely employed in the treatment of eye disorders such as, e.g., glaucoma. The efficacy of many ophthalmological topical applications, such as, for example, those attempting to treat eye conditions (e.g., conjunctivitis (inflammation of the conjunctiva) or other external ocular infections), often hinges on their ability to maintain contact with the afflicted eye anatomy or their ability to be retained by the eye, e.g., to permeate and be held within, cells of the cornea.

It is crucial during any such ophthalmological treatments to maintain suitable ocular pH to avoid further damaging or introducing new damage to the eye. Moreover, achieving a stable formulation is critical to facilitate shelf-life and longer-term use; and pH plays a key role in product stability. For example, Peyman, Journal of ophthalmic & vision research vol. 6,1 (2011): 36-46 in discussing the difficulty of reaching a stable formulation within a predetermined pH range, states, "The neutrality of pH for medical formulations while desirable, is a hard target to achieve for many compounds. Many formulations become unstable and suffer from lack of (partial) solubility if pushed toward a fixed pH." Using an active pharmaceutical ingredient (API) at an improper pH can negatively impact an APIs stability in a formulation. See id.

Despite such disclosures, some ophthalmological formulations have pH values lower than neutral (e.g., lower than ocular pH). See, for example, De Villiers, Melgardt, (2009), Chapter 18, "Buffers and pH Adjusting Agents," in A Practical Guide to Contemporary Pharmacy Practice (pp. 224-230), Edition 3. Lippincott Williams & Wilkins and edited by Judith E. Thompson, and, e.g., the page "Ophthalmic Preparations" published on the Web at the UNC Eshelman School of Pharmacy Web site, subsection "Buffers and Buffer Capacity." See also, U.S. Pat. Nos. 9,066,856, 9,486,406, and 9,855,246, discussed further below, wherein such formulations, while having a lower than neutral pH and comprise buffer systems designed to maintain such a lower pH. US Patent Publication Number 2018/0147214 also discloses a low pH ocular formulation, allegedly suitable for a range of active ingredients (including, e.g., a combination of ketorolac and phenylephrine), wherein the pH of the formulation is preferably 4.0 or below, and which further utilizes deuterated water to aid in product stability.

Such conflicting information concerning the initial pH of ophthalmic formulations may be due to the fact such formulations are highly active pharmaceutical ingredient ("API")-dependent and are further highly influenced by the nature and amount of other formulation components (e.g., excipients, carriers, and the like).

To aid in controlling pH in ocular tissues during administration of medicines and, further, to facilitate sufficient product stability, buffering agents have been nearly universally incorporated in ophthalmologic solutions (see, e.g., Mortan Inc., "Ocular irrigation fact sheet #4 Buffer Solutions in Ocular Irrigation", The Morgan Lens, not dated ("n.d.")) (the "goal of eye irrigation is to quickly return the pH to normal (about 7.1). Until the pH returns to normal, damage to the eye may continue"). Given the importance of buffers in controlling the pH of ocular tissues, numerous buffered ophthalmological formulations are known in the art. For example, U.S. Pat. No. 5,523,316 discloses a system and method for the modification of conventional aqueous irrigation solutions, including buffering agents, by the addition of therapeutic agents to control intraocular pressure. U.S. Pat. No. 5,811,446 discloses a system and method for a topical ophthalmologic solution of histidine, which includes a buffering component and at least one other active agent such as anti-glaucoma agent, e.g., timolol, phenylephrine, a steroid, or an NSAID, for inflammation associated with ophthalmologic procedures. U.S. Pat. No. 5,624,893 similarly discloses buffered compositions for treating or preventing corneal haze associated with laser irradiation and photoablation. Additionally, PCT Publication Nos. WO 94/08602 & WO 95/16435 disclose a system and method for inclusion of a mydriatic agent such as epinephrine in ocular irrigation solution(s) as well as non-steroidal anti-inflammatory drugs within ophthalmologic irrigation solutions. Such formulations further contain a buffer.

Indeed, even some ophthalmological formulations have included multiple buffer components providing even more complex buffering systems in attempts to address the hypersensitivity of the eye and yet deliver beneficial actives to address ophthalmic conditions. See, e.g., U.S. Pat. No. 4,550,022. Although concerns about high concentrations of buffers have been raised (See, e.g., Schuerer, Nadine "Implications for Ophthalmic Formulations: Ocular Buffers Show Varied Cytotoxic Impact on Human Corneal—Limbal and Human Conjunctival Epithelial Cells", Cornea: June 2017—Volume 36—Issue 6—p 712-718), the overwhelming majority of proposed and on-market products for treating conditions of the eye have used and, indeed, continue to use, buffers as a key component of such formulations. An example of recent disclosures relating to buffered ophthalmological formulations is provided by, e.g., U.S. Pat. No. 10,675,294 B2; U.S. Patent Publication No. 2018/0085349; IN 201818046475; and WO 2020231670A1.

Buffered ophthalmological formulations have been employed in the delivery of a wide variety of APIs. Active ingredients/APIs in such formulations can have, for example, antimicrobial, pain relief, anti-inflammatory, and mydriatic properties. However, although use of buffers is common in ophthalmological products, each individual API, combination of APIs, or formulation used in the treatment of ophthalmological conditions, is unique. Even closely related APIs can exhibit markedly different properties in the eye; and, accordingly, exhibit unexpected effects. Thus, each formulation requires careful and specific consideration in its development. Ophthalmological products comprising prostaglandins or prostaglandin analogues are an excellent example of such complexities. Prostaglandin analogs ("prostaglandins"), represent a group of structurally similar APIs, many of which having utility in the eye. However, despite such structural similarity and overall shared biological activity(ies), not all prostaglandins work alike. Research data points to the existence of a unique receptor for bimatoprost (a single prostaglandin API), which is distinct from the known receptor for structurally similar prostaglandins (e.g., the prostaglandin latanoprost), and bimatoprost can reduce intraocular pressure of patients unresponsive to at least one structurally similar prostaglandin, latanoprost.

Further, as already noted, developing effective formulations of ophthalmological products can be challenging, and changes to a single ingredient in ophthalmic formulations comprising even the same API can have significant effects on the pharmaceutical properties of such a formulation. LUMIGAN® 0.01%, a bimatoprost ophthalmic solution marketed at the time of this disclosure by Allergan, an AbbVie company, comprises one third of the amount of active ingredient bimatoprost as LUMIGAN® 0.03% (a bimatoprost ophthalmic solution also marketed at the time of this disclosure by Allergan) yet surprisingly demonstrates efficacy similar to LUMIGAN® 0.03%, presumably due to the four-fold increase in a single excipient in the formulation (benzalkonium chloride).

Combination therapies and combination products used in the eye present still other or additional unique challenges with respect to developing ophthalmological products. In certain cases, for example, the combination of two ophthalmological ingredients demonstrated to be effective when used individually results in unexpected adverse events or other negative effects. For example, combinations of eye medications containing latanoprost and thimerosal have been shown to lead to adverse events including blurred vision, burning of the eye, etc. Similarly, Mydriatic-3, a therapeutic containing phenylephrine, exhibits seven "major" interactions with other APIs (i.e., clinically significant, and high-risk interactions). As such, successful combination products must often be considered separately from single active ingredient products.

One successful FDA-approved ophthalmological product comprising a combination of active ingredients is OMIDRIA®, a prescription therapeutic developed by Omeros Corporation, which first received FDA approval on May 30, 2014 under NDA number 205388. OMIDRIA specifically comprises an effective combination of two markedly different APIs, ketorolac tromethamine and phenylephrine hydrochloride ("HCl" or "HCL"). Ketorolac is a nonsteroidal anti-inflammatory drug (NSAID), which works by blocking the body's production of certain natural substances that cause inflammation resulting in a decrease in pain from swelling for the patient. Phenylephrine HCL is an al-adrenergic receptor agonist exhibiting mydriatic properties (causing dilation of the pupil). OMIDRIA is formulated as a solution for addition to an irrigation solution. OMIDRIA further includes sodium citrate dihydrate and citric acid monohydrate (respectively, a buffer and chelating agent(s) designed to maintain the formulation at a pH of 6.3), and water for injection, and may include sodium hydroxide and hydrochloric acid for pH adjustment. OMIDRIA is indicated for controlled mydriasis in the pupil during cataract surgery, causing a statistically significant reduction in pain in 10-12 hours. Disclosures relating to OMIDRIA® as well as other related compositions and methods/principles are provided in, e.g., U.S. Pat. Nos. 8,173,707; 8,586,633; 9,066,856; 9,278,101; 9,399,040; 9,486,406; and 9,855,246. Each of these disclosures teach the use of buffered formulations of ketorolac and phenylephrine compounds.

Various additional disclosures have proposed related compositions and uses including the combination of ketorolac and phenylephrine. For example, U.S. Pat. Nos. 9,066,856, 9,486,406, and 9,855,246 (each belonging to the same patent family) disclose preservative-free and antioxidant-free liquid pharmaceutical formulations of ketorolac and phenylephrine for application as intraocular ophthalmologic irrigation solutions, utilizing a buffer system such as a sodium phosphate buffer system or an even more preferred sodium citrate buffer system to maintain an extended period of product stability (out to, e.g., about 24 months). US Pat. Pub. No. 2008/0050335 also discloses a buffered, high-viscosity formulation optionally comprising both ketorolac and phenylephrine.

In view of the above and other general challenges familiar to the art with regard to the development of pharmaceutically acceptable and ophthalmologically suitable products (e.g., safety/toxicity, efficacy, drug interaction(s), etc.), developing ophthalmologically effective formulations remains a significant challenge given the complexity and sensitivity of the eye. See, e.g., Agrahari et al "A comprehensive insight on ocular pharmacokinetics," Drug delivery and translational research Journal vol. 6,6 (2016): 735-754) ("Ocular tissue barriers pose major challenges in delivering drugs at therapeutic concentrations to the desired location"). In fact, each formulation must be specifically formulated to its intended use and API(s).

Construction, Terms, and Acronyms

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects, as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure." The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact. The occasional separate description of an element as ophthalmologically suitable or pharmaceutically acceptable, etc., is not intended to be limiting. Compositions and ingredients herein, uncontradicted, can be characterized in both ways.

Uncontradicted, heading(s) (e.g., "Construction, Terms . . . ") and subheadings are included for convenience and do not limit the scope of any aspect(s). Uncontradicted, aspect(s), step(s), or element(s) described under one heading apply to other aspect(s) provided elsewhere.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "—," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01) (e.g., common tests used in such contexts in the art (e.g., for efficacy by clinical study)). "Detectable" means measurably present/different using known/described detection tools/techniques. "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~-50%, ≥~-51%, ≥~-66%, ≥~-75%, ≥~-90%, ≥~-95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure. Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably ≥50% (e.g., mostly comprises, predominately includes, etc., mean ≥50%) (e.g., a system that mostly includes element X is composed of ≥50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤~25% of an element and terms such as "substantially free" of an element mean comprising ≤~5% of an element. The term "substantially" in other context (e.g., when used in connection with tests or comparisons or as used in a phrase such as "substantially identical" or "substantially similar") typically is recognized as meaning not differing in any material way from the referenced element(s)/comparison (e.g., having essentially the same elements, amounts, and conditions in all material respects, except for any indicated differences, such as an explicitly referenced test condition, element, or agent).

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

Additional Terms, Concepts, and Acronyms

Uncontradicted, any description of weight is weight/volume percent ("wt/v. %").

Except where explicitly indicated or clearly indicated by context, "improved" herein means "increased" with respect to any parameter, condition, amount, etc., associated with better outcomes (e.g., greater stability, efficacy, etc.) and "reduced," with respect to any negative properties, characteristics, etc., such as with respect to the toxicity of a composition. Uncontradicted, terms such as "enhanced," "improved," and the like are used synonymously. Any enhancement/improvement is to be understood as meaning a DOS improvement.

"Pharmaceutical suitability", "pharmaceutically suitable", "ophthalmologically suitable" or "ophthalmological suitability" are phrases typically used to refer to compositions that are safe and effective for pharmaceutical administration and application, having sufficient potency, purity, strength, quality, and safety for pharmaceutical application, in cases specifically to the eye, as may be judged by regulatory authority review, and as established by, e.g., one or more well controlled and adequate clinical studies performed in compliance with generally prevailing regulatory authority standards. Compositions described as "ophthalmologically suitable" should be interpreted to mean suitable for ophthalmic delivery when provided in a potency, purity, strength, or quality making it safe for ophthalmic use. Components described as "ophthalmologically suitable" should be interpreted in a similar manner Uncontradicted, a description of "suitability" implicitly means that the referenced element, step, etc., is ophthalmologically/pharmaceutically suitable or otherwise medically suitable (e.g., safe and effective as determined by proper nonclinical/clinical testing).

A "therapeutically effective amount" typically means an amount of a compound or pharmaceutical composition that will elicit an intended (typically significant) biological or medical response of a tissue, system, animal, or human that is being sought by the researcher, medical doctor, or other clinician. In aspects, a therapeutically effective amount is demonstrated by at least one or at least two well controlled and adequate clinical studies in human subjects/patients (e.g., as would be considered sufficient for pharmaceutical approval). Uncontradicted, APIs in compositions disclosed herein are present in such amounts.

Excipients herein also are typically present in "effective amounts," and uncontradicted, any described class of excipient or specific excipient is understood to be present in the associated composition/formulation in an effective amount, which generally means, in this context, an amount that is effective for the described function(s) associated with the excipient (it being understood that some excipient compound(s)/ingredient(s) exhibit more than one effect). E.g., a tonicity agent will be understood to be present in a composition/formulation in an amount that is effective to impart an indicated tonicity effect, a tonicity effect that is required for suitability of the composition, or an effect that imparts a significant tonicity effect on a composition (with respect to a comparator composition lacking the compound(s)/ingredient(s)).

The terms "core composition", "carrier composition", and "combined composition" are used herein to describe compositions comprising differing components provided by the invention. "Core composition" means a composition consisting of pharmaceutically acceptable and ophthalmologically suitable ketorolac compound(s) and phenylephrine compound(s), and optionally any additional excipient(s) (e.g., antioxidant(s) or, e.g., chelating agent(s), etc.) or active pharmaceutical ingredient(s) (APIs), but lacking a carrier which makes the composition a liquid composition (that is, a core composition is a composition in solid form (e.g., a dry powder)). "Carrier composition" means a composition comprising a core composition plus a liquid carrier (e.g., water). "Combined composition" means a composition comprising a core composition or carrier composition combined with additional ophthalmologically suitable components, compositions, or solutions, the one or more additional components, compositions, or solutions capable of being used alone or in combination with other products not provided by the invention in ophthalmological applications. An ophthalmologically suitable irrigation solution is one example of such an additional component that can be combined with a core composition or a carrier composition to form a combined composition.

Uncontradicted, any use of the term "composition(s)" herein lacking any further qualifying nomenclature (such as, e.g., "core", "carrier", or "combined") applying to the term, means a core composition or a carrier composition, appropriate to the context in which the term is used. Typically, descriptions of "combined compositions" are expressly stated as such or are clearly indicated by context.

SUMMARY OF THE INVENTION

The inventions described and claimed herein have many attributes and aspects including, but not limited to, those set forth in, e.g., described or referenced in, this Summary of the Invention ("Summary"). This Summary is not intended to be all-inclusive, and the scope of the invention is not limited to or limited by the aspects, features, elements, or embodiments provided in this Summary, which is included for illustrative purposes only and not restriction. Any of the aspects/embodiments described in this section of this disclosure can be combined with any other aspect described in this section or with any other aspect of this disclosure.

In aspects, the invention provides methods of promoting dilation of a pupil comprising administering a therapeutically effective amount of ophthalmologically suitable compositions comprising therapeutically effective amounts of each of a pharmaceutically acceptable salt of ketorolac and a pharmaceutically acceptable salt of phenylephrine, wherein the compositions lack any combination of a weak base and its conjugate acid that effectively acts as a buffer in the compositions at a pH of about 6.3 and (2) retain at least 97% of the one or more ketorolac compounds and at least 97% of the one or more phenylephrine compounds when the compositions are stored under storage conditions for at least one month, wherein the storage conditions comprise storage at about 25° C.+/−2° C., at about 25° C. and about 60% relative humidity, storage at about 40° C. and about 75% relative humidity, or storage under any combination of such conditions.

In aspects, the invention provides pharmacologically acceptable and ophthalmologically suitable compositions for use in treating or preventing ophthalmic conditions, diseases, or for use in related procedures. In aspects, such compositions comprise pharmaceutically acceptable amounts of each of one or more ketorolac compounds and one or more phenylephrine compounds, wherein the composition (1) lacks a buffer component (or lacks any significant amount of any buffer component), (2) maintains a pH of between 5.5-7, and (3) is stable under room temperature storage (e.g., conditions of about 25° C.) conditions for at least about 1 month, such as at least about 2 or at least about 3 months.

In cases, the invention provides ophthalmologically suitable compositions comprising pharmaceutically acceptable amounts of each of one or more ketorolac compounds and one or more phenylephrine compounds, wherein the compositions lack a buffer component characterizable as a combination of a weak base and its conjugate acid, a weak acid and its conjugate base, or both, such that the compositions lack a buffer component capable of preventing a significant change in pH upon the addition of even a small amount of a either a strong acid (e.g., an acid with a pKa <~3, <~1.74, or 1) or a strong base (e.g., a base with a pKa >11). E.g., adding 0.001 M HCl to pure water, the resulting pH is 3, whereas in the presence of an acetic acid buffer solution at a pH of 4.75 the effect of the addition would be to lower the pH by only 0.01 to pH 4.74. In aspects, compositions comprise pharmaceutically acceptable amounts of each of one or more ketorolac compounds and one or more phenylephrine compounds and lack a buffer component (or at least any significant amount of a buffer component), wherein a buffer component is characterizable as being capable of allowing the composition(s) to resist a significant change in pH when H+ or OH− ions are added or removed owing to other reaction(s) occurring within the same solution.

In aspects, the invention provides ophthalmologically suitable composition(s) comprising pharmaceutically acceptable amounts of each of one or more ketorolac compounds and one or more phenylephrine compounds, wherein the composition(s) lack a buffer component characterizable as a combination of a weak base and its conjugate acid, a weak acid and its conjugate base, or both, wherein the acid and base pairs of such a buffer component are present in concentrations of within 10× of one another. In aspects, the invention provides ophthalmologically suitable compositions comprising pharmaceutically acceptable amounts of each of one or more ketorolac compounds and one or more phenylephrine compounds which lack a buffer component characterizable as a combination of a weak base and its conjugate acid, a weak acid and its conjugate base, or both, having a pKa of between about 4.3-8.3, e.g., between ~5.3-~7.3, or e.g., between about ~6.0 and ~6.6.

In cases, the invention provides ophthalmologically suitable composition(s) comprising pharmaceutically acceptable amounts of each of one or more ketorolac compounds and one or more phenylephrine compounds, wherein the composition(s) lack a buffer component characterizable as a combination of a weak base and its conjugate acid, a weak acid and its conjugate base, or both; wherein the acid and base pairs of such a buffer component are present in concentrations of within 10× of one another; and wherein the pKa of any such buffer component is between 4.3-8.3, such as the pKa of any such buffer component is between 5.3-7.3, e.g., between about 6.0 and 6.6.

In aspects, the invention provides ophthalmologically suitable composition(s) comprising pharmaceutically acceptable amounts of each of one or more ketorolac compounds and one or more phenylephrine compounds, wherein the composition(s) lack a buffer component (i) wherein the buffer component is a combination of a weak base and its conjugate acid, a weak acid and its conjugate base, or both; (ii) wherein the acid and base pairs of such a buffer component are present in concentrations of within 10× of one another; (iii) wherein the pKa of the buffer component is between ~4.3-~8.3, such as the pKa of any such buffer component is between ~5.3-~7.3, or, e.g., between about 6.0 and ~6.6; and (iv) wherein, when the ophthalmologically suitable composition is at a pH of 6.3, the acid and base pairs of the buffer component can prevent a change in pH of the composition of more than ~2% when ~0.1 moles of HCl or ~0.1 moles of NaOH are added to ~1 L of the composition.

In aspects, the invention provides ophthalmologically suitable composition(s) comprising pharmaceutically acceptable amounts of each of one or more ketorolac compounds and one or more phenylephrine compounds, which lack a buffer component having any one or more of the characteristics described above, and further wherein the composition(s) are capable of retaining at least ~97% of the one or more ketorolac compounds and at least ~97% of the one or more phenylephrine compounds when stored at 25° C.+/−2° C. and about 60% relative humidity, or under accelerated storage conditions such as 40° C.+/−2° C. and about 75% relative humidity, for at least about one month, e.g., at least about 2 months or at least about 3 months.

In embodiments, the invention provides ophthalmologically suitable compositions comprising pharmaceutically acceptable amounts of each of one or more ketorolac compounds and one or more phenylephrine compounds, and further comprise one or more additional excipients, one or more additional excipients, a carrier, or any combination thereof. In aspects, such excipients can be any one or more chelating agent(s), antioxidant(s), tonicity agent(s), pH-adjusting agent(s), preservative(s), thickening agent(s)/viscosity enhancer(s), solubilizer(s), or penetration enhancer(s). In aspects, a core composition (a composition comprising one or more ketorolac compounds, one or more phenylephrine compounds, and one or more additional excipients, APIs, or both) can comprise a carrier, e.g., water, for example providing an aqueous carrier composition (core composition plus a carrier yielding a liquid carrier composition, in aspects suitable for ophthalmic delivery).

In aspects, compositions (core compositions and carrier compositions) provided by the invention can be combined with one or more other components or compositions to create a combination composition. In aspects, such a one or more other compositions is an irrigation solution. In aspects, such an irrigation solution comprising composition(s) provided by the invention are suitable for ophthalmic delivery.

According to aspects, the invention provides methods of manufacturing composition(s) described in this section. In aspects, the invention provides a method of manufacturing a composition described in this section, e.g., specifically a carrier composition, wherein the method comprises (1) forming a solution of a ketorolac compound; (2) dissolving a phenylephrine compound in the ketorolac compound solution; (3) diluting the ketorolac compound-phenylephrine compound solution resulting from (2); (4) adjusting the diluted ketorolac compound-phenylephrine compound solution of (3) to a pH of between about 6.0-about 6.6, e.g., to a pH of about 6.3; and (5) bringing the final volume of the solution up to a final volume to yield an ophthalmologically suitable carrier solution comprising ketorolac in an amount of between about 0.1-about 5 wt/v. %, such as, e.g., between ~0.1-~3 wt/v. %, or between ~0.1-~1 wt/v. %, and phenylephrine in an amount of between about 0.1-about 10 wt/v. %, such as, e.g., between ~0.5-~5 wt/v. %, or between ~1-2%. In aspects, the invention provides methods wherein one or more pharmacologically acceptable and ophthalmologically suitable excipients is completely dissolved in a carrier material prior to the addition of ketorolac.

In cases, the invention provides a kit including any of the pharmacologically acceptable and ophthalmologically suitable compositions described above, where the composition is packaged and provided in container(s) (e.g., single use container(s)) and the kit further comprises one or more delivery devices for (1) administering the composition to a recipient; (2) delivering the composition to an existing composition, device, or system for delivery to a recipient (such as, e.g., an existing controlled-release, ophthalmic irrigation system), or (3) both (1) and (2).

According to embodiments, the invention provides a method of (1) preventing significant inflammation during or after an ophthalmologically-related procedure, (2) significantly maintaining suitable pupil size (e.g., preventing significant intraoperative miosis) during an ophthalmologically-related procedure, (3) detectably or significantly reducing postoperative ocular pain following an ophthalmologically-related procedure, or (4) any combination thereof, comprising application of a composition during such an ophthalmologically-related procedure, for a period of time after such an ophthalmologically-related procedure, or both, the composition comprising pharmaceutically acceptable amounts of each of one or more ketorolac compounds and phenylephrine compound(s), wherein the composition lacks a buffer component having any one or more of the characteristics described in this section, the composition maintains a pH of between ~5.5-7, and the composition retains at least 97% of the ketorolac compound(s) and at least 97% of the phenylephrine compound(s) when stored at 25° C.+/−2° C. and about 60% relative humidity, or under accelerated storage conditions such as 40° C.+/−2° C. and about 75% relative humidity, for at least about 1 month, such as, e.g., at least about 2 months or at least about 3 months. In aspects, the method comprises use of the composition in the form of a combination composition, e.g., the composition is one component of a composition comprising additional ophthalmologically suitable component(s), forming a combination composition used in the method.

In facets, the invention further provides a method of treating or preventing a disease or condition benefiting from a combination therapy of an anti-inflammatory and mydriatic compound, the method comprising administering an effective amount of a composition comprising pharmaceutically acceptable amounts of each of one or more ketorolac compounds and one or more phenylephrine compounds, wherein the composition (1) lacks a buffer component having any one or more of the characteristics described in this section, (2) maintains a pH of between 5.5-7; and (3) retains at least 97% of the one or more ketorolac compounds and at least 97% of the one or more phenylephrine compounds in the composition when stored at 25° C.+/−2° C. and about 60% relative humidity, or under accelerated storage conditions such as 40° C.+/−2° C. and about 75% relative humidity, for at least about one month, such as, e.g., at least about 2 or at least about 3 months. In aspects, such a method comprises use of the composition as a component in a combination composition, e.g., the composition is one component of a composition comprising at least one additional ophthalmologically suitable component, forming a combination composition used in the method.

In aspects, the invention provides a composition as described in this section, wherein the composition is suitable for use in an irrigation solution, wherein the composition can adapt to the pH of the irrigation solution or, e.g., to a physiological environment to which it is added (e.g., an eye) due to its buffer-free nature, "buffer-free" meaning lacking a buffer component as described herein.

In aspects, the invention provides ophthalmologically suitable compositions that surprisingly and unexpectedly are capable of maintaining stability of such APIs, substantially/significantly maintaining the initial pH of the composition, or both, over extended periods of time as exemplified in the examples provided herein, e.g., for 1, 2, 3, or 6 months or longer. In aspects, formulations of the invention are unexpectedly and surprisingly associated with, e.g., low levels of API-associated impurities, e.g., less than 2%, less than 1.5%, less than 1%, less than 0.75%, or less than about 0.5% ketorolac-associated impurities, phenylephrine-associated impurities, or both, despite the lack of certain elements (e.g., a buffering component) and storage over an extended period of time (e.g., at least 1, 2, 3, or 6 months, or even longer). In aspects, compositions of the invention are unexpectedly and surprisingly associated with retention of, e.g., at least about 97%, ≥~97.5%, ≥~98%, or greater than (e.g., on average over several measured timepoints/tests)≥~98.5% of the initial amount of ketorolac, phenylephrine, or both, when maintained in a composition of the invention (even a buffer-free composition) for extended periods of time (e.g., ≥1, 2, 3, or 6 months).

DETAILED DESCRIPTION OF THE INVENTION

For convenience, both combinations of elements/steps and individual elements/steps may be described in this section of this disclosure. Despite the inclusion of passages focused on specific elements/steps, any aspect, facet, embodiment, or other description of particular step(s) or element(s) can be applied to any general description of the compositions/methods of the invention, or any other recited element(s)/step(s) thereof, which are provided in any part of this disclosure.

Core Compositions and Carrier Compositions

The invention provides compositions of the invention ("compositions") comprising one or more pharmacologically acceptable/ophthalmologically suitable ketorolac compounds and one or more pharmacologically acceptable/ophthalmologically suitable phenylephrine compounds, and optionally one or more pharmacologically acceptable and ophthalmologically suitable excipients, optionally additional pharmacologically acceptable and ophthalmologically suitable active pharmaceutical ingredient(s) (API(s)), and optionally a pharmacologically acceptable/ophthalmologically suitable carrier, wherein such compositions lack a buffer component, the buffer component and lack thereof described in detail elsewhere herein.

Typically, composition(s) provided by the invention comprise a carrier. In aspects the carrier is such that the carrier establishes the composition as having or taking on a liquid form. In aspects, the carrier can mostly comprise, substantially only comprise, essentially only comprise, or consist of/be water, which may be a water of a particular grade/quality, e.g., water that can be characterized as water for injection (WFI). In aspects, carrier compositions that are characterizable as aqueous compositions are provided (e.g., are compositions comprising ≥51% water, such as, in aspects, ≥65%, ≥75%, ≥80%, ≥85%, ≥90%, or ≥95% water).

In aspects, composition(s) provided by the invention also can be described by components other than their carrier. E.g., in aspects composition(s) provided by the invention can be characterized by their APIs and excipient(s), or, alternatively, by the absence of particular API(s), particular excipient(s), or combination(s) thereof. Terms described below can be used to describe components of various types of compositions.

In aspects, the invention provides core compositions comprising pharmacologically acceptable and ophthalmologically suitable ketorolac compound(s), pharmacologically acceptable and ophthalmologically suitable phenylephrine compound(s), and optionally any one or more additional pharmacologically acceptable and ophthalmologically suitable excipients (e.g., chelating agent(s), antioxidant(s), etc.) or additional pharmacologically acceptable and ophthalmologically suitable active pharmaceutical ingredient(s) (API(s)). In aspects, a core composition is provided in solid form (e.g., in a dry powder form) or in semi-solid form. In aspects, a core composition is unsuitable for direct ocular administration (e.g., without the inclusion of other elements of the composition/formulation). In aspects, a core composition is configured for/adapted to reconstitution prior to use.

In aspects, the invention provides carrier compositions comprising a pharmacologically acceptable and ophthalmologically suitable carrier (e.g., water) in combination with a core composition. A carrier typically will cause the core composition to be contained in (carried in) a liquid (e.g., an aqueous composition or other solution), other fluid form, a colloidal form (e.g., a gel), etc. In aspects, a carrier is mostly, generally, or entirely composed of material(s)/ingredient(s) that are liquid at room temperature and typically at normal ambient environmental temperatures (e.g., ~1° C. or ~5° C. to ~50° C. or ~55° C.). A carrier can comprise any suitable number of ingredients in any suitable form (e.g., an ophthalmological emulsion). In aspects, a carrier mostly, generally, substantially, essentially, or entirely is composed of a single ingredient (e.g., water for injection). A carrier composition can, in aspects, be suitable for direct ocular administration (e.g., determined sufficiently nontoxic, nonirritating, etc., as determined by, e.g., prior regulatory authority approval, such as prior FDA approval, or established as such through well controlled and adequate clinical trials). In aspects, the invention provides carrier compositions comprising pharmacologically acceptable and ophthalmologically suitable ketorolac compound(s), pharmacologically acceptable and ophthalmologically suitable phenylephrine compound(s), pharmacologically acceptable and ophthalmologically suitable carrier(s), and optionally any one or more additional pharmacologically acceptable and ophthalmologically suitable excipients (e.g., chelating agent(s) (e.g., EDTA), antioxidant(s), etc.) or additional pharmacologically acceptable and ophthalmologically suitable active pharmaceutical ingredient(s) (APIs), which composition is in liquid form (e.g., in aqueous form). A carrier composition can, in aspects, be suitable for direct ocular administration without further dilution or, in aspects, may require dilution prior to use. In cases, a carrier composition may not be suitable for direct ocular administration without further dilution of the composition prior to administration, e.g., without further dilution with an irrigation solution, e.g., an irrigation solution as known in the art and commonly used in ophthalmic procedures for which the present compositions are appropriate for use. In aspects, the combination of a carrier composition with an irrigation solution does not detectably or significantly negatively impact the stability, performance (e.g., efficacy, or stability and performance (e.g., efficacy) of any one or more active pharmaceutical ingredients in the carrier composition, In aspects, the invention provides combined compositions comprising a core composition or carrier composition plus one or more additional components that are capable of being used ophthalmologically independently of the other components of the combined composition (e.g., irrigation solution(s) are examples of such additional components/compositions). See, e.g., McDermott, M L, et. al. Ophthalmic Surg. 1988 October; 19(10):724-33, and, e.g., Pucket, Tedd R. et. al. Ophthalmology, Feb. 1, 1995, Vol. 102, Issue 2, pp. 291-296, and exemplary ophthalmic irrigation solutions such as Naystel®, BSS®, BSS Plus®, AMO® Endosol, AMO® Endosol Extra, etc. In aspects, the invention further provides methods of making such compositions and using such compositions.

Ketorolac Compounds

In aspects, the invention provides ophthalmic compositions comprising one or more pharmaceutically acceptable and ophthalmologically suitable compounds which, when provided in therapeutically effective amounts, provide detectable or significant anti-inflammatory effects/properties. In aspects, such effect(s)/property(ies) is/are typically provided by one or more ketorolac compounds. In aspects, the ketorolac compound(s) comprise ketorolac.

Ketorolac is a cyclized propionic acid non-steroidal anti-inflammatory drug (NSAID) having anti-inflammatory and analgesic properties and the following structure:

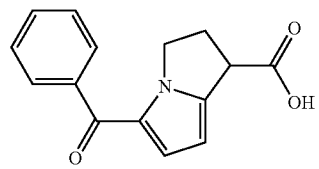 [SMILES: O=C(c1ccccc1)c1ccc2n1CCC2C(=O)O]

In aspects, compositions comprise any form of pharmaceutically acceptable and ophthalmologically suitable ketorolac compound(s), such as, e.g., any pharmaceutically acceptable prodrug, hydrate, salt, solvate, enantiomer, or polymorph of ketorolac. In aspects, ketorolac compounds of the compositions can comprise any ophthalmologically suitable analog or derivative of ketorolac. In aspects, compositions comprise a single type of ketorolac compound, while in alternative aspects, compositions can comprise two or more types of ketorolac compounds e.g., two different derivatives of ketorolac, each differing from the other in, e.g., one or more of their compound size, level of detectable effect (e.g., anti-inflammatory strength), pKa value, etc.

In aspects, compositions comprise a salt of ketorolac. In aspects, compositions comprise ketorolac tromethamine, which has this structure:

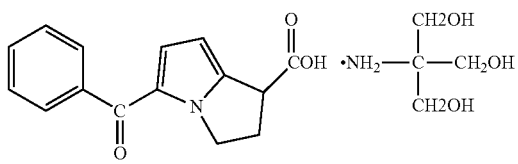

Ketorolac tromethamine (IUPAC name 2-amino-2-(hydroxymethyl)propane-1,3-diol; 5-benzoyl-2,3-dihydro-1H-pyrrolizine-1-carboxylic acid, chemical formula C19H24N2O6) is the tromethamine salt of ketorolac (molecular weight of 376.4, pKa value of about 3.5). In aspects, the tromethamine salt of ketorolac is present in the composition(s) provided by the invention as a racemic mixture of [−]S- and [R]-enantiomeric forms of ketorolac. In aspects, ketorolac is present in the composition(s) in at least predominantly, at least generally, at least substantially, or, e.g., is completely present in pure HS-enantiomeric form. In certain alternative aspects, ketorolac is present in the composition(s) in at least predominantly, at least generally, at least substantially, or, e.g., is completely present in pure [−]R-enantiomeric form. In aspects, ketorolac is present in the composition(s) as a racemic mixture of [−]S- and [−]R-enantiomeric forms, wherein such enantiomers are present in an approximately 1:1 ratio, e.g., in a ratio of about 0.8:1, ~0.9:1, ~1:1, ~1:1.1, or about ~1:1.2 [−]S- to [−]R-enantiomeric form. In certain alternative aspects, one enantiomer is present in an amount detectably or significantly higher or lower than another enantiomer, such as, e.g., the composition has a ratio of [−]S- to [−]R-enantiomers of approximately ~1.1:1, ~1.2:1, ~1.3:1, ~1.4:1, ~1.5:1, ~1.6:1, ~1.7:1, ~1.8:1, ~1.9:1, or about 2:1, such as ~3:1, ~4:1, ~5:1, ~6:1, ~7:1, ~8:1, ~9:1, or ~10:1 or more, such as ~20:1, ~40:1, ~60:1, ~80:1, or ~100:1 or more, or, e.g., the composition has a ratio of [−]S- to [−]R-enantiomers of approximately ~1:1.1, ~1:1.2, ~1:1.3, ~1:1.4, ~1:1.5, ~1:1.6, ~1:1.7, ~1:1.8, ~1:1.9, or about 1:2, such as ~1:3, ~1:6, ~1:7, ~1:8, ~1:9, or ~1:10 or more, such as ~1:20, ~1:40, ~1:60, ~1:80, or ~1:100, or more.

In aspects, compositions comprise a pH of between about 5.0-8.0, and more typically between a pH of between about 6.2-6.4 as is described elsewhere herein. Accordingly, given the 3.5 pKa of ketorolac tromethamine, at such pH ranges, ketorolac tromethamine is unable to operate as a buffer, and, accordingly, does not operate as a buffer component (the term "buffer component" being described in further detail elsewhere herein). That is, in aspects, (1) ketorolac compounds of the composition are not present as a weak base with its conjugate acid, a weak acid and its conjugate base, or both; (2) any acid-base pairs of such compounds are not present within concentrations of 10× of one another (e.g., not within 15×, 20×, or 25× of each other) in the composition (meaning that one of the pair will be present in at least 10 times the concentration of the other); (3) any ketorolac compounds in the composition do not have pKa values of between about 4.3-about 8.3, such as, e.g., between ~4.5-~8, ~5.3-~7.3, ~5.5-~7.0, ~6.0-~6.6, or, e.g., ~6.2-~6.4; or (4) when the composition is at a pH of about 6.3, any acid and base pairs of any ketorolac compound cannot prevent or cannot significantly prevent a change in pH of the composition or prevent a change in pH of the composition of more than 2% (e.g., more than 1%) when 0.1 moles of HCl or 0.1 moles of NaOH are added to 1 L of the composition. These principles can be similarly applied to other components of compositions, to maintain a low buffer or buffer free state in the composition, as will be at least somewhat further exemplified below.

In aspects, suitable ketorolac compounds of the compositions, when provided in a therapeutically effective amount, provide one or more of a detectable or significant analgesic effect, anti-inflammatory effect, or both; or another effect associated with ketorolac compounds, such as, e.g., inhibiting cyclooxygenase-1 (COX-1) enzymes, COX-2 enzymes, or both, when administered to suitable subjects, such as human patients. In aspects, such compositions or applications treat or prevent one or more ocular conditions described herein or that are treatable (or preventable) by ketorolac compositions as known in the art.

In aspects, a ketorolac compound comprises or is an analog or derivative of ketorolac that maintains most, generally all, or at least substantially all of the physiological or therapeutic effects of ketorolac. In aspects, a ketorolac compound is an analog or derivative of ketorolac that maintains most, generally all, or at least substantially all of the physiological or therapeutic effects of ketorolac or improved properties thereto, and maintains similar physicochemical properties (e.g., about the same pKa) as ketorolac or is clearly derived from ketorolac. Ketorolac derivatives such as ketogal are known in the art (see, e.g., Russo et al. Front Pharmacol. 2017 Nov. 6; 8:757, WO200207868, and U.S. Pat. No. 6,646,003), as are products of ketorolac (see, e.g., Curcio et al., June 2009. Journal of Medicinal Chemistry 52(12):3794-800). Skilled persons may be able to generate, identify, or apply such or similar ketorolac derivatives (e.g., derivatives comprising one or more added moieties/groups (e.g., an alkyl, heteroalkyl, or cycloalkyl group) or additional atoms, e.g., 1-3, 1-2, or 1 added groups/atoms to ketorolac) or analogs (e.g., analogs having substitutions of 1-5 atoms, 1-4, 1-3, 1-2 atoms, or a single atom (e.g., by deuterium/hydrogen replacement, boron/carbon replacement, addition of fluorine, etc.). In aspects, ketorolac compounds of a composition are mostly, generally, substantially, essentially, or only composed of ketorolac (in any of the forms described herein) or a suitable salt thereof. In aspects, inactive/undesirable impurity of an API, is not considered an API-associated compound.

According to aspects, the invention provides an ophthalmologically suitable composition comprising a ketorolac compound, such as, e.g., a salt of ketorolac such as, e.g., ketorolac tromethamine, wherein the ophthalmologically suitable ketorolac compound is present in the composition in an amount of between about 0.1 wt/v. %-5.0 wt/v. %, such as, e.g., ~0.1 wt/v. %-~4.0 wt/v. %, ~0.1 wt/v. %-~3.0 wt/v. %, ~0.1 wt/v. %-~2.0 wt/v. %, or ~0.1 wt/v. %-~1.0 wt/v. %, e.g., ~0.2 wt/v. %-~0.5 wt/v. %, ~0.3 wt/v. %-~0.5 wt/v. %, ~0.4 wt/v. %-~0.5 wt/v. %, such as, e.g., ~0.2 wt/v. %-~0.4 wt/v. %, or, e.g., between about 0.3 wt/v. %-about 0.5 wt/v. %.

According to aspects, the invention provides an ophthalmologically suitable composition comprising a ketorolac compound, such as, e.g., a salt of ketorolac such as, e.g., ketorolac tromethamine, wherein the ophthalmologically suitable ketorolac compound is present in the composition in an amount of between about 0.5 mg/mL-about 10 mg/mL, such as ~0.5 mg/mL-~9 mg/mL, ~0.5 mg/mL-~8 mg/mL, ~0.5 mg/mL-~7 mg/mL, ~0.5 mg/mL-6 mg/mL, or, e.g., ~0.5 mg/mL-5 mg/mL, such as for example between about 1 mg/mL-about 10 mg/mL, ~1.5 mg/mL-~10 mg/mL, ~2 mg/mL-~10 mg/mL, ~2.5 mg/mL-~10 mg/mL, ~3 mg/mL-~10 mg/mL, ~3.5 mg/mL-~10 mg/mL, or, e.g., ~4 mg/mL-~10 mg/mL, as in, e.g., between ~1 mg/mL-~7 mg/mL, ~2 mg/mL-~6 mg/mL, ~3 mg/mL-5 mg/mL, e.g., ~3.5 mg/mL-4.5 mg/mL, such as in one specific example, about 4.2 mg/mL.

According to aspects, the invention provides an amount of a ketorolac compound, e.g., a salt of ketorolac, e.g., ketorolac tromethamine, which is equivalent to between about 0.3 mg/mL-6.9 mg/mL of ketorolac, such as, e.g., between ~0.5 mg/mL-~6.5 mg/mL, ~1 mg/mL-~5 mg/mL, ~1 mg/mL-~3 mg/mL, ~1.5 mg/mL-~3 mg/mL, or, e.g., ~2 mg/mL-3 mg/mL, such as, e.g., ~2.88 mg/mL of ketorolac. About 4.24 mg/mL ketorolac tromethamine is equivalent to about 2.88 mg/mL ketorolac. In aspects, conversion of amounts of ketorolac tromethamine herein and ketorolac can be calculated using similar conversion methods familiar to those in the art and, accordingly, disclosure directed to exemplary amount(s) of ketorolac tromethamine should be interpreted as disclosing the equivalent amount(s) of ketorolac.

In aspects, as indicated from the preceding, a ketorolac compound is a salt of ketorolac or a different ketorolac-related compound (e.g., a ketorolac derivative). Salts of APIs of compositions of the invention can comprise any pharmaceutically/ophthalmologically suitable salt form. Alternative salt forms that are suitable can be identified through routine experimentation given the guidance provided herein, in view of knowledge in the art, regarding the APIs of the compositions of the invention and desired characteristics of compositions. Salts that typically are pharmaceutically acceptable include those formed from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of typically suitable salts derived from inorganic bases include, but are not limited to, aluminum, ammonium, calcium, copper, ferric, ferrous, lithium, magnesium, manganic, mangamous, potassium, sodium, and zinc. Not all of such forms are suitable for any given API, as will be understood by readers. Nonetheless, APIs disclosed herein can include any suitable salt forms, which can include any suitable one or more of such typically used salt forms.

Phenylephrine Compounds

In aspects, the invention provides ophthalmic compositions comprising one or more pharmaceutically acceptable and ophthalmologically suitable compounds which, when delivered to the eye of a subject in sufficient amounts, result in detectable or significant mydriatic properties (that is, provide detectable or significant dilation of the pupil of the eye), such as mydriatic effects approximately the same or significantly similar to those typically provided by a corresponding amount of phenylephrine hydrochloride (HCl) or that provide an improvement on such effects. In aspects, such compositions comprise one or more phenylephrine compounds. In aspects, one or more of such phenylephrine compounds provide therapeutic effects significantly similar to, or that improve upon, therapeutic effects associated with phenylephrine HCl in provided in similar application(s) and amount(s). In aspects, phenylephrine compounds are mostly, generally, or only composed of phenylephrine, rather than an analog or derivative thereof. In aspects, phenylephrine compounds comprise, mostly comprise, or only comprise one or more suitable phenylephrine analogs or derivatives, which can have similar types of modifications as those described above with respect to ketorolac compounds (e.g., varying by addition of 1 or 2 atoms/groups or by substitution with 1 or 2 atoms, while retaining suitable activity and suitability characteristics or improving on one or both thereof). E.g., phenylephrine derivatives can have a pKa that is within about (+/−) 20%, 15%, or 10% of phenylephrine HCl, as well as significantly similar therapeutic properties. Ophthalmological prodrug derivatives of phenylephrine have been described in the art (see, e.g., AU1988015315 or U.S. Pat. No. 4,866,083) and such or similar compounds may be adaptable to or directly usable in compositions and methods of the invention. Phenylephrine compounds also can comprise suitable alternative salt forms, e.g., comprising one of the various salt forms provided elsewhere herein or that are otherwise known in the art.

In aspects, most, generally all, or all of the phenylephrine compound(s) comprise phenylephrine in one or more salt/stereoisomeric forms. Phenylephrine is direct-acting sympathomimetic amine having decongestant, vasoconstrictive, and mydriatic properties, and has a structure as shown below:

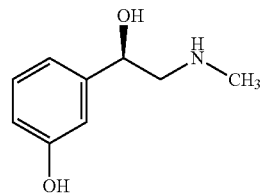

In aspects, compositions can comprise any form of pharmaceutically/ophthalmologically suitable phenylephrine compound, such as, e.g., any pharmaceutically acceptable prodrug, hydrate, salt, solvate, enantiomer, or polymorph thereof. In aspects, phenylephrine compounds can comprise any ophthalmologically suitable analog or derivative of phenylephrine. In aspects, compositions comprise a single type of phenylephrine compound, while in alternative aspects, compositions can comprise two or more types of phenylephrine compounds e.g., two different derivatives of phenylephrine, each differing from the other in, e.g., their compound size, level of detectable effect (e.g., mydriatic activity), pKa value, etc.

In aspects, compositions comprise a salt of phenylephrine. In certain specific aspects, compositions comprise phenylephrine hydrochloride (phenylephrine HCl), shown below:

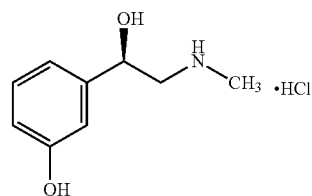

Phenylephrine HCl (IUPAC name 3-[(1R)-1-hydroxy-2-(methylamino)ethyl]phenol; hydrochloride; chemical formula $C_9H_{13}NO_2 \cdot HCl$ or C9H14ClNO2) is the hydrochloride salt of phenylephrine. Phenylephrine HCL acts as an al-adrenergic receptor agonist. Phenylephrine HCl has molecular weight of 203.66 and a pKa value of about 9.07. In aspects, the hydrochloride salt of phenylephrine is at least predominantly, at least generally, at least substantially, or, e.g., is completely present in the composition(s) provided by the invention in [-]R-enantiomer form of phenylephrine. In aspects, compositions comprise phenylephrine HCl wherein the phenylephrine HCL is comprised of at least about 75%, ≥~80%, ≥~85%, ≥~90%, ≥~95%, ≥~97%, ≥~98%, ≥~99%, ≥~99.5%, ≥~99.9%, or e.g., 100% the [-]R-enantiomer of phenylephrine. In alternative aspects, phenylephrine HCl is present in the composition(s) provided by the invention as a racemic mixture of [-]S- and [-]R-enantiomeric forms, wherein such enantiomers are present in an approximately 1:1 ratio, e.g., in a ratio of about 0.8:1, ~0.9:1, ~1:1, ~1:1.1, or about ~1:1.2 [-]S- to [-]R-enantiomeric form. In certain alternative aspects, one enantiomer is present in an amount detectably or significantly higher or lower than another enantiomer, such as, e.g., the composition has a ratio of [-]S- to [-]R-enantiomers of approximately ~1.1:1, ~1.2:1, ~1.3:1, ~1.4:1, ~1.5:1, ~1.6:1, ~1.7:1, ~1.8:1, ~1.9:1, or about 2:1, such as ~3:1, ~4:1, ~5:1, ~6:1, ~7:1, ~8:1, ~9:1, or ~10:1 or more, such as ~20:1, ~40:1, ~60:1, ~80:1, or ~100:1 or more, or, e.g., the composition has a ratio of [-]S- to [-]R-enantiomers of approximately ~1:1.1, ~1:1.2, ~1:1.3, ~1:1.4, ~1:1.5, ~1:1.6, ~1:1.7, ~1:1.8, ~1:1.9, or about 1:2, such as ~1:3, ~1:4, ~1:5, ~1:6, ~1:7, ~1:8, ~1:9, or ~1:10 or more, such as ~1:20, ~1:40, ~1:60, ~1:80, or ~1:100 or more.

In aspects, compositions comprise a pH of between about 5.0-~8.0, and more typically between a pH of between about 6.2-6.4 as is described elsewhere herein. Accordingly, given the 9.07 pKa of phenylephrine HCl, at such pH ranges, phenylephrine HCl is unable to operate as a buffer in the context of compositions of the invention, and, accordingly, cannot be characterized as a buffer component (the term "buffer component" being described in further detail elsewhere herein). In aspects, (1) no phenylephrine compounds of the composition are present as a weak base with its conjugate acid, a weak acid and its conjugate base, or both; (2) any acid-base pairs of such phenylephrine compounds are not present within concentrations of 10×, 15×, or 20× of one another; (3) any phenylephrine compounds in the composition do not have a pKa values of between about 4.3-about 8.3, such as, e.g., between ~4.5-~8, ~5.3-~7.3, ~5.5-~7.0, ~6.0-~6.6, or, e.g., ~6.2-~6.4; or (4) when the composition is at a pH of about 6.3, any acid and base pairs of the phenylephrine compound cannot prevent a change in pH of the composition of more than 3%, 2%, or 1%, when 0.1 moles of HCl or 0.1 moles of NaOH are added to 1 L of the composition.

In aspects, suitable phenylephrine compounds of the compositions, when provided in a therapeutically effective amount, provide a detectable or significant mydriatic effect or other detectable or significant physiological effect of phenylephrine when delivered in an effective amount (e.g., vasoconstriction, systolic/diastolic pressure increases, and the like). In aspects, effective amounts of phenylephrine compound(s) treat or prevent one or more ocular conditions described herein.

Further provided are ophthalmologically suitable compositions comprising a phenylephrine compound, e.g., a salt of phenylephrine, e.g., phenylephrine hydrochloride, wherein the ophthalmologically suitable phenylephrine compound is present in the composition in an amount of between about 0.1 wt/v. %-10.0 wt/v. %, such as, e.g., ~0.1 wt/v. %-~8.0 wt/v. %, ~0.1 wt/v. %-~6.0 wt/v. %, ~0.1 wt/v. %-~4.0 wt/v. %, ~0.1 wt/v. %-~2.0 wt/v. %, or, e.g., 0.1 wt/v. %-10 wt/v. %, 0.2 wt/v. %-10 wt/v. %, 0.3 wt/v. %-10 wt/v. %, 0.4 wt/v. %-10 wt/v. %, 0.5 wt/v. %-10 wt/v. %, 0.6 wt/v. %-10 wt/v. %, 0.7 wt/v. %-10 wt/v. %, 0.8 wt/v. %-10 wt/v. %, 0.9 wt/v. %-10 wt/v. %, as in, e.g., 0.2 wt/v. %-8 wt/v. %, 0.4 wt/v. %-6 wt/v. %, 0.6 wt/v. %-4 wt/v. %, or, e.g., 0.8 wt/v. %-2 wt/v. %, or, e.g., ~0.5 wt/v. %-~1.5 wt/v. %, or ~1.0 wt/v. %-~1.5 wt/v. %.

An aspect is an ophthalmologically suitable composition comprising an effective amount of phenylephrine compound(s), such as, e.g., a salt of phenylephrine such as, e.g., phenylephrine HCl, wherein the ophthalmologically suitable phenylephrine compound is present in the composition in an amount of between about 5 mg/mL-about 20 mg/mL, such as ~5 mg/mL-~18 mg/mL, ~5 mg/mL-~16 mg/mL, ~5 mg/mL-~14 mg/mL, or, e.g., ~5 mg/mL-13 mg/mL, such as for example between about 6 mg/mL-about 20 mg/mL, ~8 mg/mL-~20 mg/mL, ~10 mg/mL-~20 mg/mL, or, e.g., ~11 mg/mL-~20 mg/mL, as in, e.g., between ~6 mg/mL-~18 mg/mL, ~8 mg/mL-~16 mg/mL, ~10 mg/mL-14 mg/mL, e.g., ~11 mg/mL-13 mg/mL, such as in one specific example, about 12.4 mg/mL. In general, an "effective amount" of an API of a composition, or a composition overall, as exemplified/discussed elsewhere, is an amount that is suitable for causing a significant therapeutic effect in a subject, such as a human patient. As discussed below, "efficacy" and "effectiveness" in terms of excipients and other ingredients is determined by a measurable or significant effect of an intended purpose.

According to additional aspects, the invention provides an amount of a phenylephrine compound, e.g., a salt of phenylephrine, e.g., phenylephrine HCl which is equivalent to between about 4 mg/mL-about 17 mg/mL phenylephrine, such as, e.g., ~5 mg/mL-~15 mg/mL, ~7 mg/mL-~12 mg/mL, ~9 mg/mL-~11 mg/mL, ~10 mg/mL-~11 mg/mL, such as, e.g., ~10.16 mg/mL phenylephrine. About 12.4 mg/mL phenylephrine hydrochloride is equivalent to about 10.16 mg/mL of phenylephrine. In aspects, conversion of amounts of phenylephrine hydrochloride provided herein and phenylephrine can be calculated using similar conversion methods familiar to those in the art and, accordingly, disclosure directed to exemplary amount(s) of phenylephrine hydrochloride should be interpreted as similarly disclosing the equivalent amount(s) of phenylephrine.

Combinations of Ketorolac Compound(s)+Phenylephrine Compound(s)

In aspects, compositions comprise effective amounts of pharmaceutically/ophthalmologically suitable ketorolac compound(s) and phenylephrine compound(s). In aspects, the compounds are in a single composition in about fixed amounts.

In aspects, ketorolac compound(s) present within the composition do not detectably or significantly impact the efficacy, e.g., the mydriatic activity of, any one or more phenylephrine compound of the composition. Correspondingly, in aspects, the phenylephrine compound(s) present within the composition also do not detectably or significantly impact the efficacy, e.g., the anti-inflammatory strength or activity of, any one or more ketorolac compounds of the composition. In aspects no ketorolac compound(s) in the composition(s) cause(s) a detectable or significant detrimental impact to the recipient, such as, e.g., one or more unintended side effect(s), e.g., due to the copresence of the one or more phenylephrine compound(s), and no phenylephrine compound(s) present in the composition(s) cause(s) a detectable or significant detrimental impact to the recipient, such as, e.g., one or more unintended side effects), e.g., due to the copresence of the one or more ketorolac compound(s). In aspects, compounds other than ketorolac or its typical salt in a composition exhibit at least about similar efficacy and safety as ketorolac or statistically similar safety or efficacy in the same or substantially similar composition (i.e., other than the non-ketorolac compound) at about the same amount or at the same amount. In aspects, compounds other than phenylephrine or its typical salt in a composition of the invention exhibit at least about similar efficacy and safety as ketorolac or statistically similar safety or efficacy in the same or substantially similar composition at the same amount or about the same amount.

Further, in aspects, the one or more ketorolac compounds, e.g., ketorolac tromethamine, and the one or more phenylephrine compounds, e.g., phenylephrine HCl, act synergistically in preventing clinically significant levels of miosis (constriction of the pupil of the eye). That is, in aspects, one or more phenylephrine compounds and one or more ketorolac compounds act synergistically to maintain mydriasis. In aspects, such synergy reduces ophthalmological procedure-related complications due to pupil diameter reduction, when such compositions are used in conjunction with procedures where pupil diameter reduction is problematic. For example, in aspects, administering the compounds, e.g., one or more phenylephrine compounds and one or more ketorolac compounds together provides a detectable or significant increase in mydriatic activity over that of either compound administered alone. In aspects, the compounds work synergistically to reduce postoperative pain compared to pain reduction provided by either compound alone. For example, in aspects administering the one or more phenylephrine compounds and one or more ketorolac compounds together provide a detectable or significant increase in analgesic activity over that of either compound administered alone. In aspects, the one or more ketorolac compounds, e.g., ketorolac tromethamine, and the one or more phenylephrine compounds, e.g., phenylephrine HCl, act synergistically in preventing clinically significant levels of inflammation. For example, in aspects, administering the two compounds together provide a detectable or significant increase in anti-inflammatory activity over that of either compound administered alone. In aspects, compositions of the invention exhibit about the same effects, or statistically similar effects, or are otherwise deemed bioequivalent, to a known composition of ketorolac and phenylephrine (e.g., OMIDRIA as sold in the United States on the date of this submission or a reference product, such a "reference product" being defined elsewhere herein), surprisingly though the compositions of the invention are stored for substantial periods of time (e.g., at least 2, 3, or 6 months) without inclusion of any buffering agent/component.

In aspects, the ophthalmologically suitable composition(s) provided by the invention comprise one or more ketorolac compounds, e.g., ketorolac tromethamine, and one or more phenylephrine compounds, e.g., phenylephrine HCl, in a fixed ratio or within an approximate range of a fixed ratio or a range of ratios that are significantly similar in terms of the resulting efficacy of the composition. In aspects, the ratio of ketorolac compound(s), e.g., ketorolac tromethamine, to phenylephrine compound(s), e.g., phenylephrine HCl, is between about 1:1-about 1:13, such as, e.g., ~1:1-~1:10, ~1:1-~1:8, ~1:1-~1:6, ~1:1-~1:5, as in, e.g., ~1:2-~1:4, or in specific aspects, about 1:3.

According to alternative aspects, the ratio of ketorolac compound(s), e.g., ketorolac tromethamine, to phenylephrine compound(s), e.g., phenylephrine HCl, is between about 1:1-about 13:1, such as, e.g., ~1:1-~10:1, ~1:1-~8:1, ~1:1-~6:1, ~1:1-~5:1, as in, e.g., ~2:1-~4:1, or in specific aspects, about 3:1.

In aspects, composition(s) comprise between about 0.1-about 0.5 wt/v. % ketorolac tromethamine and between about 1.0 wt/v. %-1.5 wt/v. % phenylephrine HCl, such as, e.g., between ~0.2 wt/v. %-about 0.5 wt/v. % ketorolac tromethamine and between about 1.1 wt/v. %-1.4% phenylephrine HCl, e.g., between about 0.3 wt/v. %-about 0.5 wt/v. % ketorolac tromethamine and between about 1.1 wt/v. %-1.3 wt/v. % phenylephrine HCl, such as in one specific example about 0.3 wt/v. % or ~0.4 wt/v. % ketorolac such as ketorolac tromethamine (e.g., about 0.25 wt/v. %-~0.5 wt/v. %, ~0.275-~0.45 wt/v. %, or ~0.28 wt/v. %-~0.42 w/v % ketorolac) and about 1.2 wt/v. % phenylephrine, such as phenylephrine HCl (e.g., ~1 wt/v. %-~1.5 w/v %, ~1.05 wt/v. %-~1.35 w/v %, or ~1.1 wt/v. %-~1.25 w/v % phenylephrine HCl).

In aspects, composition(s) provided by the invention comprise between about 2-about 6 mg/mL ketorolac tromethamine and between about 8-about 16 mg/mL phenylephrine HCl, such as, e.g., between ~3-5 mg/mL ketorolac tromethamine and between ~10-14 mg/mL phenylephrine HCl, e.g., between ~3.5-4.5 mg/mL ketorolac tromethamine and between ~11-13 mg/mL phenylephrine HCl, or, e.g., in one specific embodiment, 4.2 mg/mL ketorolac tromethamine and about 12.4 mg/mL phenylephrine HCl.

Excipients and Additional APIs

In aspects, the invention provides pharmaceutically acceptable and ophthalmologically suitable composition(s) for use in treating or preventing ophthalmic conditions, diseases, or for use in related procedures, comprising pharmaceutically acceptable amounts of each of ketorolac compound(s) and phenylephrine compound(s), wherein the composition is characterized in one or more ways by other formulation elements or characteristics thereof, described herein. In an exemplary aspect, such a composition (1) lacks a buffer component (such a buffer component being described in detail elsewhere herein); (2) maintains a pH of between 5.5-7; and (3) retains at least 97% of the one or more ketorolac compounds and at least 97% of the one or more phenylephrine compounds when stored at about 25° C.+/−2° C. and −60% relative humidity or at accelerated conditions such as 40° C.+/−2° C. and about 75% relative humidity for at least about one month, ≥~2 months, or, e.g., in aspects for ≥~3 months (such as, e.g., ≥~6 months, ≥~12 months, ≥~18 months, or, e.g., ≥~24 months), and wherein the composition(s) further comprise one or more additional ophthalmologically suitable excipients, one or more additional ophthalmologically suitable active pharmaceutical ingredients (APIs), or both. In aspects, such composition(s) can be characterized as core compositions (as described elsewhere herein). In other aspects, such composition(s) can be carrier compositions. In aspects, a core composition may not comprise an additional one or more additional ingredient(s) such as one or more excipient(s) or one or more additional APIs. In aspects, a carrier composition may not comprise an additional one or more additional ingredient(s) such as one or more excipient(s) or one or more additional APIs. In aspects, one or more additional ingredient(s) such as one or more excipient(s), one or more additional active pharmaceutical ingredients (APIs) can be a component of a combined composition, being provided to the composition by the one or more other components of a combined composition of which a core or carrier composition is added to form the combined composition.

In aspects, ophthalmologically suitable compositions, e.g., core compositions and carrier compositions, can comprise an effective amount of one or more pharmaceutically acceptable excipients. In alternative aspects, compositions do not comprise any additional one or more excipients.

A "pharmaceutically acceptable excipient" typically means a pharmaceutically inactive component that is compatible with other ingredients of the formulation (does not cause such other components to be inactivated or unstable, react to form undesirable reactants, etc.), which is not detectably or significantly deleterious to the recipient of the composition, which is formulated in combination with the APIs of the composition, and which typically detectably or significantly improves one or more characteristics of the composition (e.g., delivery, stability, form, distribution of APIs, chemical characteristics of the composition, etc.). The concept of "compatibility" is applicable to any combination of ingredients in a composition of the invention, such as ketorolac compound(s) and phenylephrine compound(s) in association with excipient(s), carrier(s), and the like. In aspects, an excipient can be one or more of a bulking agent, filler, solubilizer, absorption enhancer, chelating agent, antioxidant, tonicity agent, pH-adjusting agent, preservative, thickening agent/viscosity enhancer, carrier, diluent, etc. In aspects, such excipients are suitable for ophthalmological use and present in amounts safe for ophthalmic administration. Compositions of the invention can include any suitable amount of any suitable type(s) of excipients. Particular excipient components/agents that characterize particular aspects of the invention are described in the following sections.

Chelating Agent(s)

In aspects, compositions can comprise one or more pharmaceutically acceptable and ophthalmologically suitable chelating agents. In alternative aspects, compositions do not comprise a chelating agent. In aspects, compositions herein are free of any component that is characterizable as a chelating agent. In aspects, compositions herein are free of any constituent (or any amount of constituent(s)) demonstrating detectable or significant chelating activity(ies).

According to aspects, chelating agent(s) can be present in composition(s) of the invention which detectably or significantly enhance stability, detectably or significantly enhance preservative effectiveness, detectably or significantly reduce the amount of impurities, or any combination thereof. In aspects, the presence of one or more chelating agents provides for composition(s) which is/are stable under room temperature storage conditions, e.g., retains at least ~97% (e.g., ≥97.5%, ≥98%, or ≥~98.5%) of the one or more ketorolac compounds and at least ~97% (e.g., ≥97.5%, ≥98%, or ≥~98.5%) of the one or more phenylephrine compounds when stored at ordinary/standard storage conditions of about 25° C.+/−2° C. and about 60% relative humidity or under accelerated conditions of about 40° C.+/−2° C. and about 75% relative humidity for at least about one month such as ≥~2 months or such as ≥~3 months, ≥~4 months, ≥~5 months, or, e.g., ≥~6 months, such as ≥~9 months, ≥~12 months, ≥~18 months, or ≥~24 months. Any such/similar range of time provided herein also supports aspects directed to stability of a range of time, wherein the end points of such ranges are defined by any of the specifically indicated timepoints (e.g., the preceding sentence supports an embodiment in which the composition has the stability indicated for between 2-24 months, 3-18 months, and 4-12 months, etc.). This point is also explicitly exemplified in certain disclosures provided herein (e.g., in connection with embodiments described in the following paragraph). In aspects, stability of compositions of the invention also or alternatively is established/evidenced by the applicable composition of the invention exhibiting a low level of API-associated impurities for one or both of such API types over similar periods (e.g., having less than 2%, ≤1.5%, ≤1.25%, ≤1% or ≤~0.75%, such as about 0.5% or less impurities over such a time period or range).

For example, composition(s) provided by the invention can comprise chelating agent(s) which detectably improve the stability of the one or more ketorolac compounds, one or more phenylephrine compounds, or both, provide a reduced amount of total impurities over that provided by the same composition lacking a chelating agent, provide a reduced amount of one or more specific impurities over that provided by the same composition lacking a chelating agent (e.g., a significantly reduced amount of such an impurity as compared to, e.g., a composition having the formulation of OMIDRIA or a reference product or a level of impurities that is at least about the same, or at least not substantially inferior to, a composition in the OMIDRIA formulation or a reference product), enhance preservative effectiveness, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more (e.g., 3-36 months, 2-24 months, 3-24 months, 4-24 months, 4-36 months, 6-24 months, 6-36 months, 12-36 months, 18-36 months, 18-24 months, 12-60 months, 12-48 months, or ≥12, ≥18, ≥24, ≥30, or ≥36 months).

In aspects, the invention provides composition(s) comprising one or more pharmaceutically acceptable and ophthalmologically suitable chelating agents capable of sequestering divalent or polyvalent metal cations, effective at pH range of between, e.g., ~5.0-~8.0, such as between ~5.0-~7.0, e.g., ~5.5-~7.0, or, e.g., ~6.0-~7.0. In aspects, a chelating agent of the composition(s) herein do not detectably or significantly negatively impact any other component of the formulation, such as, e.g., they do not detectably or significantly reduce the efficacy of any one or more ketorolac compounds, phenylephrine compounds (e.g., reduce anti-inflammatory effect or mydriatic effect), or any other API or excipient present or which may be present in the composition.

In aspects any ophthalmologically suitable and pharmaceutically acceptable chelating agent can be used. In aspects, exemplary chelating agents present in a composition described herein can comprise, e.g., cromolyn, monomeric polyacids such as EDTA, cyclohexanediamine tetraacetic acid (CDTA), hydroxyethylethylenediaminetriacetic acid (HEDTA), diethylenetriaminepentaacetic acid (DTPA), dimercaptopropane sulfonic acid (DMPS), dimercaptosuccinic acid (DMSA), aminotrimethylene phosphonic acid (ATPA); suitable and effective derivatives or analogs of any thereof or other related compounds (as exemplified with respect to other variant compounds of APIs discussed elsewhere); any ophthalmologically acceptable salts thereof, and/or combinations of any two or more such compounds. In other aspects, a chelating agent can be a phosphate, e.g., pyrophosphates, tripolyphosphates, and, hexametaphosphates; a chelating antibiotic such as chloroquine and tetracycline; a nitrogen-containing chelating agent containing ≥2 chelating nitrogen atoms within an imino group or in an aromatic ring (e.g., diimines, 2,2'-bipyridines, etc.); or e.g., a polyamine such as cyclam (1,4,7,11-tetraazacyclotetradecane), N—(C1-C30 alkyl)-substituted cyclams (e.g., hexadecyclam, tetramethyl hexadecyl cyclam), diethylenetriamine (DETA), spermine, diethylnorspermine (DENSPM), diethylhomospermine (DEHOP), and deferoxamine (N'-[5-[[4-[[5-(acetylhydroxyamino) pentyl] amino]-1,4-dioxobutyl]hydroxy-amino]pentyl]-N'-(5-aminopentyl)-N-hydroxybutanediamide; AKA desferrioxamine B and DFO).

In aspects, composition(s) provided by the invention comprise one or more pharmaceutically acceptable and ophthalmologically suitable chelating agents characterizable as a monomeric polyacid. In aspects, the chelating agent comprises an ethylenediaminetetraacetic acid (EDTA) compound or an ophthalmologically suitable EDTA salt such as, e.g., diammonium EDTA, disodium EDTA, dipotassium EDTA, triammonium EDTA, trisodium EDTA, tripotassium EDTA, or calcium disodium EDTA.

In aspects, one or more chelating agents can be present in composition(s) provided by the invention in an amount representing between about 0.001 wt/v. %-about 0.5 wt/v. % of the composition, such as, e.g., ~0.001 wt/v. %-~0.4 wt/v. %, ~0.001 wt/v. %-~0.3 wt/v. %, ~0.001 wt/v. %-~0.2 wt/v. %, or 0.001 wt/v. %-~0.1 wt/v. %, e.g., such as, e.g., 0.005 wt/v. %-~0.5 wt/v. %, 0.01 wt/v. %-~0.5 wt/v. %, 0.02 wt/v. %-~0.5 wt/v. %, 0.03 wt/v. %-~0.5 wt/v. %, or 0.04 wt/v. %-~0.5 wt/v. %, e.g., ~0.01 wt/v. %-~0.2 wt/v. %, ~0.02 wt/v. %-~0.2 wt/v. %, ~0.05 wt/v. %-~0.2 w/v %, ~0.07 wt/v. %-~0.2 wt/v. %, ~0.09 wt/v. %-~0.2 wt/v. %, such as, e.g., ~0.05 wt/v. %-~0.17 wt/v. %, ~0.05 wt/v. %-~0.15 wt/v. %, or, e.g., in a specific aspect, ~0.1 wt/v. % of the composition. According to one specific aspect, composition(s) provided by the invention comprise an EDTA compound or salt thereof in an amount of about 0.1 wt/v. %.

In aspects, compositions herein are free of an EDTA compound or EDTA salt.

In this and any other ingredient aspect of the invention, the invention also can be characterized as providing compositions comprising a "means" for providing a recited function, e.g., here imparting/providing an effective, detectable, or significant chelating effect of compositions (e.g., forming stable water-soluble complexes (chelates) with alkaline earth and heavy metal ions or known equivalents of either or both thereof). In such a respect, any known equivalents of named agents/elements provided herein can also be, e.g., are, incorporated into the applicable compositions or methods of the invention (in the case of methods, such embodiments can be described as a "step for" achieving a recited function). As with other sections similarly described herein, any of the components of the invention can be, where suitable, described as "means" elements. E.g., the above-described chelating agents/compounds or components can be described as "chelation means" or "means for providing effective, detectable, or significant chelation activity/characteristics" to the composition or constituent(s) of the composition.

Ketorolac+Phenylephrine+EDTA

In aspects, the invention provides an ophthalmologically suitable composition (e.g., ophthalmologically suitable core composition or ophthalmologically suitable carrier composition) for use in treating or preventing one or more ophthalmic conditions, diseases, or for use in related procedures, comprising pharmaceutically acceptable amounts of each of one or more ketorolac compounds and one or more phenylephrine compounds, and further comprising an effective amount of an EDTA compound or salt thereof, wherein, in aspects, the composition optionally further (1) lacks a buffer component (e.g., a buffer component as described herein); (2) maintains a pH of between 5.5-7; or (3) retains at least 97% of the one or more ketorolac compounds and at least 97% of the one or more phenylephrine compounds (e.g., ≥~97.5%, ≥~98%, ≥~98.5%, ≥~99%, ≥~99.5% or more) when stored at about 25° C.+/−2° C. and about 60% relative humidity or at about 40° C.+/−2° C. and about 75% relative humidity for at least about one month, such as, e.g., at least about 2, ≥~3 months, ≥~4 months, ≥~5 months, ≥~6 months, ≥~12 months, ≥~18 months, ≥~24 months, or more. In aspects, such compositions comprise between about 0.05 wt/v. %-about 0.5 wt/v. % of an EDTA compound or salt thereof. In aspects, the incorporation of a chelating agent, such as, for example, the incorporation of an EDTA compound or salt thereof, can detectably or significantly extend the length of time over which the level of total impurities remains below 0.5% (e.g., remain at pharmaceutically acceptable levels).

pH Adjusting Agent(s)

In aspects, the pH of the composition(s) provided by the invention can be adjusted using one or more pharmaceutically acceptable and ophthalmologically suitable pH adjusting agent(s). In aspects, composition(s) provided by the invention can comprise one or more suitable pH adjusting agent(s). In alternative aspects, compositions do not comprise any component that is a pH adjusting agent. In aspects any pH adjustment to the composition or ingredients thereof is made only during the manufacturing process.

Herein, a "pH adjusting agent" is generally understood to be a suitable acidifying or alkalizing agent used to detectably or significantly lower or raise the pH of the composition to a target value. In aspects, most or all of the pH adjusting agent(s) in the composition or used in the manufacturing process is an agent (or are agents) which, alone, is/are incapable of providing/imparting a buffering capacity to the composition. In aspects, a pH adjusting agent ingredient or element used in manufacturing is not accompanied by (is free of or free of any significant amount of) a corresponding acid or base to provide a buffering capacity to the composition. In aspects, an acidifying pH adjusting agent can be present to lower the pH, while an alkalizing agent can be present to raise the pH to a target level. In aspects, an acidifying agent can be characterizable as a strong acid. In aspects, an alkalizing agent can be characterizable as a strong base. In aspects, a pH adjusting agent is added during the manufacturing process of the composition(s) to adjust the pH of the composition prior to final packaging.

According to aspects, one or more pH adjusting agents can be present in composition(s) of the invention in an amount and of a nature of which provide the resulting (typically dosage ready/storage ready/final) composition with a pH of between about 5.0-8.0, such as, e.g., between ~5.0-~7.8, −5.0-~7.6, −5.0-~7.4, −5.0-~7.2, or ~5.0-~7.0, e.g., ~5.2-~8, −5.4-~8, −5.6-~8, −5.8-~8, −6-~8, or ~6.2-~8, such as, e.g., ~5.2-~7.8, ~5.4-~7.6, ~5.6-~7.4, ~5.8-~7.2, −6-~7, or ~6.2-~6.8, such as, e.g., ~5.5-~7.5, ~5.4-~6.9, ~5.6-~6.8, ~5.7-~7.3, ~5.8-~6.6, ~5.9-~7.1, ~6.0-~6.6, ~6.1-~6.9, ~6.1-~6.9, ~6.2-~6.4, or, e.g., in specific aspects, a pH of ~6.3. E.g., in aspects pH adjusting agent(s) are responsible for achieving such a pH, as reflected by the composition otherwise having a detectably or significantly different pH prior to the addition of the pH adjusting agent(s). In case(s), the pH adjusting agents are only necessary some of the time, e.g., most of the time, or generally all of the time, to achieve such an indicated pH. In aspects, pH adjusting agent(s) of the composition(s) herein do not detectably or significantly negatively impact any other component of the formulation, such as, e.g., they do not detectably or significantly reduce the efficacy of any one or more ketorolac compounds, phenylephrine compounds (e.g., reduce anti-inflammatory effect or mydriatic effect), or any other API or excipient present in a composition.

In aspects any ophthalmologically suitable pH adjusting agent can be used in compositions/methods. In aspects, exemplary pH adjusting agent(s) in a composition described herein can comprise, any suitable pH adjusting agents commonly used and known in the art, such as, e.g., an acid such as a strong acid or, e.g., a base such as a strong base. In aspects, a pH adjusting agent can be, e.g., mineral acids such as sodium hydroxide hydrochloric acid (HCl) or sodium hydroxide (NaOH), such as, for example, ~1N HCl or ~1N NaOH (1N being the concentration of the agent added to the composition(s) to adjust the pH of the composition(s)).

In aspects, pH adjusting agent(s) can be present in the compositions in an amount effective in providing the target pH. In aspects, such an amount can be considered a "trace amount," e.g., less than ~0.005 wt/v. %, <~0.004 wt/v. %, <~0.003 wt/v. %, <~0.002 wt/v. %, e.g., <~0.001 wt/v. %. In aspects, such an amount can be an amount representing between about 0-about 0.01 wt/v. %. In aspects, one or more pH adjusting agent(s) can be present in the compositions provided by the invention in an amount effective in providing the target pH, such amounts representing between about 0-about 0.1 wt/v. %, such as, e.g., about 0.0001 wt/v. %, 0.005 wt/v. %, 0.001 w/v %, 0.015 wt/v. %, 0.01 wt/v. %, ~0.02 wt/v. %, ~0.03 wt/v. %, ~0.04 wt/v. %, ~0.05 wt/v. %, ~0.06 wt/v. %, ~0.07 wt/v. %, ~0.08 wt/v. %, or, e.g., ~0.09 wt/v. %.

In this and any other ingredient aspect of the invention, the invention also can be characterized as comprising a "means" for providing a recited function, here imparting/providing an effective, detectable, or significant pH adjustment effect (e.g., pH establishment) to/of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described pH adjusting agents/compounds or components can be described as pH adjusting means or means for providing effective, detectable, or significant pH adjustment activity/characteristics to the composition). In such aspects, it is understood that known equivalents to the recited elements provided herein also can be utilized/present in the place of such specifically named elements.

Antioxidant(s)

In aspects, compositions comprise ophthalmologically suitable antioxidant(s). In alternative aspects, compositions do not comprise any component characterizable as an antioxidant. In aspects, compositions do not comprise a component (constituent) characterizable as an antioxidant. In aspects, compositions do not comprise a component (constituent) demonstrating detectable or significant antioxidant activity(ies).

An "antioxidant" is typically understood as referring to a substance that preferentially reacts with oxygen, thereby detectably or significantly protecting other components of a composition to which it is added from premature degradation due to oxidation (e.g., protecting APIs that is known to be detectably/significantly susceptible to oxidation).

According to aspects, one or more antioxidant compounds can be present in composition(s) of the invention which detectably or significantly improve API stability or reduce the amount of impurities, such as, e.g., providing for a composition which is stable under room temperature storage conditions, e.g., retains at least 97% of the one or more ketorolac compounds and at least 97% of the one or more phenylephrine compounds when stored at about 25° C.+/−2° C. and about 60% relative humidity or under accelerated conditions of ~40° C.+/−2° C. and about 75% relative humidity for at least about ~1 month, e.g., ≥~2 months or such as ≥~3 months, ≥~4 months, ≥~5 months, or, e.g., ≥~6 months, such as ≥~12, ≥~18, or ≥~24 months.

Composition(s) can comprise antioxidant(s) which DOS improve the stability of ketorolac compound(s) or phenylephrine compound(s), reduces the amount of impurities (e.g., total impurities or one or more individual impurities), enhances preservative effectiveness, or achieves/causes any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or for even longer periods (e.g., 3-24, 3-18, 3-12, 3-36, 4-12, 4-24, 4-36, 6-12, 6-18, 6-24, or 6-36 months).

In aspects, the invention provides composition(s) comprising one or more pharmaceutically acceptable and ophthalmologically suitable antioxidant agents effective at pH range of between, e.g., ~5.0-~8.0, such as between ~5.0-~7.0, e.g., ~5.5-~7.0, or, e.g., ~6.0-~7.0. In aspects, antioxidant compound(s) of the composition(s) herein do not detectably or significantly negatively impact any other component of the formulation, such as, e.g., they do not detectably or significantly reduce the efficacy of any one or more ketorolac compounds, phenylephrine compounds (e.g., reduce anti-inflammatory effect or mydriatic effect), or any other API or excipient present or which may be present in the composition.

In aspects any ophthalmologically/pharmaceutically acceptable antioxidant(s) can be used in methods/compositions, in any suitable effective amount(s). In aspects, exemplary antioxidant(s) in a composition described herein can comprise, e.g., sodium ascorbate, ascorbic acid, thiamine, pyridoxine, histidine, cysteine, glutathione, sodium bisulphite, sodium sulphite, sodium metabisulphite, sodium thiosulphite, sodium formaldehyde sulphoxylate, acetylcysteine, cysteine, thioglycerol, thioglycollic acid, thiolactic acid, thieurea, dihithreitol, propyl gallate, butylated hydroxyanisole, butylated hydroxytoluene, tertiary butyl hydroquinone, ascorbyl palmitate, nordihydroguaiaretic acid and alpha-tocopherol, any ophthalmologically acceptable salts thereof, or combinations of any two or more such compounds.

In aspects, antioxidant compound(s)/agent(s) can be present in compositions in an amount representing 0.001 wt/v. %-about 2 wt/v. % of the composition, such as, e.g., ~0.001 wt/v. %-~1.8 wt/v. %, ~0.001 wt/v. %-~1.6 wt/v. %, ~0.001 wt/v. %-~1.4 wt/v. %, ~0.001 wt/v. %-~1.2 wt/v. %, or ~0.001 wt/v. %-~1 wt/v. %, such as, e.g., 0.01 wt/v. %-~2 wt/v. %, 0.05 wt/v. %-~2 wt/v. %, 0.1 wt/v. %-~2 wt/v. %, 0.2 wt/v. %-~2 wt/v. %, 0.4 wt/v. %-~2 wt/v. %, 0.6 wt/v. %-~2 wt/v. %, 0.8 wt/v. %-~2 wt/v. %, or 1 wt/v. %-~2 wt/v. %, e.g., ~0.01 wt/v. %-~1.5 wt/v. %, ~0.08 wt/v. %-~1 wt/v. %, or. e.g., ~0.05 wt/v. %-~1 wt/v. % of the composition.

Aspects can comprise a "means" for providing a recited function, e.g., here imparting/providing an effective, detectable, or significant antioxidant effect to/of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described antioxidant agents/compounds or components can be described as antioxidant means or means for providing effective, detectable, or significant antioxidant activity/characteristics to the composition.)

Tonicity Agent(s)

In aspects, compositions comprise pharmaceutically acceptable/ophthalmologically suitable tonicity agent(s). In alternative aspects, compositions do not comprise any component(s) characterizable as a tonicity agent (or any significant/effective amount thereof). In aspects, composition(s) do not comprise any component/constituent capable of demonstrating tonicity-adjusting property(ies). A "tonicity agent" is understood in the art to typically mean a substance used in the ophthalmic compositions to effectively adjust the composition of the formulation to be within a desired isotonic range, e.g., be characterizable as being having an osmolality within a defined range, e.g., a range as provided below.

According to aspects, one or more tonicity agents can be present in composition(s) of the invention which detectably or significantly reduce irritability or increase tolerability of the ophthalmic composition(s) over the same composition lacking such a tonicity agent or having a significantly different osmolality. In aspects, inclusion of a tonicity agent can provide a tonicity of the composition rendering a composition tolerable (e.g., lacking clinically significant irritation or damage) by a recipient/recipient eye when provided as a carrier composition or when the composition is provided as a combination composition.

In cases, compositions have an osmolality between about 200-about 400 mOsm/Kg, such as, e.g., ~210-390 mOsm/Kg, ~220-~380 mOsm/Kg, ~230-~370 mOsm/Kg, ~240-~360 mOsm/Kg, or, e.g., between about 250 to about 350 mOsm/kg.

In aspects, tonicity agent(s) of the composition(s) herein do not detectably or significantly negatively impact any other component of the formulation, such as, e.g., they do not detectably or significantly reduce the efficacy of any one or more ketorolac compounds, phenylephrine compounds (e.g., reduce anti-inflammatory effect or mydriatic effect), or any other API or excipient present or which may be present in the composition.

In facets, any ophthalmologically/pharmaceutically acceptable tonicity agent(s) can be included in compositions. Exemplary tonicity agent(s) include glycerin, mannitol, sorbitol, sodium chloride, and other electrolytes, or combinations of any ≥2 of such compounds.

In aspects, one or more tonicity agent(s) can be present in the compositions in an amount representing between about 0.001 wt/v. %-about 1.4 wt/v. % of the composition, such as, e.g., ~0.08 wt/v. %-~1.2 wt/v. %, ~0.06 wt/v. %-~1 wt/v. %, ~0.04 wt/v. %-~0.9 wt/v. %, or, e.g., between ~0.01 wt/v. %-~0.8 wt/v. % of the composition.

The invention provides compositions including means for imparting/providing an effective, detectable, or tonicity effect (e.g., establishment of a target osmolality or osmolality range). In such a respect, any known equivalents of the named agents provided here can also be, e.g., are, incorporated into compositions or methods. Such agents and equivalents can be characterized as tonicity means or means for providing tonicity characteristics.

Preservation Agent(s)

In aspects, compositions can comprise one or more pharmaceutically acceptable and ophthalmologically suitable preservation agent(s) ("preservatives"). In alternative aspects, compositions do not comprise a preservative, e.g., any component or constituent capable of demonstrating one or more preservation properties, such that the composition(s) provided by the invention are characterizable as "preservative free." In aspects, compositions lack any significant amount of any agent that is solely/primarily characterizable as a preservative or that is at all characterized as a preservative. Any aspect described as being "free" of a component simultaneously implicitly provides such "low" amount compositions of the ingredient/component in question.

In aspects, a "preservative" typically is understood to be a compound/composition which detectably or significantly enhances stability of the composition(s), such as the stability of the one or more ketorolac compounds, one or more phenylephrine compounds, reduces the number(s)/amount(s) of detectable/significant impurities (e.g., total impurities or one or more specific impurities) over the course of a storage under room temperature or accelerated storage conditions, detectably or significantly reduce antimicrobial activity, or any combination of any or all thereof. In aspects, one or more preservative(s) can be present in composition(s) of the invention which detectably or significantly enhance stability of the composition(s), such as the stability of the one or more ketorolac compounds, one or more phenylephrine compounds, reduces the amount of impurities, or any combination of any or all thereof, such as providing for a composition which is stable under room temperature storage conditions, e.g., providing for compositions which can retain at least 97% of the one or more ketorolac compounds and at least 97% of the one or more phenylephrine compounds when stored at about 25° C.+/−2° C. and about 60% relative humidity or at accelerated conditions of about 40° C.+/−2° C. and about 75% relative humidity for at least about one month such as ≥~2 months or such as ≥~3 months (e.g., ≥~6, ≥~9, ≥~12, ≥~18, or ≥~24 months). In aspects, compositions can comprise preservative(s) in anti-microbially effective amount(s) which can DOS inhibit microbial growth.

In aspects, an "antimicrobial effective amount" of a preservative can be determined by performing preservative efficacy tests or antimicrobial effectiveness tests known in the art. In aspects, such tests are described in, e.g., chapter 51 of the U.S. Pharmacopoeia 29-National Formulary 24 (USP 29-NF 24). In aspects, composition(s) provided by the invention can comprise one or more preservatives in an amount within the concentration ranges described in one or more standard reference books such as the most recent edition of Remington's Pharmaceutical Sciences, Handbook of Pharmaceutical Excipients $5^{th}$ ed. or $6^{th}$ ed., or Handbook of Pharmaceutical Excipients ($9^{th}$ ed.), Sheskey et al. (ISBN 9780 85711 375 7) (2020).

Composition(s) provided by the invention can comprise one or more preservatives which detectably or significantly improve the stability of the one or more ketorolac compounds or one or more phenylephrine compounds, enhances preservative effectiveness, prevent detectable or significant anti-microbial growth, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more (e.g., about 3-36 months, about 6-36 months, about 4-36 months, about 18-~36 months, about 12-24 months, about 6-24 months, or about 12-36 months).

In aspects, the invention provides composition(s) comprising pharmaceutically acceptable and ophthalmologically suitable preservative(s) effective (e.g., capable of demonstrating one or more of the characteristics of a preservative described above in the context of a composition of the invention) at pH range of between, e.g., ~5.0-~8.0, such as between ~5.0-~7.0, e.g., ~5.5-~7.0, or, e.g., ~6.0-~7.0. In aspects, a preservative of the composition(s) herein does not detectably or significantly negatively impact any other component of the formulation, such as, e.g., they do not detectably or significantly reduce the efficacy or functionality of any one or more ketorolac compounds, phenylephrine compounds (e.g., reduce anti-inflammatory effect or mydriatic effect), or any other API or excipient present or which may be present in the composition.

In aspects any ophthalmologically suitable and pharmaceutically acceptable preservative can be used. In aspects, exemplary preservative(s) present in a composition described herein can comprise effective amount(s) of, e.g., hydrogen peroxide; sorbic acid; biguanides; quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; and thiomersal, etc., or any ophthalmologically acceptable salts thereof, or combinations of any two or more such compounds, or equivalents thereof.

In aspects, composition(s) provided by the invention can comprise one or more quaternary ammonium compounds, such as, e.g., benzalkonium chlorides (abbreviated herein as BKC, and which is often abbreviated in the art as BAC, BAK, or BZK). Benzalkonium chlorides may also be referred to as alkyl dimethyl benzyl ammonium chlorides (ADBAC), alkyl dimethyl (phenylmethyl) chlorides, or ammonium alkyl dimethyl benzyl chlorides. In aspects, BKC can serve as a penetration enhancer, preservative, solubilizer, or any combination thereof. That is, in aspects, BKC can provide a detectable or significant increase in the penetration, e.g., the bioavailability, of any one or more ketorolac compounds, phenylephrine compounds, or both, can provide preservation qualities such as those described in this section or in the art, or, e.g., can detectably or significantly improve upon the solubilization of any one or more APIs, such as any one or more ketorolac or phenylephrine compounds.

In aspects, preservative(s), such as BKC, can be present in compositions in about 0.001 wt/v. %-about 0.05 wt/v. % of the composition, such as, e.g., ~0.01 wt/v. %-~0.05 wt/v. %, ~0.01 wt/v. %-~0.04 wt/v. %, ~0.01 wt/v. %-~0.03 wt/v. %, or, e.g., in a specific aspect, ~0.02 wt/v. % of the composition. In aspects, composition(s) provided by the invention comprise BKC in an amount of about 0.02 wt/v. %. In aspects, compositions herein are free of BKC.

In this and any other ingredient aspect of the invention, the invention also can be characterized as comprising a "means" for providing a recited function, here imparting/providing an effective, detectable, or significant preservation effect (e.g., increased stability of one or more constituents of the composition, maintenance of an acceptable level of impurities during composition storage, increased composition shelf life, etc.) of compositions. In such a respect, any known equivalents of such named agents can also be, e.g., are, incorporated into compositions or methods of the invention. As with other sections similarly described herein, any of the components of the invention can be, where suitable, described as means (e.g., the above-described preservation agents/compounds or components can be described as preservation means or means for providing effective, detectable, or significant preservation activity/characteristics to the composition or one or more constituents of the composition.)

Carrier(s)

In aspects, compositions can comprise one or more pharmaceutically acceptable and ophthalmologically suitable carriers. In alternative aspects, compositions do not comprise a carrier. In cases, a core composition can be a solid composition, e.g., a dried powder (such as a lyophilized) composition, such that it requires reconstitution or is adapted to be reconstituted prior to use. In aspects, a core composition is not suitable for administration to an eye without reconstitution. In aspects, carrier compositions are core compositions plus a carrier.

In aspects, a core composition is reconstituted with or is initially formulated with a carrier component/material, which can be a single ingredient or a composition comprising multiple ingredients. In aspects, a carrier is a fluid, e.g., a liquid, and, in aspects, a composition comprising a carrier is a liquid composition, such as a solution. In aspects, a carrier composition can be administered directly to the eye. In aspects, composition(s) are typically provided as carrier composition(s), and in aspects are further added to existing formulations (e.g., to an existing irrigation solution such that the carrier composition is further diluted prior to use) to provide a combination composition which is then administered to an eye.

According to aspects, carrier(s) are present in a sufficient amount to deliver the effective amounts of API(s) and, if present, one or more excipients, to intended targets.

In aspects, the invention provides for a carrier composition wherein the carrier of the carrier composition does not detectably or significantly adversely affect the stability of the composition, efficacy of the composition, or compatibility of ingredients of the composition, etc., at a period of at least about 2 weeks, e.g., ≥~1 month, ≥~6 weeks, ≥~2 months, ≥~10 weeks, ≥~3 months, ≥~14 weeks, ≥~4 months, ≥~18 weeks, ≥~5 months, ≥~22 months, ≥~6 months, or even longer (e.g., ~2-~36 months, ~6-~36 months, ~12-~24 months, or more, or similar ranges provided with respect to other ingredients/compositions described herein, etc.).

In aspects, a carrier is a pharmaceutically/ophthalmologically suitable carrier capable of serving as a carrier of a composition having a pH of, e.g., between about ~5.0-~8.0, such as between ~5.0-~7.0, e.g., ~5.5-~7.0, ~6.0-~7.0, ~6.0-~6.6, or, e.g., about 6.3. In aspects, the carrier, and further, the carrier composition, does not have a pH lower than about 5.0. In aspects, a carrier of the composition(s) herein does not detectably or significantly negatively impact any other component of the formulation, such as, e.g., a carrier does not detectably or significantly reduce the efficacy of any one or more ketorolac compounds, phenylephrine compounds (e.g., reduce anti-inflammatory effect or mydriatic effect), or any other API or excipient present in the composition.

In aspects any ophthalmologically acceptable carrier is used as a component of a composition (or to form a composition). Exemplary carriers comprise, e.g., a lipid carrier, a gel carrier, an oil-based carrier, an emulsion carrier, an emulsifier-containing carrier that forms an emulsion when mixed with other components, or, a solution carrier, e.g., an aqueous solution carrier. In aspects, the carrier is an aqueous carrier. In aspects, the carrier is mostly, generally only, essentially only, substantially only, or only composed of water for injection (WFI) (a sterile, solute-free preparation of distilled water). In alternative aspects, other pharmaceutically acceptable and ophthalmologically suitable aqueous carriers which do not adversely affect the stability of the composition(s) may be used, such as, e.g., deionized water.

According to aspects, the carrier does not comprise any detectable, significant, or intentionally added amount of any deuterated carrier or, in aspects, any deuteration, e.g., the carrier can mostly, generally, or only comprise non-deuterated water or otherwise lack any deuterated carriers, other excipients, or components in general.

In aspects, a carrier can be present in an amount representing at least about 50 w/v %, ≥~55 w/v %, ≥~60 w/v %, ≥~65 w/v %, ≥~70 w/v %, ≥~75 w/v %, ≥~80 w/v %, ≥~85 w/v %, ≥~90 w/v %, ≥~95 w/v %, ≥~97 w/v %, ≥~98 w/v %, or ≥~99 w/v % of the composition.

In aspects, compositions comprise a means for imparting/providing an effective, detectable, or significant carrier function for/of a composition. In such a respect, any known equivalents of such named agents can also be, e.g., are, incorporated into compositions or methods of the invention.

Other Excipient(s)

In aspects, compositions can comprise other excipients(s) in addition to or in place of any of the type(s) of excipients described above. In aspects, such an "other" excipient can be any excipient which does not DOS negatively impact the efficacy, safety, performance, etc. of any API(s) in the composition (e.g., any one or more phenylephrine compounds, any one or more ketorolac compounds, or both), and which further does not detectably or significantly negatively impact any one or more other excipients in the composition(s). Such other excipients can be, e.g., one or more penetration enhancers, one or more solubilizers, one or more demulcents, one or more viscosity enhancers, or one or more components which provide detectable or significant properties of two or more such excipients (e.g., a solubilizer which can further provide demulcent effect, etc. or solubilization and penetration effect, etc.)

Additional APIs (or Lack Thereof)

In facets, compositions comprise ketorolac compound(s), e.g., ketorolac tromethamine, phenylephrine compound(s), e.g., phenylephrine HCl, and no detectable or significant amounts of any additional active pharmaceutical ingredients (APIs). In aspects, compositions comprise ≥1 API(s) in addition to ketorolac and phenylephrine compounds.

According to aspects, compositions include a suitable core composition or carrier composition) for use in treating or preventing ophthalmic conditions, diseases, or for use in related procedures, comprising pharmaceutically acceptable amounts of each of one or more ketorolac compounds, e.g., ketorolac tromethamine, and one or more phenylephrine compounds, e.g., phenylephrine HCl, wherein the composition (1) lacks a buffer component wherein (a) a buffer is a combination of a weak base and its conjugate acid, a weak acid and its conjugate base, or both; (b) wherein the acid and base pairs of a buffer component are present in concentrations of within 10× of one another (i.e., are defined as a pair of agents present in a ratio of ≤1:10, such as 1:9, 1:8, 1:7, etc.); (c) wherein the pKa of a buffer component is between 4.3-8.3, such as the pKa of any such buffer component is between 5.3-7.3, e.g., between about 6.0 and 6.6; or (d) wherein, when the ophthalmologically suitable composition is at a pH of about 6.3, the acid and base pairs of a buffer component prevents a change in pH of the composition of more than 2% (e.g., more than 1.5% or more than 1%) when 0.1 moles of HCl or 0.1 moles of NaOH are added to 1 L of the composition; or (e) any combination of two or more of (a)-(d); (2) maintains a pH of between 5.5-7 (e.g., the composition has a pH of about 5.4 or about 5.5); and (3) retains at least 97% of the one or more ketorolac compounds and at least 97% of the one or more phenylephrine compounds when stored at 25° C.+/−2° C. for at least about one month (e.g., the composition maintains ≥98% of a ketorolac salt and ≥98% phenylephrine HCl under such conditions for ≥2, ≥3, ≥6, ≥12, ≥18, ≥24, ≥30, or ≥36 months), and further wherein (4) the composition comprises an effective and suitable amount of at least one additional API.

According to aspects, compositions can comprise one or more additional pharmaceutically acceptable and ophthalmologically acceptable APIs in addition to the one or more ketorolac compound(s) and the one or more phenylephrine compound(s) in any effective amount which provides for the API to impart the desired effect. In aspects, an additional API can be present in an amount effective in detectably or significantly increasing the efficacy of the ketorolac compound, detectably or significantly increasing the efficacy of the phenylephrine compound, or detectably or significantly increasing the therapeutic usefulness or clinical efficacy of the composition, e.g., demonstrating a detectable or significant beneficial effect in the recipient of the composition. In aspects, additional API(s) can provide a detectable or significant increase in anti-inflammatory strength or activity of the composition. In aspects, the one or more additional APIs can provide a detectable or significant increase in the mydriatic strength or activity of the composition. In aspects, additional API(s) can provide a DOS effect, e.g., a clinically significant effect, different from anti-inflammatory or mydriatic activity (such as, e.g., an antimicrobial effect or other ophthalmologically suitable or beneficial effect, such as an effect which may be helpful for a particular application in which the composition may be useful, such as, e.g., an analgesic or pain reducing effect).

In aspects, composition(s) can comprise one or more additional APIs in addition to the one or more ketorolac compounds and the one or more phenylephrine compounds, wherein the one or more additional APIs are stable within the composition(s) at a pH of between, e.g., ~5.0-~8.0, such as between ~5.0-~7.0, e.g., ~5.5-~7.0, or, e.g., ~6.0-~7.0 for a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or more (e.g., ≥~12, ≥~18, or ≥~24 months).

In aspects, some, most, generally all, or all additional API(s) do not detectably or significantly negatively impact any other component of the formulation, such as, e.g., they do not detectably or significantly reduce the efficacy of any one or more ketorolac compounds, phenylephrine compounds (e.g., reduce anti-inflammatory effect or mydriatic effect), or any other API or excipient present or which may be present in the composition.

In aspects any acceptable additional API can be incorporated in compositions/methods. In aspects, additional APIs can comprise, e.g., steroidal anti-inflammatory agent(s), non-steroidal anti-inflammatory (NSAID) agent, antibacterial/antibiotic, synthetic antibacterial, antifungal agent(s), synthetic antifungal, antineoplastic agent, anti-allergic agent, glaucoma-treating agent, antiviral agent, anti-mycotic agent, intraocular pressure reducing agent, glaucoma-treating agent, pain reduction agent(s), etc., which are not ketorolac compound(s) or phenylephrine compound(s). Specific exemplary APIs are described elsewhere.

Antiinflammatory Agent(s)

In one aspect, the invention provides compositions comprising ketorolac and phenylephrine compounds, (e.g., ketorolac tromethamine and phenylephrine HCl) and steroid anti-inflammatory agent(s). Suitable steroid anti-inflammatory agents that can be incorporated in compositions can be any pharmaceutically/ophthalmologically suitable steroid anti-inflammatory agent(s). In aspects, steroid anti-inflammatory agents suitable for combination therapy are, e.g., 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and, e.g., triamcinolone hexacetonide, and pharmaceutically acceptable salts thereof, and suitable mixtures of any or all thereof.

In aspects, steroid anti-inflammatory agent(s) is/are present in an amount which detectably or significantly increases the ability of the composition to exert a clinically relevant anti-inflammatory effect, such as increasing the anti-inflammatory effect of the composition by at least about 1%, ~2%, ~3%, ~5%, ~10%, ~15%, ~20%, ~25%, ~30%, ~35%, ~40%, ~45%, or at least ~50% (e.g., 5-200%, 10-250%, 25-250%, 25-100%, 33-100%, 15-75%, or 25-75%) over the same composition without the additional steroid anti-inflammatory agent(s).

In one aspect, compositions comprising ketorolac compound(s), phenylephrine compound(s), and NSAID(s) are provided. A suitable NSAID for compositions can be any pharmaceutically/ophthalmologically suitable NSAID. Suitable NSAIDs for combination therapy/compositions include, e.g., aspirin, benoxaprofen, benzofenac, bucloxic acid, butibufen, carprofen, cicloprofen, cinmetacin, clidanac, clopirac, diclofenac, diflupredinate, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketroprofen, lactorolac, lonazolac, metiazinic, miroprofen, nepafenac, naproxen, norketotifen, oxaprozin, oxepinac, phenacetin, pirprofen, pirazolac, protizinic acid, sulindac, suprofen, tiaprofenic acid, tolmetin, and, e.g., zomepirac, acceptable salts thereof, and mixtures of any/all thereof.

In aspects, additional NSAID anti-inflammatory agent(s) is/are present in an amount which detectably or significantly increases the ability of the composition to exert a DOS clinically relevant anti-inflammatory effect, e.g., increasing the anti-inflammatory effect of the composition by at least about 1%, ~2%, ~3%, ~5%, ~10%, ~15%, ~20%, ~25%, ~30%, ~35%, ~40%, ~45%, or at least 50% over a substantially identical composition (without the NSAID(s)).

In aspects, compositions comprise means for imparting/providing an effective, detectable, or significant antiinflammatory effect to/of composition(s). which in addition to any named agents herein can or alternatively include any known equivalents thereof.

Antimicrobial Agent(s)

In one aspect, the invention provides compositions comprising one or more ketorolac compounds, one or more phenylephrine compounds, (e.g., ketorolac tromethamine and phenylephrine HCl) and one or more antimicrobials, e.g., one or more antibiotics. In aspects, suitable antibacterial/antibiotics can be any pharmaceutically acceptable and ophthalmologically suitable antibacterial/antibiotic. In aspects, suitable antibacterial/antibiotics for combination therapy are, for example, aminoglycosides for example amikacin, apramycin, arbekacin, bambermycins, butirosin, dibekacin, dihydrostreptomycin, fortimicin(s), gentamicin, tobramycin, isepamicin, kanamycin, micronomicin, neomycin, neomycin undecylenate, netilmicin, paromomycin, ribostamycin, sisomicin, spectinomycin, streptomycin, trospectomycin; amphenicois for example azidamfenicol, chloramphenicol, florfenicol, thiamphenicol), ansamycins (e.g., rifamide, rifampin, rifamycin sv, rifapentine, rifaximin; beta-lactams for example carbacephems include loracarbef; carbapenems for example biapenem, imipenem, meropenem, panipenem; cephalosporins for example cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, cefloranide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, ceifuzonam, cephacetrile sodium, cephalexin, cephaloglycin, cephaloridine, cephalosporin, cephalothin, cephapirin sodium, cephradine, pivcefalexin; cephamycins for example cefbuperazone, cefmetazole, cefininox, cefotetan, cefoxitin; monobactams for example aztreonam, carumonam, tigemonam), oxacephems, flomoxef, moxalactam; penicillins for example amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin and other like ritipenem; lincosamides for example clindamycin and lincomycin; macrolides for example azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin; polypeptides for example amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin and zinc bacitracin; tetracyclines for example apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline and, e.g., tetracycline, and pharmaceutically acceptable salts thereof, and mixtures thereof.

In one aspect, compositions can comprise ketorolac compound(s), phenylephrine compound(s), (e.g., ketorolac tromethamine and phenylephrine HCl) and synthetic anti-microbial(s), e.g., synthetic antibacterial(s). In aspects, antibacterials can be any pharmaceutically/ophthalmologically suitable synthetic antibacterial. In aspects, suitable synthetic antibacterials for combination compositions/methods include 2,4-diaminopyrimidines for example brodimoprim, tetroxoprim, trimethoprim; nitrofurans for example furaltadone, furazolium chloride, nifuradene, nifuratel, nifurfoline, nifurpirinol, nifurprazine, nifurtoinol, nitrofurantoin; quinolones and analogs, e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin; sulfonamides for example acetyl sulfamethoxypyrazine, benzylsulfamide, chloramine-b, chloramine-t, dichloramine-t, N2-formylsulfisomidine, N4-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfarnerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, N4-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole; sulfones for example acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone; and others like clofoctol, hexedine, methenamine, methenamine anhydromethylene-citrate, methenamine hippurate, methenamine mandelate, methenamine sulfosalicylate, nitroxoline, taurolidine, and xibornol, salts thereof, and mixtures of any thereof.

In one aspect, the invention provides compositions comprising one or more ketorolac compounds, one or more phenylephrine compounds, (e.g., ketorolac tromethamine and phenylephrine HCl) and one or more antimicrobials, e.g., one or more antifungal agents. In aspects, an antifungal agent can be a synthetic antifungal agent. In aspects, suitable antifungal agents can be any pharmaceutically acceptable and ophthalmologically suitable antifungal agents. In aspects, antifungal agents suitable for combination therapy are, for example, polyenes e.g., amphotericin b, candicidin, dennostatin, filipin, fungichromin, hachimycin, hamycin, lucensomycin, mepartricin, natamycin, nystatin, pecilocin, perimycin, azaserine, griseofulvin, oligomycins, neomycin undecylenate, pyrrolnitrin, siccanin, tubercidin, and, e.g., viridin, and pharmaceutically acceptable salts thereof, and mixtures thereof. Examples of suitable synthetic antifungals include, e.g., allylamines for example butenafine, naftifine, terbinafine, imidazoles for example bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole; thiocarbamates for example tolciclate, tolindate, tolnaftate; triazoles for example fluconazole, itraconazole, saperconazole, terconazole and others like acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and, e.g., zinc propionate, and pharmaceutically acceptable salts thereof, and mixtures thereof.

In aspects, compositions can comprise one or more pharmaceutically acceptable and ophthalmological anti-microbial agents, e.g., an antibacterial, a synthetic antibacterial, an antifungal, a synthetic antifungal, wherein the anti-microbial agent is present in an amount effective in detectably or significantly treating, preventing, or inhibiting development of or progression of a microbial growth, e.g., a bacterial growth or a fungal growth.

In aspects, compositions comprise means for imparting/providing an effective, detectable, or significant antimicrobial effect to/of composition(s). Such means comprise the named agents disclosed herein and any known equivalents of such named agents can also be, e.g., are, incorporated into compositions or methods of the invention.

Other Active Pharmaceutical Agent(s)

In one aspect, the invention provides compositions comprising one or more ketorolac compounds, one or more phenylephrine compounds, (e.g., ketorolac tromethamine and phenylephrine HCl) and one or more antineoplastic agent(s), anti-allergic agent(s), glaucoma-treating agent(s), antiviral agent(s), anti-mycotic agent(s), intraocular pressure reducing agent(s), or glaucoma-treating agent(s). In aspects, suitable such agents can be any pharmaceutically acceptable and ophthalmologically suitable such agents. In certain aspects, compositions comprise no additional active pharmaceutical agent (e.g., the only present active pharmaceutical ingredients are one or more ketorolac compounds and one or more phenylephrine compounds, such as, e.g., ketorolac tromethamine and phenylephrine HCL.)

Antineoplastic Agent(s)

In aspects, antineoplastic agents suitable for combination therapy/compositions are, for example, ophthalmologically suitable forms of mitomycin C or fluorouracil (5FU), or Intron A, or ophthalmologically suitable forms of methotrexate, cytarabine (Ara-C), thiotepa, chlorambucil, dacarbazine, or temozolamide, etc.

Compositions can in aspects comprise a "means" for providing imparting/providing an effective, detectable, or significant antineoplastic effect to/of composition(s), comprising named agents disclosed herein or known equivalents thereto. can also be, e.g., are, incorporated into compositions or methods of the invention.

Anti-Allergic Agent(s)

In aspects, anti-allergic agents suitable for combination therapy/compositions also or alternatively are incorporated. Examples of such agents include ophthalmologically suitable antihistamines (e.g., levocabastine, emedastine, bilastine, cetirizine, etc.), ophthalmologically suitable mast-cell stabilizers (e.g., cromolyn, nedocromil, etc.), ophthalmologically suitable dual-activity agents (providing both antihistamine and mast-cell inhibition activity, such as, e.g., olopatadine, bepotastine, alcaftadine, etc.), ophthalmologically suitable corticosteroids (e.g., loteprednol etabonate, loteprednol, mapracorat, prednisolone acetate, prednisolone phosphate, dexamethasone, etc.), ophthalmologically suitable non-steroidal anti-inflammatory drugs (such as, e.g., those disclosed above, or, e.g., specifically be, e.g., diclofenac sodium, nepafenac, etc.), ophthalmologically suitable decongestants (e.g., brimonidine, etc.), ophthalmologically suitable immunomodulators (e.g., cyclosporine A, tacrolimus, etc.) and others such as ophthalmologically suitable cannabis preparations, immunobiologicals, etc. In aspects, compositions comprise a "means" for providing an effective, detectable, or significant anti-allergic effect to/of composition(s) comprising any of such agents disclosed herein and any known equivalents of such named agents.

Anti-Glaucoma Agent(s)/Intraocular Pressure Reduction Agent(s)

In aspects, compositions include intraocular pressure-treating agents or glaucoma-treating agents. Agents suitable for combination therapy or compositions are, for example, beta blockers (e.g., nonselective beta blockers such as, e.g., timolol maleate, levobunolol, carteolol, metipranolol, etc. or, e.g., selective beta blockers such as, e.g., betaxolol, etc.), mimotics (e.g., pilocarpine, etc.), carbonic anhydrase inhibitors (e.g., dorzolamide, brinzolamide, etc.), sympathomimetics (e.g., epinephrine-like sympathomimetics such as, e.g., dipivefrin, etc. or, e.g., clonidine-like sympathomimetics such as, e.g., brimonidine, apraclonidine, etc.), prostaglandin analogs (e.g., latanoprost, travoprost, tafluprost, bimatoprost, latanoprosten bunod, etc.), etc. In this and any other ingredient aspect of the invention, the invention also can be characterized as comprising a "means" for providing a recited function, here imparting/providing an effective, detectable or significant ability to reduce intraocular pressure or state(s), symptom(s), or condition(s) related to glaucoma effect to/of composition(s) of the invention. In such a respect, any known equivalents of such named agents can also be, e.g., are, incorporated into compositions or methods of the invention. In aspects, compositions provide means for achieving such results, comprising agents described herein or equivalents thereof (e.g., the above-described anti-glaucoma or intraocular pressure reducing agents can be described as anti-glaucoma means or means for providing effective, detectable, or significant anti-glaucoma activity/characteristics to the composition, or intraocular pressure reduction means).

Antiviral Agent(s)

In aspects, antiviral agents suitable for combination therapy/compositions are incorporated in compositions/methods. Examples of such agents are, for example, idoxuridine (IDU), iododesoxycytidine (IDC), vidarabine (Ara-A), trifluridine (TFT), aciclovir, ganciclovir, trifluridine, idoxuridine, ophthalmologically suitable formulations of valganciclovir, foscarnet, etc. In aspects, compositions comprise "means" for providing an effective, detectable, or significant antiviral effect to/of composition(s) (comprising agents described herein or known equivalents of such named agents).

Antimycotic Agent(s)

In aspects, anti-mycotic agents suitable for combination therapy/compositions are incorporated in compositions/methods. Examples of such agents are, for example, ophthalmologically suitable polyenes (e.g., amphotericin B (AMB), nystatin, nytamycin (NTM), etc.), ophthalmologically suitable azoles (e.g., imidazoles or triazoles, including, e.g., miconazole (MCZ), econazole (ECZ), ketoconazole (KCZ), itraconazole (ICZ), fluconazole), voriconazole, posaconazole (PCZ), etc.), ophthalmologically suitable pyrimidines (e.g., 5-fluorocystine (5-FC), flucytosine, etc.), ophthalmologically suitable echinocandins (e.g., caspofungin (CFG), micafungin (MFG), etc.), etc. In aspects, compositions comprise a "means" for providing an effective, detectable, or significant antimycotic effect to/of composition(s), comprising named agents of such type provided herein and known equivalents thereof.

Buffer-Free Nature of Certain Compositions (No Buffer Component)

In aspects, compositions are characterizable as lacking (e.g., "devoid of") any detectable or significant buffer component (sometimes simply called a "buffer"). Buffers are known and in general guidance provided herein regarding buffers is meant to either exemplify the invention or to set forth certain embodiments only without limiting the general scope of the invention. Typically, buffers significantly resist changes in pH of a given composition under present conditions of such composition including its current overall pH. In aspects, a buffer component is a combination of a weak base (e.g., a base that is partially dissociated in an aqueous solution) and a conjugate acid, a weak acid (e.g., an acid that only partially dissociates into its ions in an aqueous solution or water) and a conjugate base, or both, the buffer component capable of preventing a significant change in pH upon the addition of a small amount of a either a strong acid or a strong base (e.g., such a composition can neutralize the addition of a small amount of a strong acid or a strong base).

Additional exemplary characteristics of such acids and bases are described elsewhere or in the art.

In aspects, a buffer component can provide a composition with the ability to significantly resist a significant change in its pH when H+ or OH− ions are added or removed owing to other reaction(s) occurring within the same solution. In aspects, lack of such a buffer component renders composition(s) unable to resist such a pH change under such conditions, e.g., upon the addition or removal of a sufficient number of H+ or OH− ions, such as the addition of a small amount of a strong acid or strong base or which are generated by other reaction(s) occurring within the same solution.

In aspects, a buffer component is a combination of a weak base and its conjugate acid, a weak acid and its conjugate base, or both, wherein the acid and base pairs of such a buffer component are present in concentrations of within ~10× of one another, such as, e.g., within ~9×, ~8×, ~7×, ~6×, ~5×, ~4×, ~3×, ~2×, of each other, or are present in at least substantially equivalent, significantly similar, or approximately the same amounts as one another. In aspects, a buffer component is a combination of a weak base and its conjugate acid, a weak acid and its conjugate base, or both, wherein a pKa of any such buffer component is between 4.3-8.3, such as the pKa of any such buffer component is between 5.3-7.3, e.g., between about 6.0 and 6.6.

In aspects, a buffer component is a combination of a weak base and its conjugate acid, a weak acid and its conjugate base, or both; wherein the acid and base pairs of such a buffer component are present in concentrations of within 10× of one another; and wherein the pKa of any such buffer component is between 4.3-8.3, e.g., the pKa of any such buffer component is between 5.3-7.3 or ~6.0-6.6. In aspects, a buffer component wherein (a) the buffer component is a combination of a weak base and its conjugate acid, a weak acid and its conjugate base, or both; (b) the acid and base pairs of such a buffer component are present in concentrations of within 10× of one another; (c) the pKa of any such buffer component is between 4.3-8.3, such as the pKa of any such buffer component is between 5.3-7.3, e.g., between about 6.0 and 6.6; and (d) wherein, when the composition is at a pH of 6.3, the acid and base pairs of the buffer component can prevent a change in pH of the composition of more than 2% when 0.1 moles of HCl or 0.1 moles of NaOH are added to 1 L of the composition.

Readers will understand that the characterization of buffer components provided in this section provides basis for, inter alia, what is lacking at any detectable or significant level in certain compositions of the invention. As noted, despite the lack of such any such buffer component, compositions of the invention are able to be effective and surprisingly stable for prolonged periods of time (e.g., ≥~2, ≥~3, ≥~6, ≥~12, ≥~18, or ≥~24 months).

In aspects, compositions are capable of maintaining the pH of the composition established during manufacturing over an extended storage period, e.g., a storage period of ≥~1, ≥~2, ≥~0.3, ≥~6, ≥~12, ≥~18, or ≥~24 months, at about 25° C.+/−2° C. and about 60% relative humidity, at about 40° C.+/−2° C. and about 75% relative humidity, or under either or both such conditions. In aspects, compositions are capable of detectably or significantly transitioning to the pH, approximately the same pH, an effectively similar pH, or a significantly similar pH, of an environment to which they are added, e.g., the pH of an irrigation solution to which an, e.g., carrier composition is added to form a combination composition, within about 30 seconds, e.g., within ~25 seconds, ~20 seconds, ~15 seconds, ~10 seconds, ~5 seconds, or less, such as within about 1 second. In cases, a pharmaceutically acceptable and ophthalmologically suitable composition provided by the invention, e.g., a liquid carrier composition, comprising effective amounts of one or more ketorolac compounds (e.g., ketorolac tromethamine) and one or more phenylephrine compounds (e.g., phenylephrine HCl), capable of maintaining a pH of between about 5.5-about 7.5, such as between about 6.0-6.5 when stored at 25° C. and 60% relative humidity or when stored at about 40° C.+/−2° C. and about 75% relative humidity for a period of at least about 1 month, such as, e.g., ≥~2 months, ≥~3 months, ≥~6 months, ≥~8 months, ≥~10 months, ≥~12 months, ≥~18 months, or ≥~24 months, lacks a buffer component as described herein (e.g., lacks a buffering means), such that the compositions are capable of taking on the pH of a solution or the pH of the environment to which they are added (e.g., the pH of an irrigation solution or the pH of the eye) within about, e.g., 30 seconds, ~15 seconds, ~5 seconds, or less.

In aspects, a typical buffer component would comprise any ophthalmologically suitable and pharmaceutically acceptable buffer which does not detectably or significantly interfere with the required functionality of any one or more other composition constituents. In aspects, exemplary constituents of a buffer component comprise, e.g., one or more of a phosphate buffer (e.g., sodium phosphate, e.g., monobasic or dibasic sodium phosphate), citrate buffer (e.g., sodium citrate compound, e.g., sodium citrate dihydrate), tris buffer, carbonate buffer (e.g., ammonium carbonate, sodium carbonate or sodium bicarbonate), succinate buffer, maleate buffer, a borate buffer, combinations of sodium hydroxide, potassium hydroxide, hydrochloric acid, lactic acid, phosphoric acid, sulfuric acid, etc. or combinations thereof. In specific aspects, compositions do not comprise any one or more such buffers. In aspects, compositions comprise no such buffers. Here, disclosures of aspects based on "not comprising" an element provide simultaneous support for having very low amounts of an element, lacking an effective amount of an element, or lacking any detectable amount of such an element, etc.

In aspects, compositions comprise a "means" for providing an effective, detectable, or significant pH buffering effect comprising any named agents disclosed herein for providing such functions and any known equivalents thereof.

Additional Means/Steps for Performing Functions

In aspects, compositions comprise mean(s) and methods include step(s) for performing specific function(s). In general, any element described herein as a "means" for performing a function can also, wherever suitable, serve as a "step for" performing a function in the context of methods of the invention, and vice versa. E.g., a component described herein as a means for preserving a composition also simultaneously and implicitly supports a method of making such a composition comprising a step of preserving a composition and a kit comprising a means for delivering a composition implicitly and simultaneously provides a step for delivering the composition comprising the use of such delivery means.

In one aspect, compositions comprise means for chelation, e.g., where such means for chelation detectably or significantly improving the stability of the one or more ketorolac compounds, detectably or significantly improving the stability of one or more phenylephrine compounds, detectably enhancing the effectiveness of one or more preservatives, or any combination thereof (each and collectively, "chelation means"). Support for chelation means can be found in, e.g., the subsection entitled, "Chelating Agent(s)".

In one aspect, compositions comprise means for protecting APIs from oxidation, e.g., means for providing antioxidant protection of API(s), in aspects such means for antioxidant protection of API(s) detectably or significantly improving the stability of ketorolac compound(s), phenylephrine compound(s), or both; detectably or significantly reducing impurities associated with either or both APIs; or both (e.g., DOS reducing API-associated impurities detected at, e.g., time points 2 weeks, 1 months, 2 months, or 3 months or more (e.g., time periods exemplified in the Examples) after manufacturing), or providing any combination thereof ("antioxidant means"). Support for antioxidant means is found in the subsection entitled "Antioxidant(s)."

In one aspect, compositions comprise means for providing a suitable tonicity of the composition(s), providing a suitable osmolality of the composition(s), e.g., means for providing composition(s) which do not cause detectable or significant ocular irritation due to tonicity when provided according to instructions (each and collectively "tonicity means"). Support for tonicity means can be found in, e.g., the subsection entitled, "Tonicity Agent(s)."

In one aspect, compositions comprise means for adjusting the pH of the composition(s), providing a suitable or target pH of the composition(s) of between about, e.g., ~5.5-~7.5, such as, e.g., ~5.8-~6.8, or, e.g., between about 6.0-about 6.6, e.g., about 6.3, ("pH adjusting means"). Support for pH adjusting means can be found in, e.g., the subsection entitled, "pH Adjusting Agent(s)".

In one aspect, compositions comprise means for preserving the composition(s), e.g., detectably or significantly inhibit microbial growth, detectably or significantly reducing the number of impurities, or otherwise detectably or significantly improving the stability of the compositions (e.g., preserving the amount of API(s) contained therein), e.g., such that compositions remain safe and suitable for administration after storage of at least about 1 month, e.g., ~2 months, or e.g., ~3 months or more after manufacturing at room temperature (25° C. and about 60% relative humidity) ("preservation means"). Support for preservation means can be found in, e.g., the subsection entitled, "Preservation Agent(s)".

In one aspect, compositions comprise means for providing compositions of the invention as liquid compositions, e.g., providing a carrier for the API's and any one or more other excipients of the composition(s) ("carrier means"). Support for carrier means can be found in, e.g., the subsection entitled, "Carrier(s)."

In one aspect, compositions comprise means for providing compositions of the invention with detectable or significant increases in clinically relevant anti-inflammatory effect over that provided by the one or more ketorolac compound(s) (e.g., ketorolac tromethamine) alone ("anti-inflammatory means"). Support for anti-inflammatory means can be found in, e.g., the subsection entitled, "Anti-inflammatory Agent(s)."

In one aspect, compositions comprise means for detectably or significantly treating, preventing, or inhibiting development of, or progression of, microbial growth, e.g., bacterial or fungal growth, such as that present in an ocular infection ("anti-microbial means"). In aspects, such antimicrobial means for inhibiting microbial growth can be present in the composition in addition to (e.g., separately from) any one or more other preservation means (e.g., means for detectably or significantly reducing impurities or detectably or significantly extending stability over a storage period) which may be present in the composition. Support for anti-microbial means can be found in, e.g., the subsection entitled, "Antimicrobial Agent(s)."

In aspects, compositions lack a means of buffering. E.g., lacking means for buffering against the addition of, or lack a means of buffering for the presence of (if/when such compositions are placed into an environment having), contact with compositions of a different pH ("buffering means"). In aspects, such buffering means are described in, e.g., the subsection entitled, "Buffer-free Nature of Certain Compositions (No Buffer Component)."

In one aspect, compositions comprise means for producing/enhancing an anti-allergic effect from a composition, such as a DOS anti-allergic effect ("anti-allergic means"). Support for anti-allergic means is found in, e.g., the subsection entitled, "Anti-allergic Agent(s)".

In one aspect, compositions comprise means for providing compositions of the invention detectable or significant antineoplastic activity ("antineoplastic means"). Support for antineoplastic means can be found in, e.g., the subsection entitled, "Antineoplastic Agent(s)".

In one aspect, compositions comprise means for providing/imparting/causing reduction in intraocular pressure ("IOP") or means to treat state(s), symptom(s), or condition(s) related to glaucoma ("anti-glaucoma means" or "intraocular pressure reduction means"), e.g., DOS effects of either or both. Support for anti-glaucoma/IOP-reduction means are found in, e.g., the subsection entitled, "Anti-glaucoma Agent(s)/Intraocular Pressure Reduction Agent(s)".

In one aspect, compositions comprise means for providing antiviral activity ("antiviral means"), e.g., DOS antiviral effect(s). Support for antiviral means can be found in, e.g., the subsection entitled, "Antiviral Agent(s)".

In one aspect, compositions comprise means for providing compositions of the invention detectable or significant anti-mycotic activity ("anti-mycotic means"). Support for anti-mycotic means can be found in, e.g., the subsection entitled, "Antimycotic Agent(s)".

Composition pH

In aspects, compositions have a pH of between ~5.0-~8.0, such as, e.g., ~5.0-~7.8, ~5.0-~7.6, ~5.0-~7.4, ~5.0-~7.2, ~5.0-~7.0, ~5.0-~6.8, ~5.0-~6.6, or e.g., ~5.0-~6.4, such as, e.g., ~5.2-~8.0, ~5.4-~8.0, ~5.6-~8.0, ~5.8-~8.0, ~6.0-~8.0, or, e.g., ~6.2-~8.0, such as, e.g., ~5.4-~7.2, ~5.7-~5.7-~6.9, ~6.0-~6.6, or, e.g., have a pH of about 6.3.

In aspects, compositions are capable of maintaining a pH of between ~5.4-~7.2, ~5.7-~5.7-~6.9, –6.0-~6.6, or, of about 6.3 for at least about 1 month, e.g., ≥~2 months, ≥~3 months, ≥~4 months, ≥~5 months, ≥~6 months, ≥~7 months, ≥~8 months, ≥~9 months, ≥~10 months, ≥~11 months, ≥~12 months or, in aspects, longer (e.g., ≥~24 months), while stored at about 25° C. and about 60% relative humidity ("RH"), when stored under accelerated conditions at about 40° C. and −75% relative humidity or when stored under either or both conditions.

In aspects, compositions are capable of adapting to the pH of a composition or environment to which it is added (or, e.g., at least generally to, at least substantially to, at least essentially to, essentially to, or to the pH of a composition or environment to which it is added) within about 30 seconds, such as within ~28 seconds, ~26 seconds, ~24 seconds, ~22 seconds, ~20 seconds, ~18 seconds, ~16 seconds, ~14 seconds, ~12 seconds, ~10 seconds, ~8 seconds, ~6 seconds, ~4 seconds, ~2 seconds, ~1 seconds, or even less of its addition thereto. In aspects, compositions do not have a pH of less than 5.0, e.g., less than ~4.8, ~4.6, ~4.4, ~4.2, or ~4.0.

Stability Characteristics

The term "stable" is used here to refer to pharmaceutically/ophthalmologically suitable/acceptable compositions comprising ketorolac compound(s) and phenylephrine compound(s) having sufficient physical and chemical integrity, e.g., to maintain at least 98% of the amount of ketorolac compound(s), phenylephrine compound(s), or both initially in the composition; to maintain total impurities (e.g., a below 0.5% (e.g., below pharmaceutically acceptable level) to allow storage at a convenient temperature, such as between about 2° C. and about 50° C., for a commercially reasonable period of time, such as, e.g., at least about 1 month, at least about 2 months, or at least about 3 months or more, e.g. typically for at least about 4, ~5, ~6, ~7, ~8, ~9, ~10, ~11, ~12, ~18, ~24, ~30, or, e.g., ~36 months, when stored in its original packaging. The term "physical stability" typically refers to maintenance of color, dissolved oxygen level, head space oxygen level, particulate matter, etc. For the purpose of the compositions described here, the term "chemical stability" typically refers to formation of drug-related impurities in terms of total impurity, single maximum individual impurity, maximum individual unknown impurity, or any combination of any or all thereof. In aspects, chemical stability also includes maintenance of pH of the finished formulation of the course of such storage under such conditions, e.g., for a period of storage of at least about 1 month, e.g., ≥~3 months, ≥~6 months, ≥~9 months, ≥~12 months, ≥~18 months, ≥~24 months, ≥~28 months, ≥~32 months, or ≥~36 months post manufacturing, at between about 2° C. and about 50° C.

The terms "impurity" or "impurities" are understood to refer to undesired substance(s) in a composition which may be present in a composition immediately following manufacturing (e.g., at initial quality control testing composition following manufacturing, prior to storage) or which may be formed after a certain period of shelf life of a composition. Impurities may be formed via degradation of one or more components of the composition. Sources of degradation can include, e.g., oxidation, light, ultraviolet light, moisture, heat, changes in pH, and composition component interactions.

The term "purity" or reference to a composition being X % (e.g., 99.5% "pure") means relatively measured against a detectably or significantly different state or collection of molecules/compounds. For example, a composition comprising, e.g., at least about a 99.5% pure ketorolac compound (or, e.g., a 99.5% pure phenylephrine compound) is a composition comprising less than 0.5% of a ketorolac compound-related impurity.

The term "storage conditions" refers to storage at 25° C.+/−2° C.; storage at about 25° C. and about 60% relative humidity; storage at about 40° C. and about 75% relative humidity; or storage under any combination of such conditions. Herein, reference to any single such storage condition or reference to a combination of a subset of such storage conditions should be interpreted in certain aspects to incorporate each of the storage conditions reflected in this paragraph.

In aspects, compositions are stable compositions such that ketorolac compound(s) of the compositions, the phenylephrine compound(s) of the compositions, or both are present in an amount of at least 98%, such as ≥~98.2%, ≥~98.4%, ≥~98.6%, ≥~98.8%, ≥~99%, ≥~99.2%, ≥~99.4%, ≥~99.6%, ≥~99.8%, or even ~100% for a period of at least about 1 month (e.g., ~2, ~3, ~4, ~5, ~6 months or more such as ≥12, ≥18, or ≥24 months) when stored at about 25° C. and about 60% RH, or when stored under accelerated conditions at about 40° C. and ~75% RH.

In aspects, compositions are capable of maintaining a level of pure ketorolac compound, a level of pure phenylephrine compound, or both, which is at least about 99.5% pure, such as, e.g., at least ~99.6%, ~99.7%, ~99.8%, ~99.9%, or, e.g., which is even ~100% pure. In aspects, compositions demonstrating such compound purity comprise less than about 0.5%, such as, e.g., <~0.4%, <~0.35%, <~0.3%, <~0.25%, <~0.2%, <~0.15%, <~0.1%, <~0.05%, or even less of total impurities.

In aspects, compositions are capable of maintaining a level of total impurities of less than about 0.5%, such as less than ~0.4%, <~0.3%, <~0.2%, or, e.g., <0.1% or less than that quantifiable by the limits of detection of impurity detection equipment used in such an analysis, for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% RH, or when stored under accelerated conditions at about 40° C. and −75% RH.

In aspects, compositions are capable of maintaining a level of the impurity identifiable as 1-(3-hydroxyphenyl)-2-(methylamino) ethan-1-one hydrochloride at or below 0.4%, such as <~0.3%, <~0.2%, or, e.g., <0.1% or less than that quantifiable by the limits of detection of impurity detection equipment used in such an analysis, for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% relative humidity, or when stored under accelerated conditions at about 40° C. and about 75% relative humidity.

In aspects, compositions are capable of maintaining a level of the impurity identifiable as 5-benzoyl-2,3-dihydro-1H-pyrrolizine-1H-one at or below 0.4%, such as <~0.3%, <~0.2%, or, e.g., <0.1% or less than that quantifiable by the limits of detection of impurity detection equipment used in such an analysis, for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% relative humidity, or when stored under accelerated conditions at about 40° C. and −75% RH.

In aspects, compositions are capable of maintaining a level of the impurity identifiable as 5-benzoyl-2,3-dihydro-1H-pyrrolizine-1H-one and the level of impurity identifiable as 1-(3-hydroxyphenyl)-2-(methylamino) ethan-1-one hydrochloride each at or below 0.4%, such as <~0.3%, <~0.2%, or, e.g., <0.1% or less than that quantifiable by the limits of detection of impurity detection equipment used in such an analysis, for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% relative humidity, or when stored under accelerated conditions at about 40° C. and about 75% relative humidity.

In aspects, compositions are capable of maintaining a level of the impurities identifiable as 5-benzoyl-2,3-dihydro-1H-pyrrolizine-1H-one and 1-(3-hydroxyphenyl)-2-(methylamino) ethan-1-one hydrochloride together (e.g., the sum of the two impurities) at or below 0.4%, such as <~0.3%, <~0.2%, or, e.g., <0.1% or less than that quantifiable by the limits of detection of impurity detection equipment used in such an analysis, for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% relative humidity, or when stored under accelerated conditions at about 40° C. and about 75% relative humidity.

In aspects, compositions are capable of maintaining a pH within about 10% of a starting pH, such as within about 9%, ~8%, ~7%, ~6%, ~5%, ~4%, ~3%, ~2%, or within about 1% or less, or, e.g., within a range of about 1% to about 10%, ~2%-~10%, ~4%-~10%, ~6%-~10% or ~8%-~10%, e.g., ~1%-~8%, ~1%-~6%, ~1%-~4%, or ~1%-~2%, for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% relative humidity, or when stored under accelerated conditions at about 40° C. and about 75% relative humidity.

In aspects, compositions are capable of maintaining a pH of between about 5 to about 8, such as, e.g., ~5.0-~7.8, ~5.0-~7.6, ~5.0-~7.4, ~5.0-~7.2, or ~5.0-~7.0, e.g., ~5.2-~8, ~5.4-~8, ~5.6-~8, ~5.8-~8, ~6-~8, or ~6.2-~8, such as, e.g., ~5.2-~7.8, ~5.4-~7.6, ~5.6-~7.4, ~5.8-~7.2, ~6-~7, or ~6.2-~6.8, such as, e.g., ~6.2-~6.7 or, e.g., ~6.2-~6.6 for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% relative humidity, or when stored under accelerated conditions at about 40° C. and about 75% relative humidity.

In aspects, compositions are capable of maintaining (1) a level of total impurities of less than about 0.5%; (2) a level of the impurity identifiable as 1-(3-hydroxyphenyl)-2-(methylamino) ethan-1-one hydrochloride at or below 0.4%; (3) a level of the impurity identifiable as 5-benzoyl-2,3-dihydro-1H-pyrrolizine-1H-one at or below 0.4%; (4) a level of the impurity identifiable as 5-benzoyl-2,3-dihydro-1H-pyrrolizine-1H-one and the level of impurity identifiable as 1-(3-hydroxyphenyl)-2-(methylamino) ethan-1-one hydrochloride each at or below 0.4%; (5) a level of the impurities identifiable as 5-benzoyl-2,3-dihydro-1H-pyrrolizine-1H-one and 1-(3-hydroxyphenyl)-2-(methylamino) ethan-1-one hydrochloride together (e.g., the sum of the two impurities) at or below 0.4%; (6) a pH within about 10% of a starting pH (e.g., within 10% of the pH of the composition immediately post-manufacturing); and (7) a pH of between about ~5-~8 (e.g., between about 6 and about 7, such as between about 6.2 and about 6.7) for a period of at least about 1 month or, e.g., ≥~2 months, ≥~3, ≥~4, ≥~5, or ≥~6 months, such as ≥~6 months, ≥~7 months, ≥~8 months, ≥~9 months, ≥~10 months, ≥~11 months, ≥~12 months, ≥~16 months, ≥~20 months, ≥~24 months, ≥~28 months, ≥~32 months, or ≥~36 months or more when stored at about 25° C. and about 60% relative humidity, or when stored under accelerated conditions at about 40° C. and about 75% relative humidity.

Combination Compositions

In aspects, one or more other pharmaceutically acceptable and ophthalmologically suitable additional component(s) can be combined with a core or carrier composition to form a combination composition. In this context, the term "combination component" is used to describe such a composition, formulation, or other product which, when combined with a core or carrier composition, forms a combination composition. For example, an irrigation solution (e.g., an independent irrigation solution product), can be present with the compositions described herein to form a combination composition. In aspects, the combination of a core or carrier composition with one or more additional pharmaceutically acceptable and ophthalmologically suitable combination components such as an irrigation solution product can form a combination composition solution, the combination composition solution itself suitable for use as an irrigation solution during ophthalmic procedures. The combination component itself typically is a composition that is suitable for use in ophthalmological applications, apart from the core composition or carrier composition. E.g., an irrigation solution additional component of a combination composition can be suitable as an irrigation solution during an ophthalmologically-related surgery, such as a lens replacement surgery or a cataract surgery, both in the presence of a core composition/carrier composition, or alone, or with other APIs.

As described herein, compositions can lack a buffer component. In aspects, compositions do not maintain their pH within about 10% of their pH immediately prior to their combination with one or more components having a significantly different pH when combined with one or more other combination components having a significantly different pH or that can significantly modify the pH of the composition(s). Thus, in aspects, as a component of combination compositions, core compositions and carrier compositions of the invention can significantly take on the pH of a combination component (or the pH of a mixture of combination components), such as, e.g., an irrigation solution, present in a combination composition as compared to a corresponding composition comprising a typical amount of a buffer. In aspects, such a pH change can occur within, e.g., ~30, ~25, ~20, ~15, ~10, ~5 seconds, or, e.g., within about 1 second of such an addition. In aspects, upon addition of a composition to an irrigation solution (combination component) prior to use/administration, the composition detectably or significantly resists a change in pH as described above, and, in aspects, in a manner similar to the performance of OMIDRIA® or similar reference product. Herein, reference to OMIDRIA® (or OMIDRIA or Omidria) means the product approved by the United States Food and Drug Administration (FDA) under NDA number 205388 and the trademark OMIDRIA® and sold under such registered trademark in the United States prior to the submission of this disclosure, e.g., as of May 30, 2016, May 30, 2017, May 30, 2018, May 30, 2019, May 30, 2020, May 30, 2021, or May 30, 2022, or another product sold under the same NDA. In aspects, a reference product is the pharmaceutical product approved by FDA under NDA number 205388 or a substantially similar product, such as a product that contains most, generally all, or all of the same ingredients in most, generally all, or all cases in the same amounts or which otherwise is approved under an amendment to the NDA without the requirement of any significant new clinical trial for FDA approval. Omidria is composed of 1% phenylephrine (phenylephrine hydrochloride) and 0.3% ketorolac (ketorolac tromethamine) as active ingredients, accompanied by the inactive ingredients citric acid monohydrate, sodium citrate dihydrate, water for injection (and may further comprise sodium hydroxide and/or hydrochloric acid for pH adjustment). In aspects, exemplary compositions, lacking such a buffer as described herein, adapt quickly (e.g., within ~30, ~10, ~5, or ~1 second(s)) to the pH of a combination component, as there is no significant buffer capacity present in the compositions to resist such a change in pH. In aspects, the ability of the compositions herein to adapt to the environment in which they are placed is one advantageous aspect of the invention.

In aspects, a composition is provided in aqueous form for combination with an ocular irrigation solution in administration to the eye of subjects, wherein the irrigation solution makes up more than 99% (e.g., ≥99.5%, ≥99.7%, or ≥99.9%) of the volume of the resulting combination composition formed by the combination of the initial core/carrier composition and the irrigation solution. E.g., an irrigation solution can dilute a core composition or carrier composition by, 100-150× (10000% to 15000%), e.g., ~110-140×, ~115-135×, or about 125×.

In aspects, combination component(s) of a combination composition mostly, generally, substantially, or essentially maintains pH upon the addition of a core or carrier composition, such that the combination composition comprises substantially the same pH, approximately the same pH, or significantly the same pH as the initial combination component.

In aspects, combination component(s) of a combination composition lacks any buffering means/element, e.g., lack a buffer component such that the combination composition is characterizable as buffer-free. In aspects, an entire combination composition can thus take on the pH of the environment into which the combination composition is dispensed/applied. In aspects, such a combination composition, e.g., such an irrigation solution, can adapt to or adopt the pH of the environment into which the combination composition is dispensed/applied, such as the pH of an eye to which the irrigation solution is added during an ophthalmologically-related procedures, e.g., a lens replacement or cataract surgery.

Method of Making/Manufacturing Compositions

In aspects, the invention provides for a method of manufacturing a composition described herein (such as, e.g., a composition comprising pharmaceutically acceptable and ophthalmologically suitable amounts of one or more ketorolac compounds (e.g., ketorolac tromethamine), one or more phenylephrine compounds (e.g., phenylephrine HCl), and optionally one or more excipients or APIs, such as, e.g., an effective amount of chelating agent(s), antioxidant(s), etc.). In aspects, such a composition has pH of about 6.3, is stable for at least 1 month when stored at ~25° C. and ~60% relative humidity or at about 40° C. and about 75% relative humidity, and maintains a total level of impurities of less than ~0.5% for a period of at least about 1 month (e.g., ≥3, ≥6, ≥12, ≥18, or ≥24 months) when stored at about 25° C. and about 60% relative humidity, at about 40° C. and about 75% relative humidity, or both. In further aspects, such a composition maintains a level of the specific impurity identifiable as 5-benzoyl-2,3-dihydro-1H-pyrrolizine-1H-one at or below 0.4%, the level of the specific impurity identifiable as 1-(3-hydroxyphenyl)-2-(methylamino) ethan-1-one hydrochloride at or below 0.4%, or the level of the combination of the specific impurities 5-benzoyl-2,3-dihydro-1H-pyrrolizine-1H-one and 1-(3-hydroxyphenyl)-2-(methylamino) ethan-1-one hydrochloride at or below 0.4% or a period of at least about 1 month (e.g., ≥3, ≥6, ≥12, ≥18, or ≥24 months) when stored at about 25° C. and about 60% relative humidity, at about 40° C. and about 75% relative humidity, or both. In aspects, the method of manufacturing such a composition comprises the steps of/steps for (1) dissolving ketorolac compound(s) in a carrier material to form a solution; (2) dissolving a phenylephrine compound(s) in the resulting solution of (1); (3) diluting the solution resulting from (2); (4) optionally adding one or more pH-adjusting agents to bring the pH of the solution resulting from (3) to a pH of between about 6.0-about 6.6, e.g., to a pH of about 6.3; and (5) bringing the final volume of the solution up to a final desired/suitable volume, maintaining effective amounts of the APIs.

According to specific aspects, the invention provides a method of manufacturing composition(s) described herein comprising dissolving a ketorolac compound in a carrier material such as water, e.g., such as WFI. In aspects, the WFI can be heated/hot WFI, such as at least about 100° F., ≥~105° F., ≥~110° F., ≥~115° F., ≥~120° F., ≥~125° F., or even hotter. In aspects, the hot WFI can be subjected to nitrogen purging. In aspects, the hot WFI can be subject to nitrogen purging until the WFI has a dissolved oxygen content below about 3 parts per million (ppm), such as below about 2.5 ppm, <2 ppm, <1.5 ppm, or, e.g., <1 ppm.

In aspects, prior to the addition of ketorolac, an amount of the initially nitrogen purged carrier material can be removed and transferred to a second container wherein nitrogen purging can continue, e.g., to remove a significant amount of nitrogen.

In aspects, the method comprises a composition comprising one or more excipients, such as ethylenediamine tetra acetic acid (EDTA). In aspects, the one or more excipients is added to the hot, nitrogen purged carrier material, e.g., water, prior to the addition of the ketorolac compound. In aspects, one or more excipients, such as EDTA, is added to the hot, nitrogen purged carrier material and completely dissolved prior to the addition of the ketorolac compound. In aspects, the excipient is added to nitrogen purged carrier material while stirring and stirring can be continued until the excipient is essentially dissolved, substantially entirely dissolved, or completely dissolved. In aspects, the excipient is completely dissolved prior to the addition of a ketorolac compound, and in aspects the ketorolac compound is completely dissolved prior to the addition of any one or more additional ingredients.

In aspects, upon the complete dissolution of the ketorolac compound, the method comprises the addition of a phenylephrine compound. In aspects, the phenylephrine compound can be added to the solution comprising completely dissolved ketorolac compound and optionally one or more completely dissolved excipients such as, e.g., EDTA while stirring, e.g., under constant stirring. In aspects, upon adding the phenylephrine compound, the solution can be continuously stirred until the phenylephrine compound is completely dissolved.

In aspects, upon establishing a solution comprising completely dissolved ketorolac compound, completely dissolved phenylephrine compound, and, if present, completely dissolved excipient(s) such as, e.g., completely dissolved EDTA, additional WFI (WFI having been removed prior to the addition of the ingredients above) can be added to the solution and mixed for at least about 5 minutes (min), ≥~6 min, ≥~7 min, ≥~8 min, ≥~9 min, ≥~10 min, ≥~11 min, ≥~12 min, ≥~13 min, ≥~14 min, or, e.g., ≥~15 min, to ensure complete mixing.

In aspects, the method comprises adjusting the pH of the above well-mixed solution to a pH of between about 6.0-about 6.5, such as, e.g., a pH of about 6.1, ~6.2, ~6.3, ~6.4, ~6.5, in specific aspects, about 6.3. In aspects, the method of manufacturing provided by the invention comprises modifying the pH using a sufficient amount of one or more pH adjusting agents to obtain such a target pH. In aspects, the pH adjusting agent is a strong acid or a strong base. In aspects, the pH adjusting agent is HCl, e.g., 1N HCl, or NaOH, e.g., 1N NaOH.

In aspects, the method of manufacturing comprises bringing the final solution, once pH-adjusted, to a final volume using remaining nitrogen purged carrier solution.

In aspects, the final solution is subjected to a sterilization step. In aspects, the method of manufacturing can comprise any suitable sterilization capable of yielding a composition free of detectable or significant material or microbial contamination. In aspects, such a sterilization step can comprise heat sterilization, gaseous sterilization, filtration sterilization, or radiation sterilization. Such steps as other steps described herein with respect to a functional result can also be characterized in methods as "steps for" performing a function, such as a "step for sterilizing" a composition, thus incorporating equivalent means for sterilization known presently in the art. In common aspects, the compositions, e.g., carrier compositions, can be subjected to a sterile filtration step prior to final packaging. In aspects, the sterilization step detectably or significantly reduces the amount(s) of related compound(s) and impurities associated with the ophthalmic composition upon storage of the composition at about 25° C. and about 60% relative humidity for a period of at least about 1 month, e.g., at least ~2, ~3, ~4, ~5, or, e.g., ~6 months or more (e.g., ≥12, ≥18, or ≥~24 months).

In aspects, upon being brought to a final volume, the carrier composition can be used to fill containers, in aspects single use containers, such as, e.g., pharmaceutically suitable single use vials. In aspects such vials can be, e.g., ~1 mL, ~2 mL, ~3 mL, ~4 mL, ~5 mL, ~6 mL, ~7 mL, ~8 mL, ~9 mL, or, e.g., ~10 mL containers (e.g., vials having any such volume).

According to aspects, the invention provides a method of manufacturing a pharmaceutically acceptable and ophthalmologically suitable liquid composition (a carrier composition) comprising an anti-inflammatory compound, such as a ketorolac compound, e.g., ketorolac tromethamine, and a mydriatic agent, such as a phenylephrine compound, e.g., phenylephrine HCl, wherein the formulation is free of a buffer component having one or more of the characteristics of a buffer component as described herein, wherein the anti-inflammatory and mydriatic compounds (e.g., ketorolac tromethamine and phenylephrine HCl) are provided as a fixed combination, and wherein the composition remains stable for at least about 1 month, e.g., at least about 2 months, e.g., in aspects at least about 3, ~4, ~5, ~6, ~7, ~8, ~10, or ~12 months or more, e.g., ~18 months, ~24 months, ~30 months, or ~36 months or more, at a temperature of about 25° C.+/−2° C. and about 60% relative humidity or under accelerated conditions at 40° C.+/−2° C. and about 75% relative humidity. In aspects, such compositions provided by the method can comprise about 0.1 wt/v. %-about 5 wt/v. % ketorolac compound, between about 0.1 wt/v. % about 10 wt/v. % phenylephrine compound. In aspects, compositions provided by the method can comprise ketorolac compound and phenylephrine compound in a ratio of about 1:1-about 1:13 (e.g., about 1:2-about 1:10). In aspects, compositions are reproducibly produced and quality screened for the presence of desired, target amounts of such APIs prior to packaging, use, etc. In aspects, the compositions provided by the method of the invention can comprise a chelating agent, such as, e.g., EDTA. In aspects, such a chelating agent, e.g., EDTA, can be present in an amount representing about 0.001 wt/v. %-0.2 wt/v. % of the composition resulting from the method. In aspects, the compositions provided by the method of the invention can comprise a carrier, e.g., an aqueous carrier, e.g., WFI, wherein the carrier represents at least about, e.g., 50%, ~60%, ~70%, ~80%, ~90%, ~95%, 97%, 98%, or, e.g., 99% of the composition.

According to aspects, the invention provides a method of manufacturing a composition capable of serving as a medicament, the composition capable of being added to an irrigation solution or, when in appropriate dilute form characterizable as an irrigation solution without combination with other components, for use in continuously irrigating an operative site or wound during an ophthalmologically-related operative/surgical procedure, such as lens replacement or cataract surgery.

In aspects, the invention provides a method of manufacturing a pharmaceutically/ophthalmologically suitable composition comprising a ketorolac compound, a phenylephrine compound, and optionally one or more additional components such as one or more additional excipients or one or more additional APIs, wherein the total amount of impurities is less than about 2.5%, e.g., <~2%, <~1.5%, <~1%, <~0.5%, or, e.g., <~0.1% after at least about 1 month, ~2 months, ~3 months, ~4 months, ~5 months, or, e.g., ≥~6, ≥~12, ≥~18, ≥~22, ≥~26, ≥~30, or ≥~36 months or more after manufacturing when stored at ~25° C. and ~60% relative humidity or, e.g., when stored under accelerated conditions of 40° C.+/−2° C. and about 75% relative humidity.

Product by Process Aspects

According to aspects, the invention provides a pharmaceutically acceptable and ophthalmologically suitable composition such as any one or more of the compositions described in this disclosure, wherein the composition is made by a process comprising (1) dissolving a ketorolac compound in a carrier material to form a solution of ketorolac; (2) dissolving a phenylephrine compound in the resulting solution of (1); (3) diluting the solution resulting from (2); adding one or more pH-adjusting agents to bring the pH of the solution resulting from (3) to a pH of between about 6.0-about 6.6, e.g., to a pH of about 6.3; (4) bringing the final volume of the solution up to a final desired volume (e.g., one of the exemplary final volumes described elsewhere). In aspects, the invention provides a composition such as a composition resulting from the application of the process of this paragraph and further comprising any one or more of the process steps in the method of manufacturing described herein.

In aspects, the invention provides a pharmaceutically acceptable and ophthalmologically suitable composition (e.g., ophthalmologically suitable core composition or ophthalmologically suitable carrier composition) for use in treating or preventing ophthalmic conditions, diseases, or for use in related products or procedures, comprising pharmaceutically acceptable amounts of each of one or more ketorolac compounds and one or more phenylephrine compounds, and further optionally comprising one or more additional excipients, APIs or both, wherein the composition (1) lacks a buffer component wherein (a) the buffer is a combination of a weak base and its conjugate acid, a weak acid and its conjugate base, or both; (b) wherein the acid and base pairs of such a buffer component are present in concentrations of within 10× of one another; (c) wherein the pKa of any such buffer component is between 4.3-8.3, such as the pKa of any such buffer component is between 5.3-7.3, e.g., between about 6.0 and 6.6; (d) wherein, when the ophthalmologically suitable composition is at a pH of 6.3, the acid and base pairs of the buffer component can prevent a change in pH of the composition of more than 2% when 0.1 moles of HCl or 0.1 moles of NaOH are added to 1 L of the composition; (2) maintains a pH of between 5.5-7; and (3) retains at least 97% of the one or more ketorolac compounds and at least 97% of the one or more phenylephrine compounds when stored at 25° C.+/−2° C. for at least about one month, e.g., ~2, ~3, ~4, ~5, or ~6 months, and e) wherein the composition is made by a process comprising (i) dissolving a ketorolac compound in a carrier material to form a solution of ketorolac; (ii) dissolving a phenylephrine compound in the resulting solution of (i); (iii) diluting the solution resulting from (ii); adding one or more pH-adjusting agents to bring the pH of the solution resulting from (iii) to a pH of between about 6.0-about 6.6, e.g., to a pH of about 6.3; (iv) bringing the final volume of the solution up to a final volume; and (v) being subjected to a sterilization step prior to final packaging. In aspects, the process used to make the compositions can comprise any one or more additional or specific manufacturing steps described herein and described in detail in the example provided in the Example section herein. Any of the above-described features can be modified as provided in other aspects of this disclosure. Thus, for example, in aspects wherein a buffer component is described as not encompassing a weak acid or weak base present in a less than 10× relationship with its conjugate in an aspect, readers will understand that any such disclosure also includes aspects wherein the relationship can be 15×, 20×, etc., as described in other aspects and where stability is described as 2, 3, 4, . . . 6 months in aspects it will be understood that such stability can be, e.g., 3-36 months or 6-30 months, etc.

"Kits" (Collections of Components)

In aspects, the invention provides kits comprising a pharmaceutically acceptable and ophthalmologically suitable composition according to any one or more of the compositions provided by aspects of the invention described herein. In aspects, such composition(s) are packaged in one or more containers, e.g., one or more single use containers, wherein the kit further comprises one or more delivery devices for (1) administering the composition to a recipient; (2) delivering the composition to an existing solution/composition (e.g., irrigation solution), device (e.g., component of an irrigation solution delivery system such as an irrigation solution bag), or system (e.g., a controlled-release, ophthalmic irrigation solution delivery system) for delivery to a recipient, or (3) both (1) and (2). Kits also can comprise additional containers for mixing or storing components or compositions. In aspects, kits comprise one or more container means, which can include containers described elsewhere (e.g., pharmaceutically acceptable vials) or known equivalents thereof.

In aspects, the invention provides a kit comprising a delivery device as described in this section, wherein any single use container comprising a composition present in the kit is accessible to the delivery device/system of the kit, such as, e.g., containing a stopper which effectively seals the single use container and effectively prevents contamination of the content therein prior to use but which is penetrable by the delivery device/system such that the delivery device can extract the composition from the single use container. In aspects, the invention provides the kit described above, wherein the delivery device is a syringe system, such as a syringe and an accompanying needle for use with the syringe. In aspects, a kit can comprise "delivery means" including such components or known equivalents of such components.

In aspects, the invention provides for a kit comprising a carrier composition. In aspects, the invention comprises a kit comprising a core composition in dry powder form. In aspects, the invention comprises a kit comprising a core composition in dry powder form wherein the kit further comprises one or more components for reconstituting the core composition. In aspects, such one or more other components can be, e.g., a carrier and one or more devices for transferring the carrier to the container maintaining the core composition, such as, e.g., a syringe and needle system.

In aspects, the invention provides kits as described in this section wherein the kits comprise a composition made by any one or more of the processes or methods disclosed herein.

In aspects, the invention provides a kit described in this section, wherein each single use container comprises between about 1 mL and about 10 mL of carrier composition, such as between ~1 mL-~9 mL, ~1 mL-~8 mL, ~1 mL-~7 mL, ~1 mL-~6 mL, ~1 mL-~5 mL, ~1 mL-~4 mL, ~1 mL-~3 mL, or ~1 mL-~2 mL, such as, e.g., ~2 mL-~10 mL, ~3 mL-~10 mL, or, e.g., ~4 mL-~10 mL, ~5 mL-~10 mL, ~6 mL-~10 mL, ~7 mL-~10 mL, ~-8 mL-~10 mL, or ~9 mL-~10 mL, as in, e.g., between ~2 mL-~9 mL, ~3 mL-~8 mL, ~3-~7 mL, ~3 mL-~6 mL, ~3 mL-~5 mL, or, e.g., in specific aspects about 4 mL.

In aspects, the invention provides a kit as described in this section, wherein the kit further comprises a separately packaged diluent for further diluting the composition prior to use. In aspects, such a diluent can be any diluent, such as any pharmaceutically acceptable and ophthalmologically suitable diluent, such as, e.g., carrier material, e.g., WFI.

In aspects, the invention provides a kit as described in this section, wherein the delivery device/system can further provide (be used to provide) a carrier composition contained therein to the eye in a controlled manner, such as, e.g., in a constant flow or a constant drop-by-drop manner. In aspects, delivery in a constant flow can be delivery in a controlled stream of carrier composition, such as, e.g., the pressure and volume of carrier composition in the stream of carrier composition is controllable by the user administering the composition(s), and wherein, in aspects, a volume of composition delivered during any 10 second unit of time during a delivery period may not vary from the volume of composition delivered during any other 10 second unit of time during a delivery period by more than about, e.g., 50%, such as, e.g., by ≤~45%, ≤~40%, ≤~35%, ≤~30%, ≤~25%, ≤~20%, ≤~15%, ≤~10%, ≤~5%, ≤~1% or even less. In aspects, such a delivery device/system is a syringe wherein the flow is controllable by the user of the syringe (administrator), such that the administrator can manually control the volume of composition delivered during any portion of a delivery period.

In aspects, the delivery device/system is capable of delivering a carrier composition contained in the kit to an irrigation delivery system or device of such an irrigation delivery system, e.g., to a solution bag of an irrigation delivery system. In aspects, delivery can be in a manner such that a controlled volume of composition is delivered; e.g., an amount of between about 1 mL-about 10 mL is delivered to such a device/system, such as an amount of, e.g., ~1 mL, ~2 mL, ~3 mL, ~4 mL, ~5 mL, ~6 mL, ~7 mL, ~8 mL, ~9 mL, or, e.g., ~10 mL, e.g., ~2 mL-~10 mL, ~3 mL-~10 mL, ~4 mL-~10 mL, ~5 mL-~10 mL, or, e.g., ~1 mL-~9 mL, ~1 mL-~8 mL, ~1 mL-~7 mL, ~1 mL-~6 mL, or ~1 mL-~5 mL, e.g., ~2 mL-~9 mL or ~3 mL-~8 mL is delivered to the system. In aspects, the delivery device/system can provide a carrier composition contained therein to a controlled-release ophthalmic irrigation solution delivery system (e.g., to a bag comprising an irrigation solution for use in the system) in a manner which does not detectably or significantly modify the sterile integrity of the composition.

In aspects, the invention provides for a kit as described in this section, wherein the kit has a shelf life when stored at about room temperature, such as, e.g., about 25° C.+/-~2° C., for at least about 1 month, e.g., ~2, ~3, ~4, ~5, ~6, ~7, ~8, ~9, ~10, ~11, or at least ~12 months, or at least about 24 months (e.g., ~1-~36, ~3-~36, ~6-~36, ~12-~36, ~18-~36, ~24-~36, or ~28-~36 months, e.g., ~1-~30, ~1-~28, ~1-~24, ~1-~20, ~1-~16, ~1-~12, ~1-~8, or ~1-~6 months).

Methods of Use

According to embodiments, the invention provides a pharmaceutically acceptable and ophthalmologically suitable composition having any one or more of the characteristics disclosed herein, e.g., wherein the composition is capable of providing a controlled, site-specific release of APIs in a tissue, part of an organ, etc. (e.g., to the eye). In aspects, composition(s) detectably or significantly increase the efficacy (e.g., by providing detectable or significant mydriatic effect) of an ophthalmic intervention during which the compositions are applied or detectably or significantly reduce the side effects of such an ophthalmic intervention (e.g., reducing inflammation resulting from such intervention). In aspects, the invention provides a method of using any one or more of the inventive compositions disclosed herein to increase the efficacy, e.g., providing detectable or significant mydriatic effect, of an ophthalmic intervention during which the composition is applied. In aspects, composition(s) detectably or significantly reduce the side effects of such an ophthalmic intervention, such as, e.g., detectably or significantly reduce inflammation resulting from such intervention. In aspects, such interventions can be, e.g., lens replacement or cataract surgeries. Controlled release of APIs is a concept known in the art. In general, controlled release means a release that is predictable during at least part of the release of the API from a composition and typically refers to a release that is modified in one or more ways with respect to an immediate release formulation. In aspects, the release also can be characterized as a delayed release, extended release, sustained release, or otherwise modified release with respect to immediate release forms of a corresponding API composition, significantly modifying the release profile as indicated by the given characterization.

In aspects, the invention provides a method of using any one or more of the inventive compositions described herein as a component in an irrigation solution (the administered irrigation solution being a combination composition comprising the inventive composition plus one or more additional combination components). In aspects, such an irrigation solution is applied to an eye during an ophthalmic intervention. In aspects, the invention provides a method of (1) preventing significant inflammation during or after an ophthalmologically-related procedure, (2) maintaining suitable pupil size (e.g., preventing significant intraoperative miosis) during an ophthalmologically-related procedure, (3) detectably or significantly reducing postoperative ocular pain following an ophthalmologically-related procedure, or (4) any combination of (1)-(3). In aspects, the method comprises application of a composition comprising pharmaceutically acceptable amounts of each of one or more ketorolac compounds and one or more phenylephrine compounds during such an ophthalmologically-related procedure, for a period of time after such an ophthalmologically-related procedure, or both. In aspects, the applied composition used in the method lacks a buffer component wherein (1) a buffer is a combination of a weak base and its conjugate acid, a weak acid and its conjugate base, or both; (2) wherein acid and base pairs of a buffer component are present in concentrations of within 10× of one another; (3) wherein the pKa of a buffer component is between 4.3-8.3, such as the pKa of any such buffer component is between 5.3-7.3, e.g., between about 6.0 and 6.6; or (4) wherein, when the ophthalmologically suitable composition is at a pH of 6.3, the acid and base pairs of a buffer component can prevent a change in pH of the composition of more than 2% when 0.1 moles of HCl or 0.1 moles of NaOH are added to 1 L of the composition. In aspects, the composition used in the method maintains a pH of between 5.5-7 and retains at least 97% of the one or more ketorolac compounds and at least 97% of the one or more phenylephrine compounds when stored at 25° C.+/−2° C. for at least one month, such as, e.g., ~2 months, ~3 months, ~4 months, ~5 months, or, e.g., ~6 months (e.g., ≥12 mos., ≥24 mos., ≥30 mos., or ≥36 months). In aspects, the composition used in the method is a carrier composition. In aspects, the carrier composition used in the method is further diluted prior to use. In aspects, the carrier composition used in the method is added to an irrigation solution prior to administration, e.g., it is administered as a combination composition.

In aspects, the invention provides a method of use of the preceding paragraph, wherein any one or more of the compositions used in the method are made according to a process/method of manufacturing provided by the invention as described herein. In aspects, the invention provides the method of use of the preceding paragraph wherein the method comprises providing the any one or more compositions for use in the method as a kit provided by the invention as described herein.

In aspects, the invention provides a method of using the invention composition(s) described herein, wherein the composition used in the method is delivered to the eye in a controlled manner, e.g., a drop-by-drop manner, in a controlled stream of composition, such as, e.g., the pressure and volume of composition in the stream of composition is controllable by the user administering the composition(s), or, e.g., the composition is delivered to the eye as an ophthalmic irrigation solution (e.g., as a component of a combined composition) and is administered using standard ophthalmic irrigation procedures and equipment known in the art.

Methods of Treatment

In aspects, the invention provides methods of treating or preventing ocular inflammation in a patient undergoing or having undergone an ophthalmologically-related procedure comprising administration of one or more compositions described herein. In aspects, the invention provides a method of treating a patient in need of (e.g., as determined through medical diagnosis) modifying/maintaining suitable pupil size. Increasing pupil size, as would be known in the art, means, e.g., increasing pupil size on average or in a significant number of subjects by 5-20%, 5-25%, 5-15%, 5-12.5%, 7.5-15%, 7.5-12.5%, etc., or providing an average pupil size on average or in a significant number of patients of about 6.8 mm-~8 mm, e.g., about 7 mm-~8 mm, e.g., about 7.1 mm-~7.9 mm, about 7.2 mm-~7.9 mm, about 7.3 mm-~7.9 mm, about 7.4 mm-~7.9 mm, about 7.3 mm-~7.8 mm, about 7.4 mm-~7.8 mm, about 7.25 mm-~7.75 mm, or about 7.35 mm-~7.75 mm. In aspects, such a patient is a patient in need of e.g., prevention of significant intraoperative miosis which negatively impacts the effectiveness of an ophthalmic intervention (e.g., an ophthalmologically-related surgical procedure). In aspects, the invention provides a method of treating a patient suffering from significant ocular pain following an ocular intervention.

In aspects, the invention provides a method of treating a patient suffering from or at risk of suffering from inflammation due to an ophthalmologically-related procedure, suffering from or at risk of suffering from significant intraoperative miosis during an ophthalmologically-related procedure, suffering from or at risk of suffering from significant postoperative ocular pain following an ophthalmologically-related procedure, or any combination thereof.

In aspects, the invention provides a method of treating a patient during an ophthalmic surgery to maintain clinically suitable pupil dilation required for the procedure, to prevent clinically significant inflammation during, after, or both during and after the procedure, and to prevent significant post-operative ocular pain.

In aspects, the invention provides a method of treating or preventing a disease or condition benefiting from a combination therapy of an anti-inflammatory and mydriatic compound.

In aspects, the method(s) of treatment or prevention described herein (e.g., described in this section) comprise application of an effective amount of a composition during such an ophthalmologically-related procedure or treatment, for a period of time after such an ophthalmologically-related procedure or treatment, or both, comprising pharmaceutically acceptable amounts of each of one or more ketorolac compounds and one or more phenylephrine compounds. In aspects, compositions used in the method(s) lack a buffer component. In aspects, composition used in the method(s) lack a buffer component, e.g., wherein (1) a buffer is a combination of a weak base and its conjugate acid, a weak acid and its conjugate base, or both; (2) wherein the acid and base pairs of a buffer component are present in concentrations of within 10× of one another; (3) wherein the pKa of a buffer component is between 4.3-8.3, such as the pKa of any such buffer component is between 5.3-7.3, e.g., between about 6.0 and 6.6; or (4) wherein, when the ophthalmologically suitable composition is at a pH of 6.3, the acid and base pairs of a buffer component can prevent a change in pH of the composition of more than 2% when 0.1 moles of HCl or 0.1 moles of NaOH are added to 1 L of the composition. In aspects, compositions used in the method(s) maintain a pH of between 5.5-7 and retain at least 97% of the one or more ketorolac compounds and at least 97% of the one or more phenylephrine compounds when stored at 25° C.+/−2° C. for at least one month, such as, e.g., ~2 months, ~3 months, ~4 months, ~5 months, or, e.g., ~6 months (e.g., 6-36, 12-36, 12-30, 18-36, or 18-30 months (mos.)) or, e.g., when stored under accelerated conditions of, e.g., about 40° C. and 75% RH. In aspects, compositions used in the method(s) are carrier compositions. In aspects, the carrier compositions used in the method(s) are further diluted prior to use (e.g., diluted by ≥50×, ≥85×, ≥100×, ≥~110×, ≥~120×, or ~125×, e.g., about 100-150×, about 110-140×, or about 115-135×). In aspects, carrier compositions used in the method(s) are added to irrigation solutions (that is, they are added to combination components to form combination compositions) prior to administration, e.g., it is administered as a combination composition.

In aspects, the invention provides the method(s) of treatment (or prevention) described herein, e.g., in this section, wherein the compositions further comprise one or more characteristics described elsewhere herein, such as comprising one or more additional excipients, one or more additional APIs, or both, such as comprising, e.g., one or more chelating agents such as an ethylenediaminetetraacetic acid (EDTA) compound or salt thereof. In aspects, such compositions can comprise one or more carriers, such as, e.g., an aqueous carrier, e.g., WFI.

In aspects, the invention provides the method(s) of treatment (or prevention) described herein, e.g., in this section, wherein the ophthalmologically-related procedure/ophthalmic procedure is selected from a group comprising cataract surgery and intraocular lens replacement.

In aspects, the invention provides the method(s) of treatment (or prevention) described herein, e.g., in this section, wherein any one or more of the compositions used in the method(s) are made according to a process or method of manufacturing described herein.

In aspects, the invention provides the method(s) of treatment (or prevention) described herein, e.g., in this section, wherein any one or more compositions used in the method(s) are provided for use in the method as a component of a kit as described herein.

In aspects, the invention provides the method(s) of treatment (or prevention) described herein, e.g., in this section, wherein the compositions used in the method(s) are delivered to the eye in a controlled manner, such as, e.g., in a drop-by-drop manner or, e.g., in a controlled stream of composition, such as, e.g., the pressure and volume of composition in the stream of composition is controllable by the user administering the composition(s). In aspects, the invention provides the method(s) of treatment (or prevention) described herein, e.g., in this section, wherein the compositions are delivered to the eye as an ophthalmic irrigation solution and are administered using standard ophthalmic irrigation procedures of the art. In aspects, the invention provides the method(s) of treatment (or prevention) described herein, e.g., in this section, wherein the compositions are diluted prior to use. In aspects, the invention provides the method(s) of treatment (or prevention) described herein, e.g., in this section, wherein the compositions are added to a separately provided ophthalmic irrigation solution prior to use.

In aspects, the invention provides the method(s) of treatment (or prevention) described herein, e.g., in this section wherein the composition(s) are administered once, twice, or three times per day, e.g., ~1-~5 times per day, ~1-~4, ~1-~3 or ~1-~2, e.g., ~2-~5, ~3-~5, or ~4-~5 times per day, e.g., ~2-~3 times per day for a period of about 1 to about 5 days, e.g., ~1-~4, ~1-~3, or about 1 to about 2 days.

In aspects, the invention provides the method(s) of treatment (or prevention) of any one or more of the paragraphs of this section, wherein treatment with an effective amount of the composition(s) provides detectably or significantly fewer side effects selected from a group comprising eye irritation, posterior capsule opacification, increased intraocular pressure, and anterior chamber inflammation than treatment with OMIDRIA or a similar reference product for the same or similar indication and for at least substantially the same administration period.

In aspects, the application of the method(s) herein result(s) in 1) the prevention of inflammation during or after an ophthalmologically-related procedure, (2) the maintenance of suitable pupil size (e.g., prevention of significant intraoperative miosis) during an ophthalmologically-related procedure, (3) a reduction in postoperative ocular pain following an ophthalmologically-related procedure, or (4) any combination thereof which is at least statistically similar to or better than (e.g., improved over) that resulting from the administration of the product approved by the United States Food and Drug Administration (FDA) under NDA number 205388 and the trademark OMIDRIA® and sold under such registered trademark in the United States prior to the submission of this disclosure or a reference product approved by FDA under NDA number 205388 or a substantially similar product.

Exemplary Technical Effects

Skilled persons will recognize that the compositions and methods of the invention afford several technical effects, providing tool(s) which have heretofore not been available or solving several problems which have heretofore not been addressed or addressed in a similar or sufficient manner by known systems/methods, by use of the various technical features of this disclosure. Various technical effects are described elsewhere in this disclosure, and a few specific technical effects are highlighted/reinforced here.

One exemplary technical effect of the invention is overcoming the problem of being able to administer a stable pharmaceutically acceptable and ophthalmologically suitable composition comprising an anti-inflammatory agent such as a ketorolac compound and a mydriatic agent such as a phenylephrine compound, such a composition lacking a buffering capacity such that the composition is pH adaptable to other compositions to which it may be added or to the environment to which it is applied.

In aspects, one technical effect of the invention is providing for a composition which is shelf stable, capable of 1) maintaining at least about 98% of each of an anti-inflammatory active pharmaceutical ingredient, e.g., a ketorolac compound, such as ketorolac tromethamine, and a mydriatic active pharmaceutical ingredient, e.g., a phenylephrine compound, such as phenylephrine HCl, and 2) capable of maintaining a level of impurities of less than 0.5%, at a period of at least 2 months, such as, e.g., at least about 3 months, when stored at about 25° C. and about 60% relative humidity or under accelerated conditions of about 40° C. and about 75% relative humidity. In aspects, another technical effect of the invention is providing for a composition which is shelf stable, capable of (1) maintaining a level of 1-(3-hydroxyphenyl)-2-(methylamino) ethan-1-one hydrochloride at or below 0.4%, (2) maintaining a level of 5-benzoyl-2,3-dihydro-1H-pyrrolizine-1H-one at or below 0.4%, or (3) maintaining a level of the two specific impurities of (1) and (2) together (e.g., in sum) at or below 0.4% for a period of at least 2 months, such as, e.g., at least about 3 months, ~4, ~5, ~6, ~8, ~12, ~16, ~20, ~24, ~28, ~32, or at least about 36 months, when stored at about 25° C. and about 60% relative humidity or under accelerated conditions of about 40° C. and about 75% relative humidity.

In aspects, another technical effect of the invention is providing for a composition which is shelf stable, capable of maintaining a total level of impurities of less than 0.5%, at a period of at least 2 months, such as, e.g., at least about 3 months, ~4, ~5, ~6, ~8, ~12, ~16, ~20, ~24, ~28, ~32, or at least about 36 months, when stored at about 25° C. and about 60% relative humidity or under accelerated conditions of about 40° C. and about 75% relative humidity.

In aspects, another technical effect of the invention is providing for a composition which is shelf stable, capable of maintaining a pH of between about 5-8, e.g., ~5-~7 or, e.g., ~5.5-~6.8 or ~6-~6.8, for a period of at least 2 months, such as, e.g., at least about 3 months, ~4, ~5, ~6, ~8, ~12, ~16, ~20, ~24, ~28, ~32, or at least about 36 months, when stored at about 25° C. and about 60% relative humidity or under accelerated conditions of about 40° C. and about 75% relative humidity.

In aspects, a technical effect of the invention is providing a stable pharmaceutically acceptable and ophthalmologically suitable composition comprising an anti-inflammatory agent, e.g., a ketorolac compound, and a mydriatic agent, e.g., a phenylephrine compound, such a composition lacking a buffering capacity, e.g., such that the composition is free of a buffer component wherein the buffer component (1) is a combination of a weak base and its conjugate acid, a weak acid and its conjugate base, or both; (2) comprises acid and base pairs present in concentrations of within 10× of one another; (3) comprises a pKa between 4.3-8.3, such as the pKa of any such buffer component is between 5.3-7.3, e.g., between about 6.0 and 6.6; and (4) wherein, when the composition is at a pH of 6.3, the acid and base pairs of the buffer component can prevent a change in pH of the composition of more than 2% when 0.1 moles of HCl or 0.1 moles of NaOH are added to 1 L of the composition, and wherein the composition is capable having its pH easily adapted to that of a composition to which it is added or having its pH easily modified by an environment to which it is added.

Aspects of technical features include compositions which provide anti-inflammatory agent(s), e.g., one or more ketorolac compounds, e.g., ketorolac tromethamine, in combination with mydriatic agent(s), e.g., one or more phenylephrine compounds, e.g., phenylephrine HCl, in a fixed ratio, such as, e.g., about 1:3 ketorolac tromethamine phenylephrine HCl, wherein the composition lacks a buffer component characterizable as 1) a combination of a weak base and its conjugate acid, a weak acid and its conjugate base, or both; 2) able to prevent a significant change in pH upon the addition of an amount (e.g., an otherwise pH-modifying-effective amount) of either a strong acid or a strong base (e.g., such a composition can neutralize the addition of a small amount of a strong acid or a strong base); 3) capable of providing the composition the ability to resist a significant change in its pH when a significant amount of H+ or OH− ions (or otherwise effective amount of such ions) are added or removed owing to other reaction(s) occurring within the same solution; 4) a combination of a weak base and its conjugate acid, a weak acid and its conjugate base, or both, wherein the acid and base pairs of such a buffer component are present in concentrations of within 10× of one another; 5) a combination of a weak base and its conjugate acid, a weak acid and its conjugate base, or both, wherein a pKa of any such buffer component is between 4.3-8.3, such as the pKa of any such buffer component is between 5.3-7.3, e.g., between about 6.0 and 6.6; or 6) when the composition is at a pH of ~6.3, the acid and base pairs of such a buffer component can prevent a change in pH of the composition of ≥2% when 0.1 moles of HCl or 0.1 moles of NaOH are added to 1 L of the composition.

EXEMPLARY ASPECTS OF THE INVENTION

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may make reference to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of both aspect 1 and aspect 2).

Lists of aspects describing specific exemplary embodiments of the invention are sometimes employed for aiding the reader in understanding the invention. Such aspects can, within them, reference other exemplary aspects, either individually or as groups of aspects (e.g., via reference to a range within a list of numbered aspects when such aspects are provided as a numbered list). Reference to ranges of aspects should be interpreted as referencing all such aspects individually, each as unique embodiments of the invention, and in combination with one another as unique embodiment(s) of the invention, according to the presentation provided of such aspects unless such an aspect within such a referenced range is either contradictory or non-sensical. If contradicted, reference to the contradictory aspect should be excluded.

The following is a non-limiting list of exemplary aspects of the invention.

I. COMPOSITION(S)

In aspects, the invention provides a pharmaceutically acceptable composition (e.g., a pharmaceutically acceptable core composition or pharmaceutically acceptable carrier composition) for use in treating or preventing ophthalmic conditions, diseases, or for use in related procedures, comprising pharmaceutically acceptable amounts of each of one or more ophthalmologically suitable ketorolac compounds and one or more ophthalmologically suitable phenylephrine compounds, wherein the composition lacks a buffer component wherein (1) the buffer is a combination of a weak base and its conjugate acid, a weak acid and its conjugate base, or both; (2) wherein the acid and base pairs of such a buffer component are present in concentrations of within 10× of one another; (3) wherein the pKa of any such buffer component is between 4.3-8.3, such as the pKa of any such buffer component is between 5.3-7.3, e.g., between about 6.0 and 6.6; and (4) wherein, when the composition is at a pH of 6.3, the acid and base pairs of the buffer component can prevent a change in pH of the composition of more than 2% when 0.1 moles of HCl or 0.1 moles of NaOH are added to 1 L of the composition (aspect 1).

In aspects, the invention provides a pharmaceutically acceptable composition (e.g., a pharmaceutically acceptable core composition or pharmaceutically acceptable carrier composition) for use in treating or preventing ophthalmic conditions, diseases, or for use in related procedures, comprising pharmaceutically acceptable amounts of each of one or more ophthalmologically suitable ketorolac compounds and one or more ophthalmologically suitable phenylephrine compounds, wherein the composition (1) lacks a buffer component wherein (a) the buffer is a combination of a weak base and its conjugate acid, a weak acid and its conjugate base, or both; (b) wherein the acid and base pairs of such a buffer component are present in concentrations of within 10× of one another; (c) wherein the pKa of any such buffer component is between 4.3-8.3, such as the pKa of any such buffer component is between 5.3-7.3, e.g., between about 6.0 and 6.6; and (d) wherein, when the ophthalmologically suitable composition is at a pH of 6.3, the acid and base pairs of the buffer component can prevent a change in pH of the composition of more than 2% when 0.1 moles of HCl or 0.1 moles of NaOH are added to 1 L of the composition; and (2) maintains a pH of between 5.5 and 7 when stored at 25° C.+/−2° C. for at least about one month (e.g., ≥2, ≥3, ≥6, ≥12, ≥16, ≥20, or ≥24 months) (aspect 2).

In aspects, the invention provides a pharmaceutically acceptable composition (e.g., pharmaceutically acceptable core composition or pharmaceutically acceptable carrier composition) for use in treating or preventing ophthalmic conditions, diseases, or for use in related procedures, comprising pharmaceutically acceptable amounts of each of one or more ophthalmologically suitable ketorolac compounds and one or more ophthalmologically suitable phenylephrine compounds, wherein the composition (1) lacks a buffer component wherein (a) the buffer is a combination of a weak base and its conjugate acid, a weak acid and its conjugate base, or both; (b) wherein the acid and base pairs of such a buffer component are present in concentrations of within 10× of one another; (c) wherein the pKa of any such buffer component is between 4.3-8.3, such as the pKa of any such buffer component is between 5.3-7.3, e.g., between about 6.0 and 6.6; and (d) wherein, when the ophthalmologically suitable composition is at a pH of 6.3, the acid and base pairs of the buffer component can prevent a change in pH of the composition of more than 2% when 0.1 moles of HCl or 0.1 moles of NaOH are added to 1 L of the composition; (2) maintains a pH of between 5.5-7; and (3) retains at least 97% of the one or more ketorolac compounds and at least 97% of the phenylephrine compound(s) when stored at 25° C.+/−2° C. for at least about one month (e.g., ≥2, 3, 6, 12, or ≥24 months) (aspect 3).

In aspects, the invention provides an acceptable composition (e.g., pharmaceutically acceptable core composition or pharmaceutically acceptable carrier composition) for use in treating or preventing ophthalmic conditions, diseases, or for use in related procedures, comprising pharmaceutically acceptable amounts of each of one or more ophthalmologically suitable ketorolac compounds and ophthalmologically suitable phenylephrine compound(s), wherein the composition (1) lacks a buffer component wherein (a) the buffer is a combination of a weak base and its conjugate acid, a weak acid and its conjugate base, or both; (b) wherein the acid and base pairs of such a buffer component are present in concentrations of within 10× of one another; (c) wherein the pKa of any such buffer component is between 4.3-8.3, such as the pKa of any such buffer component is between 5.3-7.3, e.g., between about 6.0 and 6.6; and (d) wherein, when the ophthalmologically suitable composition is at a pH of 6.3, the acid and base pairs of the buffer component can prevent a change in pH of the composition of more than 2% when 0.1 moles of HCl or 0.1 moles of NaOH are added to 1 L of the composition; (2) maintains a pH of between 5.5-7 when stored at 25° C.+/−2° C. for at least about one month (e.g., ≥2, 3, 6, 12, or ≥24 months); (3) retains at least 97% of the one or more ketorolac compounds and at least 97% of the one or more phenylephrine compounds when stored at 25° C.+/−2° C. for at least about one month (e.g., ≥2, 3, 6, 12, or ≥24 months); and (4) lacks any component characterizable as a chelating agent (e.g., does not comprise a chelating agent) (aspect 4).

Ketorolac Compound(s)

In aspects, the invention provides the pharmaceutically acceptable composition of any one or more of aspects 1-4, wherein the composition comprises a single type of ophthalmologically suitable ketorolac compound (aspect 5).

In aspects, the invention provides the pharmaceutically acceptable composition of any one or more of aspects 1-5, wherein the ophthalmologically suitable ketorolac compound comprises a salt of ketorolac (aspect 6).

In aspects, the invention provides the pharmaceutically acceptable composition of any one or more of aspects 1-6, wherein the ophthalmologically suitable ketorolac compound is ketorolac tromethamine (aspect 7).

In aspects, the invention provides the pharmaceutically acceptable composition of any one or more of aspects 1-7, wherein the ophthalmologically suitable ketorolac compound is present in the composition in an amount of between about 0.1-about 5.0 wt/v. % (aspect 8).

In aspects, the invention provides the pharmaceutically acceptable suitable composition of any one or more of aspects 1-8, wherein the ophthalmologically suitable ketorolac compound is present in the composition in an amount of between about 0.1-about 4.0 wt/v. % (aspect 9).

In aspects, the invention provides the pharmaceutically acceptable composition of any one or more of aspects 1-9, wherein the ophthalmologically suitable ketorolac compound is present in the composition in an amount of between about 0.1-about 3.0 wt/v. % (aspect 10).

In aspects, the invention provides the pharmaceutically acceptable composition of any one or more of aspects 1-10, wherein the ophthalmologically suitable ketorolac compound is present in the composition in an amount of between about 0.1-about 2.0 wt/v. % (aspect 11).

In aspects, the invention provides the pharmaceutically acceptable composition of any one or more of aspects 1-11, wherein the ophthalmologically suitable ketorolac compound is present in the composition in an amount of between about 0.1-about 1.0 wt/v. % (aspect 12).

In aspects, the invention provides the pharmaceutically acceptable composition of any one or more of aspects 1-12, wherein the ophthalmologically suitable ketorolac compound is present in the composition in an amount of between about 0.1-about 0.5 wt/v. % (aspect 13).

In aspects, the invention provides the pharmaceutically acceptable composition of any one or more of aspects 1-13, wherein the ophthalmologically suitable ketorolac compound is present in the composition of between about 0.3-about 0.5 wt/v. % (aspect 14).

Phenylephrine Compound(s)

In aspects, the invention provides the pharmaceutically acceptable composition of any one or more of aspects 1-14, wherein the composition comprises a single type of ophthalmologically suitable phenylephrine compound (aspect 15).

In aspects, the invention provides the pharmaceutically acceptable composition of any one or more of aspects 1-15, wherein the ophthalmologically suitable phenylephrine compound comprises a phenylephrine salt (aspect 16).

In aspects, the invention provides the pharmaceutically acceptable composition of any one or more of aspects 1-16, wherein the ophthalmologically suitable phenylephrine compound is phenylephrine hydrochloride (phenylephrine HCl) (aspect 17).

In aspects, the invention provides pharmaceutically acceptable compositions of any one or more of aspects 1-17, wherein the phenylephrine compound is present in the composition in an amount of between about 0.1-about 10.0 wt/v. % (aspect 18).

In aspects, the invention provides a composition of any one or more of aspects 1-18, wherein the ophthalmologically suitable phenylephrine compound is present in the composition in an amount of between about 0.1-about 8.0 wt/v. % (aspect 19).

In aspects, the invention provides a composition of any one or more of aspects 1-19, wherein the ophthalmologically suitable phenylephrine compound is present in the composition in an amount of between about 0.1-about 6.0 wt/v. % (aspect 20).

In aspects, the invention provides a composition of any one or more of aspects 1-20, wherein the ophthalmologically suitable phenylephrine compound is present in the composition in an amount of between about 0.1-about 4.0 wt/v. % (aspect 21).

In aspects, the invention provides a composition of any one or more of aspects 1-21, wherein the ophthalmologically suitable phenylephrine compound is present in the composition in an amount of between about 0.1-about 2.0 wt/v. % (aspect 22).

In aspects, the invention provides a composition of any one or more of aspects 1-22, wherein the ophthalmologically suitable phenylephrine compound is present in the composition in an amount of between about 0.5-about 1.5 wt/v. % (aspect 23).

In aspects, the invention provides a composition of any one or more of aspects 1-23, wherein the ophthalmologically suitable phenylephrine compound is present in the composition in an amount of between about 1.0-about 1.5% (aspect 24).

Combinations of Ketorolac and Phenylephrine Compounds

In aspects, the invention provides pharmaceutically acceptable suitable compositions of any one or more of aspects 1-24, wherein the ratio of the amount of ophthalmologically suitable ketorolac compound(s) to ophthalmologically suitable phenylephrine compound(s) is between about 1:1-about 1:13 (aspect 25).

In aspects, the invention provides pharmaceutically acceptable compositions of any one or more of aspects 1-25, wherein the ratio of the amount of ophthalmologically suitable ketorolac compound(s) to ophthalmologically suitable phenylephrine compound(s) is between about 1:1-about 1:10 (aspect 26).

In aspects, the invention provides pharmaceutically acceptable compositions of any one or more of aspects 1-26, wherein the ratio of the amount of ophthalmologically suitable ketorolac compound(s) to ophthalmologically suitable phenylephrine compound(s) is between about 1:1-about 1:8 (aspect 27).

In aspects, the invention provides pharmaceutically acceptable compositions of any one or more of aspects 1-27, wherein the ratio of the amount of ophthalmologically suitable ketorolac compound(s) to ophthalmologically suitable phenylephrine compound(s) is between about 1:1-about 1:6 (aspect 28).

In aspects, the invention provides pharmaceutically acceptable compositions of any one or more of aspects 1-28, wherein the ratio of the amount of ophthalmologically suitable ketorolac compound(s) to ophthalmologically suitable phenylephrine compound(s) is between about 1:1-about 1:5 (aspect 29).

In aspects, the invention provides pharmaceutically acceptable compositions of any one or more of aspects 1-29, wherein the ratio of the amount of ophthalmologically suitable ketorolac compound(s) to ophthalmologically suitable phenylephrine compound(s) is between about 1:2-about 1:4 (aspect 30).

In aspects, the invention provides pharmaceutically acceptable compositions of any one or more of aspects 1-30, wherein the ratio of the amount of ketorolac compound(s) to phenylephrine compound(s) is about 1:3 (aspect 31).

In aspects, the invention provides pharmaceutically acceptable compositions of any one or more of aspects 1-31, wherein the composition comprises between ~0.1-about 0.5% ketorolac tromethamine and between about 1.0-about 1.5% phenylephrine HCl (aspect 32).

pH Characteristics

In aspects, the invention provides pharmaceutically acceptable compositions of any one or more of aspects 1-32, wherein the ophthalmologically suitable composition has a pH of between about 5.0-about 8.0 (aspect 33).

In aspects, the invention provides pharmaceutically acceptable compositions of any one or more of aspects 1-33, wherein the composition has a pH of ~5.3-7.3 (aspect 34).

In aspects, the invention provides pharmaceutically acceptable compositions of any one or more of aspects 1-34, wherein the composition has a pH of ~5.6-~7.0 (aspect 35).

In aspects, the invention provides pharmaceutically acceptable compositions of any one or more of aspects 1-35, wherein the composition has a pH of ~5.9-~6.7 (aspect 36).

In aspects, the invention provides pharmaceutical compositions of any one or more of aspects 1-36, wherein the composition has a pH of ~6.1-about 6.5 (aspect 37).

In aspects, the invention provides compositions of any one or more of aspects 1-37, wherein the composition has a pH of between about 6.2-about 6.4 (aspect 38).

In aspects, the invention provides pharmaceutically acceptable compositions of any one or more of aspects 1-38, wherein the composition has a pH of about 6.3 (aspect 39).

In aspects, the invention provides pharmaceutically acceptable compositions of any one or more of aspects 1-39, wherein the composition lacks a suitable amount of any buffer such that the pH of the composition is modified within a period of less than about 30 seconds to the pH of that of the environment to which it is added (e.g., to the pH of a component of an irrigation solution, to the pH of an irrigation solution, or to the pH of an eye to which the composition is added) (aspect 40).

In aspects, the invention provides pharmaceutically acceptable compositions of aspect 40, wherein the pH of the composition is modified within a period of less than about 20 seconds to the pH of that of the environment to which it is added (aspect 41).

In aspects, the invention provides compositions of any one or both of aspects 40 and aspect 41, wherein the pH of the composition is modified with a period of less than about 10 seconds to the pH of that of the environment to which it is added (aspect 42).

In aspects, the invention provides pharmaceutically acceptable compositions of any one or more of aspects 40-42, wherein the pH of the composition is modified with a period of less than about 5 seconds to the pH of that of the environment to which it is added (aspect 43).

In aspects, the invention provides pharmaceutically acceptable compositions of any one or more of aspects 40-43, wherein the pH of the composition is modified with a period of less than about 1 second to the pH of that of the environment to which it is added (aspect 44).

Stability Characteristics

In aspects, the invention provides pharmaceutically acceptable compositions of any one or more of aspects 1-44, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about one month (aspect 45).

In aspects, the invention provides pharmaceutically acceptable compositions of any one or more of aspects 1-45, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 5 weeks (aspect 46).

In aspects, the invention provides pharmaceutically acceptable compositions of any one or more of aspects 1-46, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 6 weeks (aspect 47).

In aspects, the invention provides pharmaceutically acceptable compositions of any one or more of aspects 1-47, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 2 months (aspect 48).

In aspects, the invention provides pharmaceutically acceptable compositions of any one or more of aspects 1-48, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 10 weeks (aspect 49).

In aspects, the invention provides pharmaceutically acceptable compositions of any one or more of aspects 1-49, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 3 months (aspect 50).

In aspects, the invention provides pharmaceutically acceptable compositions of any one or more of aspects 1-50, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 4 months (aspect 51).

In aspects, the invention provides pharmaceutically acceptable compositions of any one or more of aspects 1-51, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 5 months (aspect 52).

In aspects, the invention provides pharmaceutically acceptable compositions of any one or more of aspects 1-52, wherein the composition retains at least 97% of the one or more ophthalmologically suitable ketorolac compounds and at least 97% of the one or more ophthalmologically suitable phenylephrine compounds when stored at 25° C.+/−2° C.; about 25° C. and about 60% relative humidity; about 40° C. and about 75% relative humidity; or any combination thereof for at least about 6 months, e.g., ≥~6, ≥~8, ≥~10, ≥~12, ≥~15, ≥~18, ≥~21, ≥~24, ≥~27, or ≥~30 months, e.g., ~6-~36 mos. (aspect 53).

In aspects, the invention provides pharmaceutically acceptable compositions of any one or more of aspects 1-53, wherein the composition contains (a) less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 1 month (aspect 54).

In aspects, the invention provides pharmaceutically acceptable compositions of any one or more of aspects 1-54, wherein the composition contains (a) less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 6 weeks (aspect 55).

In aspects, the invention provides pharmaceutically acceptable compositions of any one or more of aspects 1-55, wherein the composition contains less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 2 months (aspect 56).

In aspects, the invention provides pharmaceutically acceptable compositions of any one or more of aspects 1-56, wherein the composition contains less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 10 weeks (aspect 57).

In aspects, the invention provides pharmaceutically acceptable compositions of any one or more of paragraphs aspects 1-57, wherein the composition contains less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 3 months (aspect 58).

In aspects, the invention provides pharmaceutically acceptable compositions of any one or more of aspects 1-58, wherein the composition contains less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 4 months (aspect 59).

In aspects, the invention provides pharmaceutically acceptable compositions of any one or more of aspects 1-59, wherein the composition contains less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 5 months (aspect 60).

In aspects, the invention provides pharmaceutically acceptable compositions of any one or more of aspects 1-60, wherein the composition contains less than about 2.5%, less than about 2%, less than about 1.5%, less than about 1%, or less than about 0.5% total impurities; (b) less than about 0.6%, less than about 0.5%, or less than about 0.4% of the phenylephrine impurity 1-(3-hydroxyphenyl)-2-(methylamino) ethan-1-one hydrochloride; (c) less than less than about 0.6%, less than about 0.5%, or less than about 0.4% of the ketorolac impurity 5-benzoyl-2,3-dihydro-1H-pyrrolizine-1-one; or (d) any combination of (a)-(c) after storage at about room temperature (e.g., at about 25° C.+/−2° C.), about 25° C. and about 60% relative humidity, about 40° C. and about 75% relative humidity, or any combination thereof, for at least about 6 months, e.g., ≥~6, ≥~8, ≥~10, ≥~12, ≥~15, ≥~18, ≥~21, ≥~24, ≥~27, or ≥~30 months, e.g., ~6-~36 mos. (aspect 61).

Additional Ingredients

In aspects, the invention provides pharmaceutically acceptable compositions of any one or more of aspects 1-61, wherein the composition comprises one or more additional ophthalmologically suitable excipients, one or more additional ophthalmologically suitable active pharmaceutical ingredients (APIs), or both (aspect 62).

Additional Excipients

In aspects, the invention provides pharmaceutically acceptable compositions of aspect 62, wherein the composition comprises one or more ophthalmologically suitable excipients selected from a group comprising chelating agent(s), antioxidant(s), tonicity agent(s), pH-adjusting agent(s), preservative(s), thickening agent(s)/viscosity enhancer(s), solubilizer(s), penetration enhancer(s), and carrier(s) (aspect 63).

In aspects, the invention provides pharmaceutically acceptable compositions of any one or both of aspect 62 and aspect 63, wherein the composition comprises one or more of an ophthalmologically suitable chelating agent, antioxidant, tonicity agent, pH-adjusting agent, preservative, or carrier (aspect 64).

Chelating Agents

In aspects, the invention provides pharmaceutically acceptable compositions of any one or more of aspects 62-42, wherein the composition comprises one or more chelating agents that detectably or significantly improves the stability of the ketorolac compound(s), detectably or significantly improves the stability of the phenylephrine compound(s), enhances preservative(s) effectiveness, or any or all thereof, at a period of 2 weeks or more of storage at about room temperature (e.g., at about 25° C.+/−2° C.), about 25° C. and about 60% relative humidity, about 40° C. and about 75% relative humidity, or any combination thereof post-manufacturing (aspect 65).

In aspects, the invention provides pharmaceutically acceptable compositions of any one or more of aspects 62-65, wherein the composition comprises one or more ophthalmologically suitable chelating agents that detectably or significantly improves the stability of the ketorolac compound(s), detectably or significantly improves the stability of the phenylephrine compound(s), enhances preservative(s) effectiveness, or any or all thereof, at a period of 3 weeks or more of storage at about room temperature (e.g., at about 25° C.+/−2° C.), about 25° C. and about 60% relative humidity, about 40° C. and about 75% relative humidity, or any combination thereof post-manufacturing (aspect 66).

In aspects, the invention provides pharmaceutically acceptable compositions of any one or more of aspects 62-66, wherein the composition comprises one or more ophthalmologically suitable chelating agents that detectably or significantly improves the stability of the ketorolac compound(s), detectably or significantly improve the stability of the phenylephrine compound(s), enhances preservative(s) effectiveness, or any or all thereof, at a period of 1 month or more of storage at about room temperature (e.g., at about 25° C.+/−2° C.), about 25° C. and about 60% relative humidity, about 40° C. and about 75% relative humidity, or any combination thereof post-manufacturing (aspect 67).

In aspects, the invention provides pharmaceutically acceptable compositions of any one or more of aspects 62-67, wherein the composition comprises one or more ophthalmologically suitable chelating agents that detectably or significantly improves the stability of the ketorolac compound, detectably or significantly improves the stability of the phenylephrine compound(s), enhances preservative(s) effectiveness, or any or all thereof, at a period of 6 weeks or more of storage at about room temperature (e.g., at about 25° C.+/−2° C.), about 25° C. and about 60% relative humidity, about 40° C. and about 75% relative humidity, or any combination thereof post-manufacturing (aspect 68).

In aspects, the invention provides pharmaceutically acceptable compositions of any one or more of aspects 62-68, wherein the composition comprises one or more ophthalmologically suitable chelating agents that detectably or significantly improves the stability of the ketorolac compound(s), detectably or significantly improves the stability of the phenylephrine compound(s), enhances preservative effectiveness, or any or all thereof, at a period of 2 months or more of storage at about room temperature (e.g., at about 25° C.+/−2° C.), about 25° C. and about 60% relative humidity, about 40° C. and about 75% relative humidity, or any combination thereof post-manufacturing (aspect 69).

In aspects, the invention provides pharmaceutically acceptable compositions of any one or more of aspects 62-69, wherein the composition comprises one or more ophthalmologically suitable chelating agents that detectably or significantly improves the stability of the ketorolac compound(s), detectably or significantly improves the stability of the phenylephrine compound(s), enhances preservative(s) effectiveness, or any or all thereof, at a period of 10 weeks or more of storage at about room temperature (e.g., at about 25° C.+/−2° C.), about 25° C. and about 60% relative humidity, about 40° C. and about 75% relative humidity, or any combination thereof post-manufacturing (aspect 70).

In aspects, the invention provides pharmaceutically acceptable compositions of any one or more of aspects 62-70, wherein the composition comprises one or more ophthalmologically suitable chelating agents that detectably or significantly improves the stability of the ketorolac compound(s), detectably or significantly improves the stability of the phenylephrine compound(s), enhances preservative(s)

effectiveness, or any or all thereof, at a period of 3 months or more of storage at about room temperature (e.g., at about 25° C.+/−2° C.), about 25° C. and about 60% relative humidity, about 40° C. and about 75% relative humidity, or any combination thereof post-manufacturing (aspect 71).

In aspects, the invention provides pharmaceutically acceptable compositions of any one or more of aspects 62-71, wherein the composition comprises one or more ophthalmologically suitable chelating agents that detectably or significantly improves the stability of the ketorolac compound(s), detectably or significantly improves the stability of the phenylephrine compound(s), enhances preservative(s) effectiveness, or any or all thereof, at a period of 4 months or more of storage at about room temperature (e.g., at about 25° C.+/−2° C.), about 25° C. and about 60% relative humidity, about 40° C. and about 75% relative humidity, or any combination thereof post-manufacturing (aspect 72).

In aspects, the invention provides pharmaceutically acceptable compositions of any one or more of aspects 62-72, wherein the composition comprises one or more ophthalmologically suitable chelating agents that detectably or significantly improves the stability of the ketorolac compound(s), detectably or significantly improves the stability of the phenylephrine compound(s), enhances preservative(s) effectiveness, or any or all thereof, at a period of 5 months or more of storage at about room temperature (e.g., at about 25° C.+/−2° C.), about 25° C. and about 60% relative humidity, about 40° C. and about 75% relative humidity, or any combination thereof post-manufacturing (aspect 73).

In aspects, the invention provides pharmaceutically acceptable compositions of any one or more of aspects 62-73, wherein the composition comprises one or more ophthalmologically suitable chelating agents that detectably or significantly improves the stability of the ketorolac compound(s), detectably or significantly improves the stability of the phenylephrine compound(s), enhances preservative(s) effectiveness, or any or all thereof, at a period of 6 months or more of storage at about room temperature (e.g., at about 25° C.+/−2° C.), about 25° C. and about 60% relative humidity, about 40° C. and about 75% relative humidity, or any combination thereof post-manufacturing, e.g., ≥~6, ≥~8, ≥~10, ≥~12, ≥~15, ≥~18, ≥~21, ≥~24, ≥~27, or ≥~30 months, e.g., ~6-~36 mos. (aspect 74).

In aspects, the invention provides pharmaceutically acceptable compositions of any one or more of aspects 62-74, wherein the composition comprises one or more ophthalmologically suitable chelating agents present in the composition in an amount representing between about 0.001 wt/v. %-about 0.5 wt/v. % of the composition (aspect 75).

In aspects, the invention provides pharmaceutically acceptable compositions of any one or more of aspects 62-75, wherein the composition comprises one or more ophthalmologically suitable chelating agents present in the composition in an amount representing between about 0.001 wt/v. %-about 0.4 wt/v. % of the composition (aspect 76).

In aspects, the invention provides pharmaceutically acceptable compositions of any one or more of aspects 62-76, wherein the composition comprises one or more ophthalmologically suitable chelating agents present in the composition in an amount representing between about 0.001-about 0.3 wt/v. % of the composition (aspect 77).

In aspects, the invention provides pharmaceutically acceptable compositions of any one or more of aspects 62-77, wherein the composition comprises one or more ophthalmologically suitable chelating agents present in the composition in an amount representing between about 0.001-about 0.2 wt/v. % of the composition (aspect 78).

In aspects, the invention provides pharmaceutically acceptable compositions of any one or more of aspects 62-78, wherein composition comprises one or more ophthalmologically suitable chelating agents present in the composition in an amount representing about 0.1 wt/v. % of the composition (aspect 79).

In aspects, the invention provides compositions of any one or more of aspects 62-79, wherein the composition comprises one or more ophthalmologically suitable chelating agents characterizable as a monomeric polyacid (aspect 80).

In aspects, the invention provides pharmaceutically acceptable compositions of aspect 80, wherein the ophthalmologically suitable chelating agent comprises an ethylenediaminetetraacetic acid (EDTA) compound (aspect 81).

In aspects, the invention provides pharmaceutically acceptable compositions of aspect 81, wherein the ophthalmologically suitable chelating agent comprises EDTA or an ophthalmologically suitable salt thereof (aspect 82).

In aspects, the invention provides pharmaceutically acceptable compositions of aspect 82, wherein the ophthalmologically suitable chelating agent is EDTA (aspect 83).

In aspects, the invention provides compositions of aspect 83, wherein composition comprises EDTA in an amount of about 0.1 wt/v. % (aspect 84).

Antioxidants

In aspects, the invention provides pharmaceutically acceptable compositions of any one or more of aspects 62-84, wherein the composition comprises one or more ophthalmologically suitable antioxidants that detectably or significantly improves the stability of the ketorolac compound(s), detectably or significantly improves the stability of the phenylephrine compound(s), enhances preservative(s) effectiveness, or any or all thereof, at a period of 2 weeks or more of storage at about room temperature (e.g., at about 25° C.+/−2° C.), about 25° C. and about 60% relative humidity, about 40° C. and about 75% relative humidity, or any combination thereof post-manufacturing (aspect 85).

In aspects, the invention provides pharmaceutically acceptable compositions of any one or more of aspects 62-85, wherein the composition comprises one or more ophthalmologically suitable antioxidants that detectably or significantly improves the stability of the ketorolac compound(s), detectably or significantly improves the stability of the phenylephrine compound, enhances preservative(s) effectiveness, or any or all thereof, at a period of 3 weeks or more of storage at about room temperature (e.g., at about 25° C.+/−2° C.), about 25° C. and about 60% relative humidity, about 40° C. and about 75% relative humidity, or any combination thereof post-manufacturing (aspect 86).

In aspects, the invention provides pharmaceutically acceptable compositions of any one or more of aspects 62-86, wherein the composition comprises one or more ophthalmologically suitable antioxidants that detectably or significantly improves the stability of the ketorolac compound(s), detectably or significantly improves the stability of the phenylephrine compound(s), enhances preservative(s) effectiveness, or any or all thereof, at a period of 1 month or more of storage at about room temperature (e.g., at about 25° C.+/−2° C.), about 25° C. and about 60% relative humidity, about 40° C. and about 75% relative humidity, or any combination thereof post-manufacturing (aspect 87).

In aspects, the invention provides pharmaceutically acceptable compositions of any one or more of aspects 62-87, wherein the composition comprises one or more ophthalmologically suitable antioxidants that detectably or significantly improves the stability of the ketorolac compound(s), detectably or significantly improves the stability of the phenylephrine compound(s), enhances preservative(s) effectiveness, or any or all thereof, at a period of 6 weeks or more of storage at about room temperature (e.g., at about 25° C.+/−2° C.), about 25° C. and about 60% relative humidity, about 40° C. and about 75% relative humidity, or any combination thereof post-manufacturing (aspect 88).

In aspects, the invention provides pharmaceutically acceptable compositions of any one or more of aspects 62-88, wherein the composition comprises one or more ophthalmologically suitable antioxidants that detectably or significantly improves the stability of the ketorolac compound(s), detectably or significantly improves the stability of the phenylephrine compound, enhances preservative(s) effectiveness, or any or all thereof, at a period of 2 months or more of storage at about room temperature (e.g., at about 25° C.+/−2° C.), about 25° C. and about 60% relative humidity, about 40° C. and about 75% relative humidity, or any combination thereof post-manufacturing (aspect 89).

In aspects, the invention provides pharmaceutically acceptable compositions of any one or more of aspects 62-89, wherein the composition comprises one or more ophthalmologically suitable antioxidants that detectably or significantly improves the stability of the ketorolac compound(s), detectably or significantly improves the stability of the phenylephrine compound(s), enhances preservative(s) effectiveness, or any or all thereof, at a period of 10 weeks or more of storage at about room temperature (e.g., at about 25° C.+/−2° C.), about 25° C. and about 60% relative humidity, about 40° C. and about 75% relative humidity, or any combination thereof post-manufacturing (aspect 90).

In aspects, the invention provides pharmaceutically acceptable compositions of any one or more of aspects 62-90, wherein the composition comprises one or more ophthalmologically suitable antioxidants that detectably or significantly improves the stability of the ketorolac compound(s), detectably or significantly improves the stability of the phenylephrine compound(s), enhances preservative(s) effectiveness, or any or all thereof, at a period of 3 months or more of storage at about room temperature (e.g., at about 25° C.+/−2° C.), about 25° C. and about 60% relative humidity, about 40° C. and about 75% relative humidity, or any combination thereof post-manufacturing (aspect 91).

In aspects, the invention provides pharmaceutically acceptable compositions of any one or more of aspects 62-91, wherein the composition comprises one or more ophthalmologically suitable antioxidants that detectably or significantly improves the stability of the ketorolac compound(s), detectably or significantly improves the stability of the phenylephrine compound(s), enhances preservative(s) effectiveness, or any or all thereof, at a period of 4 months or more of storage at about room temperature (e.g., at about 25° C.+/−2° C.), about 25° C. and about 60% relative humidity, about 40° C. and about 75% relative humidity, or any combination thereof post-manufacturing (aspect 92).

In aspects, the invention provides pharmaceutically acceptable compositions of any one or more of aspects 62-92, wherein the composition comprises one or more ophthalmologically suitable antioxidants that detectably or significantly improves the stability of the ketorolac compound(s), detectably or significantly improves the stability of the phenylephrine compound(s), enhances preservative(s) effectiveness, or any or all thereof, at a period of 5 months or more of storage at about room temperature (e.g., at about 25° C.+/−2° C.), about 25° C. and about 60% relative humidity, about 40° C. and about 75% relative humidity, or any combination thereof post-manufacturing (aspect 93).

In aspects, the invention provides pharmaceutically acceptable compositions of any one or more of aspects 62-93, wherein the composition comprises one or more ophthalmologically suitable antioxidants that detectably or significantly improves the stability of the ketorolac compound(s), detectably or significantly improves the stability of the phenylephrine compound(s), enhances preservative effectiveness, or any or all thereof, at a period of 6 months or more of storage at about room temperature (e.g., at about 25° C.+/−2° C.), about 25° C. and about 60% relative humidity, about 40° C. and about 75% relative humidity, or any combination thereof post-manufacturing, e.g., ≥~6, ≥~8, ≥~10, ≥~12, ≥~15, ≥~18, ≥~21, ≥~24, ≥~27, or ≥~30 months, e.g., ~6-~36 mos. (aspect 94).

In aspects, the invention provides pharmaceutically acceptable compositions of any one or more of aspects 62-94, wherein the composition comprises one or more ophthalmologically suitable antioxidants present in the composition in an amount representing between about 0.001 wt/v. %-about 2 wt/v. % of the composition (aspect 95).

In aspects, the invention provides pharmaceutically acceptable compositions of any one or more of aspects 62-95, wherein the composition comprises one or more ophthalmologically suitable antioxidants present in the composition in an amount representing between about 0.001 wt/v. %-about 1.5 wt/v. % of the composition (aspect 96).

In aspects, the invention provides pharmaceutically acceptable compositions of any one or more of aspects 62-96, wherein the composition comprises one or more ophthalmologically suitable antioxidants present in the composition in an amount representing between about 0.05-about 1 wt/v. % of the composition (aspect 97).

In aspects, the invention provides compositions of any one or more of aspects 62-97, wherein the composition comprises one or more ophthalmologically suitable antioxidants selected from a group comprising sodium ascorbate, ascorbic acid, thiamine, pyridoxine, histidine, cysteine, glutathione and monothioglycerol (aspect 98).

Tonicity Agents

In aspects, the invention provides pharmaceutically acceptable compositions of any one or more of aspects 62-98, wherein the composition comprises one or more ophthalmologically suitable tonicity agents such that the composition comprises an isotonic range (e.g., an osmolality) of between about 200-about 400 mOsm/kg (aspect 99).

In aspects, the invention provides pharmaceutically acceptable compositions of any one or more of aspects 62-99, wherein the composition comprises one or more ophthalmologically suitable tonicity agents such that the composition comprises an isotonic range (e.g., an osmolality) of between about 210-about 390 mOsm/kg (aspect 100).

In aspects, the invention provides pharmaceutically acceptable compositions of any one or more of aspects 62-100, wherein the composition comprises one or more ophthalmologically suitable tonicity agents such that the composition comprises an isotonic range (e.g., an osmolality) of between about 220-about 380 mOsm/kg (aspect 101).

In aspects, the invention provides pharmaceutically acceptable compositions of any one or more of aspects 62-101, wherein the composition comprises one or more ophthalmologically suitable tonicity agents such that the composition comprises an isotonic range (e.g., an osmolality) of between about 230-about 370 mOsm/kg (aspect 102).

In aspects, the invention provides pharmaceutically acceptable compositions of any one or more of aspects 62-102, wherein the composition comprises one or more ophthalmologically suitable tonicity agents such that the composition comprises an isotonic range (e.g., an osmolality) of between about 240-about 360 mOsm/kg (aspect 103).

In aspects, the invention provides pharmaceutically acceptable compositions of any one or more of aspects 62-103, wherein the composition comprises one or more ophthalmologically suitable tonicity agents such that the composition comprises an isotonic range (e.g., an osmolality) of between about 250-about 350 mOsm/kg (aspect 104).

In aspects, the invention provides pharmaceutically acceptable compositions of any one or more of aspects 62-104, wherein the composition comprises one or more ophthalmologically suitable tonicity agents present in the composition in an amount representing between about 0.001 wt/v. %-about 1 wt/v. % of the composition (aspect 105).

In aspects, the invention provides pharmaceutically acceptable compositions of any one or more of aspects 62-105, wherein the composition comprises one or more ophthalmologically suitable tonicity agents present in the composition in an amount representing between about 0.005 wt/v. %-about 0.95 wt/v. % of the composition (aspect 106).

In aspects, the invention provides pharmaceutically acceptable compositions of any one or more of aspects 62-106, wherein the composition comprises one or more ophthalmologically suitable tonicity agents present in the composition in an amount representing between about 0.009 wt/v. %-about 0.9 wt/v. % of the composition (aspect 107).

In aspects, the invention provides pharmaceutically acceptable compositions of any one or more of aspects 62-107, wherein the composition comprises one or more ophthalmologically suitable tonicity agents present in the composition in an amount representing between about 0.01 wt/v. %-about 8 wt/v. % of the composition (aspect 108).

In aspects, the invention provides pharmaceutically acceptable compositions of any one or more of aspects 62-108, wherein the composition comprises a sufficient amount of an ophthalmologically suitable tonicity agent such that the composition has an isotonicity which does not cause clinically significant eye irritation in a significant number of recipients of the composition in an appropriately controlled clinical trial recognized by a prevailing regulatory authority, such as the United States Food and Drug Administration (US FDA) (aspect 109).

pH Adjusting Agents

In aspects, the invention provides compositions of any one or more of aspects 62-109, wherein the composition comprises one or more ophthalmologically suitable acidifying agents, alkalizing agents, or both, used to significantly lower or raise the pH of the composition to a target value during the manufacturing process, which is unaccompanied by a sufficient amount of a corresponding acid or corresponding base to provide a significant buffering capacity to the composition (e.g., a "pH-adjusting agent") (aspect 110).

In aspects, the invention provides pharmaceutically acceptable compositions of aspect 110, wherein the composition comprises one or more ophthalmologically suitable acidifying agents, alkalizing agents, or both, in a concentration such that they do not cause detectable or clinically significant irritation or damage to the eye (aspect 111).

In aspects, the invention provides pharmaceutically acceptable compositions of any one or both of aspect 110 and aspect 111, wherein the composition comprises an ophthalmologically suitable pH adjusting agent which is an acidifying agent (aspect 112).

In aspects, the invention provides pharmaceutically acceptable compositions of any one or more of aspects 110-112, wherein the ophthalmologically suitable pH adjusting agent is characterizable as a strong acid (aspect 113).

In aspects, the invention provides compositions of aspect 113, wherein the ophthalmologically suitable strong acid is hydrochloric acid (HCl) (aspect 114).

In aspects, the invention provides pharmaceutically acceptable compositions of any one or both of aspect 110 and aspect 111, wherein the composition comprises an ophthalmologically suitable pH adjusting agent which is an alkalizing agent (aspect 115).

In aspects, the invention provides pharmaceutically acceptable compositions of any one or more of aspects 110, aspect 111, and aspect 115, wherein the ophthalmologically suitable pH adjusting agent is characterizable as a strong base (aspect 116).

In aspects, the invention provides pharmaceutically acceptable compositions of aspect 116, wherein the strong base is sodium hydroxide (NaOH) (aspect 117).

In aspects, the invention provides compositions of any one or more of aspects 110-117, wherein the ophthalmologically suitable pH adjusting agent(s) is/are used to adjust the pH of the composition to between about 6-about 6.5 (aspect 118).

In aspects, the invention provides compositions of any one or more of aspects 110-118, wherein the ophthalmologically suitable pH adjusting agent(s) is/are used to adjust the pH of the composition to between about 6.2-about 6.4 (aspect 119).

In aspects, the invention provides pharmaceutically acceptable compositions of any one or more of aspects 110-119, wherein the ophthalmologically suitable pH adjusting agent(s) is/are used to adjust the pH of the composition to about 6.3 (aspect 120).

Preservatives

In aspects, the invention provides pharmaceutically acceptable compositions of any one or more of aspects 62-120, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of 2 weeks or more of storage at about room temperature (e.g., at about 25° C.+/−2° C.), about 25° C. and about 60% relative humidity, about 40° C. and about 75% relative humidity, or any combination thereof post-manufacturing (aspect 121).

In aspects, the invention provides pharmaceutically acceptable compositions of any one or more of aspects 62-121, wherein the pharmaceutically acceptable and ophthalmologically suitable composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of 3 weeks or more of storage at about room temperature (e.g., at about 25° C.+/−2° C.), about 25° C. and about 60% relative humidity, about 40° C. and about 75% relative humidity, or any combination thereof post-manufacturing (aspect 122).

In aspects, the invention provides pharmaceutically acceptable compositions of any one or more of aspects 62-122, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 1 month or more of storage at about room temperature (e.g., at about 25° C.+/−2° C.), about 25° C. and about 60% relative humidity, about 40° C. and about 75% relative humidity, or any combination thereof post-manufacturing (aspect 123).

In aspects, the invention provides pharmaceutically acceptable compositions of any one or more of aspects 62-123, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 6 weeks or more of storage at about room temperature (e.g., at about 25° C.+/−2° C.), about 25° C. and about 60% relative humidity, about 40° C. and about 75% relative humidity, or any combination thereof post-manufacturing (aspect 124).

In aspects, the invention provides pharmaceutically acceptable compositions of any one or more of aspects 62-124, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 2 months or more of storage at about room temperature (e.g., at about 25° C.+/−2° C.), about 25° C. and about 60% relative humidity, about 40° C. and about 75% relative humidity, or any combination thereof post-manufacturing (aspect 125).

In aspects, the invention provides pharmaceutically acceptable compositions of any one or more of aspects 62-125, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 10 weeks or more of storage at about room temperature (e.g., at about 25° C.+/−2° C.), about 25° C. and about 60% relative humidity, about 40° C. and about 75% relative humidity, or any combination thereof post-manufacturing (aspect 126).

In aspects, the invention provides pharmaceutically acceptable compositions of any one or more of aspects 62-126, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 3 months or more of storage at about room temperature (e.g., at about 25° C.+/−2° C.), about 25° C. and about 60% relative humidity, about 40° C. and about 75% relative humidity, or any combination thereof post-manufacturing (aspect 127).

In aspects, the invention provides pharmaceutically acceptable compositions of any one or more of aspects 62-127, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 4 months or more of storage at about room temperature (e.g., at about 25° C.+/−2° C.), about 25° C. and about 60% relative humidity, about 40° C. and about 75% relative humidity, or any combination thereof post-manufacturing (aspect 128).

In aspects, the invention provides pharmaceutically acceptable compositions of any one or more of aspects 62-128, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 5 months or more of storage at about room temperature (e.g., at about 25° C.+/−2° C.), about 25° C. and about 60% relative humidity, about 40° C. and about 75% relative humidity, or any combination thereof post-manufacturing (aspect 129).

In aspects, the invention provides pharmaceutically acceptable compositions of any one or more of aspects 62-129, wherein the composition comprises one or more ophthalmologically suitable preservatives in an amount effective in detectably improving the stability of the ketorolac compound(s), the phenylephrine compound(s), or both, detectably or significantly inhibiting microbial growth within the composition, or any or all thereof, at a period of about 6 months or more of storage at about room temperature (e.g., at about 25° C.+/−2° C.), about 25° C. and about 60% relative humidity, about 40° C. and about 75% relative humidity, or any combination thereof post-manufacturing, e.g., $\geq\sim6$, $\geq\sim8$, $\geq\sim10$, $\geq\sim12$, $\geq\sim15$, $\geq\sim18$, $\geq\sim21$, $\geq\sim24$, $\geq\sim27$, or $\geq\sim30$ months, e.g., $\sim6$-$\sim36$ mos. (aspect 130).

In aspects, the invention provides pharmaceutically acceptable compositions of any one or more of aspects 121-130, wherein the ophthalmologically suitable preservative is selected from a group comprising quaternary ammonium salts, hydrogen peroxide, sorbic acid, biguanides, cationic compounds, p-hydroxybenzoates, alcohol compounds, sodium dehydroacetate, and thiomersal (aspect 131).

In aspects, the invention provides pharmaceutically acceptable compositions any one or more of aspects 121-131, wherein the ophthalmologically suitable preservative is selected from a group comprising quaternary ammonium salts (aspect 132).

In aspects, the invention provides pharmaceutically acceptable compositions of any one or more of aspects 121-132, wherein the ophthalmologically suitable preservative is a benzalkonium chloride compound (aspect 133).

In aspects, the invention provides compositions of any one or more of aspects 121-133, wherein the preservative is benzalkonium chloride (aspect 134).

In aspects, the invention provides pharmaceutically acceptable compositions of any one or more of aspects 121-134, wherein the composition comprises benzalkonium chloride in an amount of between about 0.001-about 0.05 wt/v. % (aspect 135).

In aspects, the invention provides pharmaceutically acceptable compositions of any one or more of aspects 121-135, wherein the composition comprises benzalkonium chloride in an amount of between about 0.01-about 0.05 wt/v. % (aspect 136).

In aspects, the invention provides pharmaceutically acceptable compositions of any one or more of aspects 121-136, wherein the composition comprises benzalkonium chloride in an amount of between about 0.01-about 0.04 wt/v. % (aspect 137).

In aspects, the invention provides pharmaceutically acceptable compositions of any one or more of aspects 121-137, wherein the composition comprises benzalkonium chloride in an amount of between about 0.01-about 0.03 wt/v. % (aspect 138).

In aspects, the invention provides pharmaceutically acceptable compositions of any one or more of aspects 121-138, wherein the composition comprises benzalkonium chloride in an amount of about 0.02 wt/v. % (aspect 139).

Carrier Component(s)

In aspects, the invention provides pharmaceutically acceptable compositions of any one or more of aspects 62-139, wherein the composition comprises an ophthalmologically suitable carrier, forming a carrier composition, in an amount effective in delivering the carrier composition comprising effective amounts of APIs or both APIs and excipients (1) to a component(s) to form a combination composition or (2) to the eye, wherein the carrier does not detectably or significantly adversely affect the stability of the composition at a period of about 2 weeks of storage at about room temperature (e.g., at about 25° C.+/−2° C.), about 25° C. and about 60% relative humidity, about 40° C. and about 75% relative humidity, or any combination thereof post-manufacturing (aspect 140).

In aspects, the invention provides pharmaceutically acceptable compositions of any one or more of aspects 62-140, wherein the composition comprises an ophthalmologically suitable carrier, forming a carrier composition, in an amount effective in delivering the composition comprising effective amounts of APIs or both APIs and excipients (1) to a component(s) to form a combination composition or (2) to the eye, wherein the carrier does not detectably or significantly adversely affect the stability of the composition at a period of about 1 month of storage at about room temperature (e.g., at about 25° C.+/−2° C.), about 25° C. and about 60% relative humidity, about 40° C. and about 75% relative humidity, or any combination thereof post-manufacturing (aspect 141).

In aspects, the invention provides pharmaceutically acceptable compositions of any one or more of aspects 62-141, wherein the composition comprises an ophthalmologically suitable carrier, forming a carrier composition, in an amount effective in delivering the composition comprising effective amounts of APIs or both APIs and excipients (1) to a component(s) to form a combination composition or (2) to the eye, wherein the carrier does not detectably or significantly adversely affect the stability of the composition at a period of about 2 months of storage at about room temperature (e.g., at about 25° C.+/−2° C.), about 25° C. and about 60% relative humidity, about 40° C. and about 75% relative humidity, or any combination thereof post-manufacturing (aspect 142).

In aspects, the invention provides pharmaceutically acceptable compositions of any one or more of aspects 62-142, wherein the composition comprises an ophthalmologically suitable carrier, forming a carrier composition, in an amount effective in delivering the composition comprising effective amounts of APIs or both APIs and excipients (1) to a component(s) to form a combination composition or (2) to the eye, wherein the carrier does not detectably or significantly adversely affect the stability of the composition at a period of about 3 months of storage at about room temperature (e.g., at about 25° C.+/−2° C.), about 25° C. and about 60% relative humidity, about 40° C. and about 75% relative humidity, or any combination thereof post-manufacturing (aspect 143).

In aspects, the invention provides pharmaceutically acceptable compositions of any one or more of aspects 62-143, wherein the composition comprises an ophthalmologically suitable carrier, forming a carrier composition, in an amount effective in delivering the composition comprising effective amounts of APIs or both APIs and excipients (1) to a component(s) to form a combination composition or (2) to the eye, wherein the carrier does not detectably or significantly adversely affect the stability of the composition at a period of about 4 months of storage at about room temperature (e.g., at about 25° C.+/−2° C.), about 25° C. and about 60% relative humidity, about 40° C. and about 75% relative humidity, or any combination thereof post-manufacturing (aspect 144).

In aspects, the invention provides pharmaceutically acceptable compositions of any one or more of aspects 62-144, wherein the composition comprises an ophthalmologically suitable carrier, forming a carrier composition, in an amount effective in delivering the composition comprising effective amounts of APIs or both APIs and excipients (1) to a component(s) to form a combination composition or (2) to the eye, wherein the carrier does not detectably or significantly adversely affect the stability of the composition at a period of about 5 months of storage at about room temperature (e.g., at about 25° C.+/−2° C.), about 25° C. and about 60% relative humidity, about 40° C. and about 75% relative humidity, or any combination thereof post-manufacturing (aspect 145).

In aspects, the invention provides pharmaceutically acceptable compositions of any one or more of aspects 62-145, wherein the composition comprises an ophthalmologically suitable carrier, forming a carrier composition, in an amount effective in delivering the composition comprising effective amounts of APIs or both APIs and excipients (1) to a component(s) to form a combination composition or (2) to the eye, wherein the carrier does not detectably or significantly adversely affect the stability of the composition at a period of about 6 months of storage at about room temperature (e.g., at about 25° C.+/−2° C.), about 25° C. and about 60% relative humidity, about 40° C. and about 75% relative humidity, or any combination thereof post-manufacturing, e.g., $\geq$~6, $\geq$~8, $\geq$~10, $\geq$~12, $\geq$~15, $\geq$~18, $\geq$~21, $\geq$~24, $\geq$~27, or $\geq$~30 months, e.g., ~6-~36 mos. (aspect 146).

In aspects, the invention provides pharmaceutically acceptable compositions of any one or more of aspects 62-146, wherein the composition comprises an ophthalmologically suitable carrier characterizable as an aqueous carrier, such that the composition is characterizable as an aqueous carrier composition (aspect 147).

In aspects, the invention provides the carrier composition of aspect 147, wherein the aqueous carrier is selected from a group comprising water for injection (WFI) and deionized water (aspect 148).

In aspects, the invention provides the carrier composition of aspect 148, wherein the aqueous carrier is water for injection (WFI) (aspect 149).

In aspects, the invention provides the carrier composition of any one or both of aspect 148 and aspect 149, wherein the water is not detectably, significantly, or intentionally deuterated (aspect 150).

In aspects, the invention provides pharmaceutically acceptable compositions of any one or more of aspects 62-150, wherein the composition comprises an ophthalmologically suitable carrier, forming a carrier composition, in an amount representing between about 50 wt/v. % and about 99 wt/v. % of the composition (aspect 151).

In aspects, the invention provides pharmaceutically acceptable compositions of any one or more of aspects 62-151, wherein the composition comprises an ophthalmologically suitable carrier, forming a carrier composition, in an amount representing between about 50 wt/v. % and about 90 wt/v. % of the composition (aspect 152).

In aspects, the invention provides pharmaceutically acceptable compositions of any one or more of paragraphs aspects 62-152, wherein the composition comprises an ophthalmologically suitable carrier, forming a carrier composition, in an amount representing between about 50 wt/v. % and about 85 wt/v. % of the composition (aspect 153).

In aspects, the invention provides pharmaceutically acceptable compositions of any one or more of aspects 62-153, wherein the composition comprises an ophthalmologically suitable carrier, forming a carrier composition, in an amount representing between about 50 wt/v. % and about 80 wt/v. % of the composition (aspect 154).

In aspects, the invention provides pharmaceutically acceptable compositions of any one or more of aspects 62-154, wherein the composition comprises an ophthalmologically suitable carrier, forming a carrier composition, in an amount representing between about 50 wt/v. % and about 75 wt/v. % of the composition (aspect 155).

In aspects, the invention provides pharmaceutically acceptable compositions of any one or more of aspects 62-155, wherein the composition comprises an ophthalmologically suitable carrier, forming a carrier composition, in an amount representing between about 50 wt/v. % and about 70 wt/v. % of the composition (aspect 156).

Additional API(s)

In aspects, the invention provides pharmaceutically acceptable compositions of any one or more of aspects 1-156, wherein the composition does not comprise any API other than one or more ketorolac compounds and one or more phenylephrine compounds (aspect 157).

In aspects, the invention provides pharmaceutically acceptable compositions of any one or more of aspects 1-156, wherein the composition comprises one or more additional ophthalmologically suitable APIs in an amount effective in detectably or significantly increasing the efficacy of the ketorolac compound(s), detectably or significantly increasing the efficacy of the phenylephrine compound(s), or increasing the therapeutic usefulness of the composition (e.g., demonstrating a detectable or significant beneficial effect in the recipient of the composition) without significantly impairing the efficacy of the ketorolac compound(s) or the phenylephrine compound(s) (aspect 158).

In aspects, the invention provides pharmaceutically acceptable compositions of aspect 158, wherein the composition comprises one or more additional ophthalmologically suitable APIs in an amount effective in detectably or significantly increasing the efficacy of the ketorolac compound(s), detectably or significantly increasing the efficacy of the phenylephrine compound(s), or increasing the therapeutic usefulness of the composition (e.g., demonstrating a detectable or significant beneficial effect in the recipient of the composition) without significantly impairing the efficacy of the ketorolac compound(s) or the phenylephrine compound(s) selected from a group comprising steroidal anti-inflammatory agent(s), non-steroidal anti-inflammatory (NSAID) agent(s), antibacterial agent(s), antifungal agent(s), antiviral agent(s), anti-mycotic agents, antineoplastic agent(s), anti-allergic agent(s), intraocular pressure reducing agent(s), and glaucoma-treating agents (aspect 159).

In aspects, the invention provides pharmaceutically acceptable compositions of any one or both of aspects 158 and aspect 159, wherein the composition comprises an ophthalmologically suitable antibiotic agent in an amount effective in detectably or significantly treating, preventing, or inhibiting further progression of a bacterial growth (e.g., a bacterial infection) of the eye (aspect 160).

In aspects, the invention provides compositions of aspect 160, wherein the composition comprises an ophthalmologically suitable antibiotic agent selected from a group comprising ciprofloxacin, gentamicin, tobramycin, and ofloxacin (aspect 161).

In aspects, the invention provides pharmaceutically acceptable compositions of any one or more of aspects 158-161, wherein the composition comprises at least one additional ophthalmologically suitable NSAID in addition to the ketorolac compound(s) (aspect 162).

II. METHOD OF MAKING/MANUFACTURING

In aspects, the invention provides a method of manufacturing a pharmaceutically acceptable carrier composition according to any one or more of aspects 1-162, wherein the method comprises (1) dissolving a ketorolac compound in a carrier material to form a solution of ketorolac; (2) dissolving a phenylephrine compound in the resulting solution of (1); (3) diluting the solution resulting from (2); adding one or more pH-adjusting agents to bring the pH of the solution resulting from (3) to a pH of between about 6.0-about 6.6, e.g., to a pH of about 6.3; (4) bringing the final volume of the solution up to a final volume (aspect 163).

In aspects, the invention provides the method of aspect 163, wherein the method further comprises sterilizing the carrier composition resulting from the method wherein the process of sterilization detectably or significantly reduces the amount of related compounds and impurities associated with the composition upon storage of the composition at 25° C.+/−2° C. and about 60% relative humidity, at about 40° C. and about 75% relative humidity, or under either or both conditions for at least about 2 weeks after manufacturing (aspect 164).

In aspects, the invention provides the method of any one or both of aspect 163 and aspect 164, wherein the method detectably or significantly reduces the amount of related compounds and impurities associated with the carrier composition upon storage of the composition at 25° C.+/−2° C. and about 60% relative humidity, at about 40° C. and about 75% relative humidity, or under either or both conditions for at least about 3 weeks after manufacturing (aspect 165).

In aspects, the invention provides the method of any one or more of paragraphs 163-165, wherein the method detectably or significantly reduces the amount of related compounds and impurities associated with the carrier composition upon storage of the composition at 25° C.+/−2° C. and about 60% relative humidity, at about 40° C. and about 75% relative humidity, or under either or both conditions for at least about 1 month after manufacturing (aspect 166).

In aspects, the invention provides the method of any one or more of aspects 163-166, wherein the method detectably or significantly reduces the amount of related compounds and impurities associated with the carrier composition upon storage of the composition at 25° C. +/−2° C. and about 60% relative humidity, at about 40° C. and about 75% relative humidity, or under either or both conditions for at least about 2 months after manufacturing (aspect 167).

In aspects, the invention provides the method of any one or more of aspects 163-167, wherein the method detectably or significantly reduces the amount of related compounds and impurities associated with the carrier composition upon storage of the composition at 25° C. +/−2° C. and about 60% relative humidity, at about 40° C. and about 75% relative humidity, or under either or both conditions for at least about 3 months after manufacturing (aspect 168).

In aspects, the invention provides the method of any one or more of aspects 163-167, wherein the method detectably or significantly reduces the amount of related compounds and impurities associated with the carrier composition upon storage of the composition at 25° C. +/−2° C. and about 60% relative humidity, at about 40° C. and about 75% relative humidity, or under either or both conditions for at least about 4 months after manufacturing (aspect 169).

In aspects, the invention provides the method of any one or more of aspects 163-169, wherein the method detectably or significantly reduces the amount of related compounds and impurities associated with the carrier composition upon storage of the composition at 25° C. +/−2° C. and about 60% relative humidity, at about 40° C. and about 75% relative humidity, or under either or both conditions for at least about 5 months after manufacturing (aspect 170).

In aspects, the invention provides the method of any one or more of aspects 163-170, wherein the method detectably or significantly reduces the amount of related compounds and impurities associated with the carrier composition upon storage of the composition at 25° C. +/−2° C. and about 60% relative humidity, at about 40° C. and about 75% relative humidity, or under either or both conditions for at least about 6 months after manufacturing, e.g., ≥~6, ≥~8, ≥~10, ≥~12, ≥~15, ≥~18, ≥~21, ≥~24, ≥~27, or ≥~30 months, e.g., ~6-~36 mos. (aspect 171).

In aspects, the invention provides the method of any one or more of aspects 163-171, wherein the carrier material is nitrogen purged prior to the addition of the ketorolac compound(s) (aspect 172).

In aspects, the invention provides the method of any one or more of aspects 163-172, wherein the one or more excipients are added to the carrier material and fully dissolved prior to the addition of the ketorolac compound(s) (aspect 173).

In aspects, the invention provides the method of any one or more of aspects 163-173, wherein the pH adjusting agent(s) are selected from a group comprising a strong acid and a strong base (aspect 174).

In aspects, the invention provides methods of any one or more of aspects 163-174, wherein the pH adjusting agent(s) are selected from HCl and NaOH (aspect 175).

In aspects, the invention provides the method of any one or more of aspects 163-175, wherein the sterilization process comprises sterile filtration (aspect 176).

In aspects, the invention provides the method of any one or more of aspects 163-176, wherein the resulting carrier composition has a pH of about 6.3 (aspect 177).

III. KITS

In aspects, the invention provides a kit comprising a pharmaceutically acceptable composition of any one or more of aspects 1-162 packaged in one or more single use containers, wherein the kit further comprises one or more delivery devices for (a) administering the composition to a recipient; (b) delivering the composition to an existing solution/composition (e.g., irrigation solution), device (e.g., component of an irrigation solution delivery system such as an irrigation solution bag), or system (e.g., a controlled-release, ophthalmic irrigation solution delivery system) for delivery to a recipient, or (c) both (a) and (b) (aspect 178).

In aspects, the invention provides a kit comprising a carrier composition of any one or more of aspects 140-162 packaged in one or more single use containers, wherein the kit further comprises one or more delivery devices for (a) administering the composition to a recipient; (b) delivering the composition to an existing solution/composition (e.g., irrigation solution), device (e.g., component of an irrigation solution delivery system such as an irrigation solution bag), or system (e.g., a controlled release, ophthalmic irrigation solution delivery system) for delivery to a recipient, or (c) both (a) and (b) (aspect 179).

In aspects, the invention provides the kit of any one or both of aspect 178 and 179, wherein the composition is made according to any one or more of the methods of aspects 163-177 (aspect 180).

In aspects, the invention provides the kit of any one or more of aspects 178-180, wherein the delivery device is a syringe system (aspect 181).

In aspects, the invention provides the kit of any one or more of aspects 178-181, wherein the delivery device is a syringe system wherein any single use container comprising a pharmaceutically acceptable composition present in the kit is accessible to a delivery device/system of the kit, such as, e.g., containing a stopper which effectively seals the single use container but which is penetrable by the delivery device/system such that the delivery device can extract the composition from the single use container (aspect 182).

In aspects, the invention provides the kit of any one or more of aspects 178-182, wherein each single use container comprises between about 1 mL and about 10 mL of a carrier composition (aspect 183).

In aspects, the invention provides the kit of any one or more of aspects 178-183, wherein each single use container comprises between about 1 mL and about 8 mL of a carrier composition (aspect 184).

In aspects, the invention provides the kit of any one or more of aspects 178-184, wherein each single use container comprises between about 1 mL and about 6 mL of a carrier composition (aspect 185).

In aspects, the invention provides the kit of any one or more of aspects 178-185, wherein each single use container comprises between about 2 mL and about 6 mL of a carrier composition (aspect 186).

In aspects, the invention provides the kit of any one or more of aspects 178-186, wherein each single use container comprises about 4 mL of a carrier composition (aspect 187).

In aspects, the invention provides the kit of any one or more of aspects 178-187, wherein the kit further comprises a separately packaged diluent for further diluting the composition prior to use (aspect 188).

In aspects, the invention provides the kit of any one or more of aspects 178-188, wherein the delivery device/system is capable of providing carrier composition(s) contained therein to the eye in a controlled manner (aspect 189).

In aspects, the invention provides the kit of any one or more of aspects 178-189, wherein the delivery device/system is capable of providing carrier composition(s) to the eye in a drop-by-drop manner (aspect 190).

In aspects, the invention provides the kit of any one or more of aspects 178-190, wherein the delivery device/system is capable of providing carrier composition(s) to the eye in a controlled stream of carrier composition, such as, e.g., the pressure and volume of carrier composition(s) in the stream of carrier composition is controllable by the user administering the composition(s) (aspect 191).

In aspects, the invention provides the kit of any one or more of aspects 178-191, wherein the delivery device/system is capable of providing carrier composition(s) to the eye in a form which is suitable for use as an ophthalmic irrigation solution (aspect 192).

In aspects, the invention provides the kit of any one or more of aspects 178-188, wherein the delivery device/system is capable of providing carrier composition(s) contained therein to a controlled-release ophthalmic irrigation solution delivery system (e.g., to a bag comprising an irrigation solution for use in the system) in a manner which does not detectably or significantly modify the sterile integrity of the composition(s) (aspect 193).

In aspects, the invention provides the kit of aspect 193 or aspect 193, wherein pharmaceutically acceptable compositions is delivered to the eye in at least a substantially consistent, controlled manner, e.g., the volume of composition or amount of each of any API(s) of the composition, administered per period of time, the rate of composition administered per period of time, or both vary from one period of time to another during a period of administration of no more than about 20% (aspect 194).

In aspects, the invention provides the kit of aspect 194, wherein pharmaceutically acceptable composition(s) is/are delivered to the eye in at least a substantially consistent, controlled manner, e.g., the volume of composition or amount of each of any API(s) of the composition, administered per period of time, the rate of composition administered per period of time, or both vary from one period of time to another during a period of administration of no more than about 10% (aspect 195).

In aspects, the invention provides the kit of aspect 195, wherein pharmaceutically acceptable composition(s) is delivered to the eye in at least a substantially consistent, controlled manner, e.g., the volume of composition or amount of each of any API(s) of the composition, administered per period of time, the rate of composition administered per period of time, or both vary from one period of time to another during a period of administration of no more than about 5% (aspect 196).

IV. METHODS OF USE (GENERALLY)

In aspects, the invention provides a method of (1) preventing significant inflammation during or after an ophthalmologically-related procedure, (2) maintaining suitable pupil size (e.g., preventing significant intraoperative miosis) during an ophthalmologically-related procedure, (3) detectably or significantly reducing postoperative ocular pain following an ophthalmologically-related procedure, or (4) any combination thereof, comprising application of a pharmaceutically acceptable and ophthalmologically suitable composition during such an ophthalmologically-related procedure, for a period of time after such an ophthalmologically-related procedure, or both, comprising pharmaceutically acceptable amounts of each of one or more ketorolac compounds and one or more phenylephrine compounds, wherein the composition (a) lacks a buffer component wherein (i) the buffer is a combination of a weak base and its conjugate acid, a weak acid and its conjugate base, or both; (ii) wherein the acid and base pairs of such a buffer component are present in concentrations of within 10× of one another; (iii) wherein the pKa of any such buffer component is between 4.3-8.3, such as the pKa of any such buffer component is between 5.3-7.3, e.g., between about 6.0 and 6.6; and (iv) wherein, when the ophthalmologically suitable composition is at a pH of 6.3, the acid and base pairs of the buffer component can prevent a change in pH of the composition of more than 2% when 0.1 moles of HCl or 0.1 moles of NaOH are added to 1 L of the composition; (b) maintains a pH of between 5.5-7; and (c) retains at least 97% of the one or more ketorolac compounds and at least 97% of the one or more phenylephrine compounds when stored at 25° C.+/−2° C., at about 25° C. and about 60% relative humidity, at about 40° C. and about 75% relative humidity, or under any or all such conditions for at least one month, e.g., ≥~2 months, ≥~3 months, ≥~6 months, ≥~9 months, ≥~12 months, ≥~18 months, or ≥~24 months, after manufacturing (aspect 197).

In aspects, the invention provides the method of aspect 197, wherein the pharmaceutically acceptable and ophthalmologically suitable composition further comprises any one or more of the characteristics described in aspects 1-162 (aspect 198).

In aspects, the invention provides the method of any one or both of aspect 197 and aspect 198, wherein any one or more of the compositions are made according to a method of any one or more of aspects 163-177 (aspect 199).

In aspects, the invention provides the method of any one or more of aspects 197-199, wherein the method comprises providing the any one or more pharmaceutically acceptable and ophthalmologically suitable compositions for use in the method as a kit of any one or more of aspects 178-196 (aspect 200).

In aspects, the invention provides the method of any one or more of aspects 197-200, wherein the pharmaceutically acceptable and ophthalmologically suitable composition is a carrier composition (aspect 201).

In aspects, the invention provides the method of any one or more of aspects 197-201, wherein the pharmaceutically acceptable and ophthalmologically suitable composition is diluted prior to use (aspect 202).

In aspects, the invention provides the pharmaceutically acceptable and ophthalmologically suitable composition of any one or more of aspects 197-202, wherein the composition is added to a separate ophthalmic irrigation solution to form a combination composition prior to use (aspect 203).

In aspects, the invention provides the method of any one or more of aspects 197-203, wherein the pharmaceutically acceptable and ophthalmologically suitable composition is delivered to the eye in a controlled manner (aspect 204).

In aspects, the invention provides the method of any one or more of aspects 197-204, wherein the pharmaceutically acceptable and ophthalmologically suitable composition is delivered in a drop-by-drop manner (aspect 205).

In aspects, the invention provides the method of any one or more of aspects 197-205, wherein the pharmaceutically acceptable and ophthalmologically suitable composition is delivered to the eye in a controlled stream of composition, such as, e.g., the pressure and volume of composition in the stream of composition is controllable by the user administering the composition(s) (aspect 206).

In aspects, the invention provides methods of any one or more of aspects 197-206, wherein the pharmaceutically/ophthalmologically suitable composition is delivered to the eye as a component of a combination composition, e.g., as an ophthalmic irrigation solution, and is administered using standard ophthalmic irrigation procedures of the art (aspect 207).

V. METHODS OF TREATMENT

In aspects, the invention provides a method of treating or preventing a disease or condition benefiting from a combination therapy of an anti-inflammatory and mydriatic compound, the method comprising administering an effective amount of a pharmaceutically acceptable and ophthalmologically suitable composition, either alone or as a component of a combination composition, comprising pharmaceutically acceptable amounts of each of one or more ketorolac compounds and one or more phenylephrine compounds, wherein the composition (1) lacks a buffer component wherein (a) the buffer is a combination of a weak base and its conjugate acid, a weak acid and its conjugate base, or both; (b) wherein the acid and base pairs of such a buffer component are present in concentrations of within 10× of one another; (c) wherein the pKa of any such buffer component is between 4.3-8.3, such as the pKa of any such buffer component is between 5.3-7.3, e.g., between about 6.0 and 6.6; and (d) wherein, when the ophthalmologically suitable composition is at a pH of 6.3, the acid and base pairs of the buffer component can prevent a change in pH of the composition of more than 2% when 0.1 moles of HCl or 0.1 moles of NaOH are added to 1 L of the composition; (2) maintains a pH of between 5.5-7; and (3) retains at least 97% of the one or more ketorolac compounds and at least 97% of the one or more phenylephrine compounds when stored at 25° C.+/−2° C., at about 25° C. and about 60% relative humidity, at about 40° C. and about 75% RH, or under any or all such conditions for at least one month, e.g., ≥~2 months, ≥~3 months, ≥~6 months, ≥~9 months, ≥~12 months, ≥~18 months, or ≥~24 months for at least 1 month after manufacturing (aspect 208).

In aspects, the invention provides the method of aspect 208, wherein the pharmaceutically acceptable and ophthalmologically suitable composition further comprises one or more characteristics described in any one or more of aspects 1-162 (aspect 209).

In aspects, the invention provides the method of any one or both of aspect 208 and aspect 209, wherein the pharmaceutically acceptable and ophthalmologically suitable composition is a carrier composition (aspect 210).

In aspects, the invention provides the method of any one or more of aspects 208-210, wherein the condition is a condition arising from or during an ophthalmologically-related procedure (aspect 211).

In aspects, the invention provides the method of aspect 211, wherein the ophthalmologically-related procedure is selected from a group comprising cataract surgery and intraocular lens replacement (aspect 212).

In aspects, the invention provides the method of any one or more of aspects 208-212, wherein any one or more of the pharmaceutically acceptable and ophthalmologically suitable compositions are made according to a method of any one or more of aspects 163-177 (aspect 213).

In aspects, the invention provides the method of any one or more of aspects 208-213, wherein the method comprises providing the any one or more pharmaceutically acceptable and ophthalmologically suitable compositions for use in the method as a kit of any one or more of aspects 178-196 (aspect 214).

In aspects, the invention provides the method of any one or more of paragraphs aspects 208-214, wherein the pharmaceutically acceptable and ophthalmologically suitable composition is delivered to the eye in a controlled manner (aspect 215).

In aspects, the invention provides the method of any one or more of aspects 208-215, wherein the pharmaceutically acceptable and ophthalmologically suitable composition is delivered in a drop-by-drop manner (aspect 216).

In aspects, the invention provides the method of any one or more of paragraphs aspects 208-216, wherein the pharmaceutically acceptable and ophthalmologically suitable composition is delivered to the eye in a controlled stream of composition, such as, e.g., the pressure and volume of composition in the stream of composition is controllable by the user administering the composition(s) (aspect 217).

In aspects, the invention provides the method of any one or more of aspects 208-217, wherein the pharmaceutically acceptable and ophthalmologically suitable composition is delivered to the eye as an ophthalmic irrigation solution and is administered using standard ophthalmic irrigation procedures of the art (aspect 218).

In aspects, the invention provides methods of any one or more of aspects 208-218, wherein the composition is diluted prior to use (aspect 219).

In aspects, the invention provides the method of any one or more of aspects 208-219, wherein the pharmaceutically acceptable and ophthalmologically suitable composition is added to a separately provided ophthalmic irrigation solution prior to use to form a combination composition (aspect 220).

In aspects, the invention provides the method of any one or more of aspects 208-220, wherein the pharmaceutically acceptable and ophthalmologically suitable composition is administered as a treatment during an ophthalmologically-related procedure (aspect 221).

In aspects, the invention provides the method of any one or more of aspects 208-221, wherein the pharmaceutically acceptable and ophthalmologically suitable composition is administered over an administration period ranging from a one-time administration to an administration of twice, or three times per day for a period of 1-2 days (aspect 222).

In aspects, the invention provides the method of any one or more of aspects 208-222, wherein the pharmaceutically acceptable and ophthalmologically suitable composition is used over a single administration period of 4 hours or less (aspect 223).

In aspects, the invention provides the method of any one or more of aspects 208-223, wherein treatment with the pharmaceutically acceptable and ophthalmologically suitable composition provides detectably or significantly fewer side effects selected from a group comprising eye irritation, posterior capsule opacification, increased intraocular pressure, and anterior chamber inflammation than treatment with the product approved by the United States Food and Drug Administration (FDA) under NDA number 205388 and the trademark OMIDRIA® and sold under such registered trademark in the United States prior to the submission of this disclosure or a similar reference product approved by FDA under NDA number 205388 or a substantially similar product (again, for clarity, a "reference product" or a "similar reference product" herein is an FDA approved product under NDA number 205388 or substantially similar product), with a substantially similar product being a product that contains most, generally all, or all of the same ingredients in most, generally all, or all cases in the same amounts or which otherwise is approved under an amendment to the NDA without the requirement of any significant new clinical trial for FDA approval for the same or similar indication and for at least substantially the same administration period (aspect 224).

VI. EFFICACY

In aspects, the invention provides the method of any one or more of aspects 197-224, wherein the application of the method results in 1) the prevention of inflammation during or after an ophthalmologically-related procedure, (2) the maintenance of suitable pupil size (e.g., prevention of significant intraoperative miosis) during an ophthalmologically-related procedure, (3) a reduction in postoperative ocular pain following an ophthalmologically-related procedure, or (4) any combination thereof which is at least statistically similar to or better than (e.g., improved over) that resulting from the administration of the product approved by the United States Food and Drug Administration (FDA) under NDA number 205388 and the trademark OMIDRIA® and sold under such registered trademark in the United States prior to the submission of this disclosure or a reference product approved by FDA under NDA number 205388 or a substantially similar product, such as a product that contains most, generally all, or all of the same ingredients in most, generally all, or all cases in the same amounts or which otherwise is approved under an amendment to the NDA without the requirement of any significant new clinical trial for FDA approval, for at least substantially the same period of time and for a similar or the same indication, as determined by a controlled clinical trial recognized by a prevailing regulatory authority, such as the United States Food and Drug Administration (US FDA) (aspect 225).

Example

The following pharmaceutically acceptable phenylephrine-ketorolac combination formulations were generated and evaluated for stability. The purpose of stability testing was to demonstrate that exemplary formulations having the characteristics of formulations described herein (e.g., lacking a buffer) can maintain suitable shelf-life, making the formulations described herein practical for commercial/clinical ophthalmological use.

Formulations A and B described here differ in their inclusion/exclusion of a chelating agent (EDTA); however, both formulations lack a buffer component, a buffer component being defined herein (e.g., lack a buffer component wherein (i) the buffer is a combination of a weak base and its conjugate acid, a weak acid and its conjugate base, or both; (ii) wherein the acid and base pairs of such a buffer component are present in concentrations of within 10× of one another; (iii) wherein the pKa of any such buffer component is between 4.3-8.3, such as the pKa of any such buffer component is between 5.3-7.3, e.g., between about 6.0 and 6.6; or (in aspects, as in this Example, and) (iv) wherein, when the ophthalmologically suitable formulation is at a pH of 6.3, the acid and base pairs of the buffer component can prevent a change in pH of the formulation of more than 2% when 0.1 moles of HCl or 0.1 moles of NaOH are added to 1 L of the formulation).

Preparation of Formulation A

Formulation A according to Table 1 (below) presents one exemplary formulation of the invention.

TABLE 1

| Formulation A: Phenylephrine + Ketorolac, including EDTA | | |
|---|---|---|
| Sr. No. | Ingredient | Qty/mL |
| 1 | Phenylephrine HCl | 12.4 mg |
| 2 | Ketorolac Tromethamine | 4.24 mg |
| 3 | EDTA | 1.1 mg |
| 3 | 1N HCl/NaOH | Adjust pH to 6.3 |
| 4 | Water for Injection (WFI) | QS to 1.0 mL |

The following manufacturing process was performed to generate Formulation A.

A first, clean, 2 L container was filled with 1500 mL of hot (about 120° F.) water for injection (WFI). The hot WFI was then subjected to a nitrogen purging process to remove excess dissolved oxygen.

The nitrogen purging process was performed until the WFI reached oxygen levels of below 2 parts per million (ppm).

Once such oxygen levels were met, 1 L of the then cooled, low dissolved oxygen WFI was transferred to a second, clean container and re-sealed under a nitrogen blanket.

The remaining 500 mL of cooled, nitrogen purged WFI was transferred into a third, clean 1 L container; nitrogen purging was continued in this container.

While purging, ethylenediamine tetra acetic acid (EDTA) was added under continuous stirring and stirred until completely dissolved.

Once the EDTA was completely dissolved, ketorolac tromethamine was added and stirred continuously to ensure dissolution.

Once the ketorolac tromethamine was completely dissolved, phenylephrine HCl was added to the solution and stirring was continued until the phenylephrine HCL was completely dissolved.

Once the phenylephrine HCl was completely dissolved, 400 mL of the previously cooled and nitrogen purged WFI was added to the solution.

The solution was then stirred for an additional 10 minutes to ensure complete mixing.

The pH of the solution was then adjusted to pH 6.3 using pH adjusting agent(s) (1 N HCl or NaOH).

Finally, the volume of the final solution was brought to 1 L using remaining WFI and the final solution was sterile filtered into single use 5 mL vials such that each 5 mL single use vial contained 4 mL of sterile filtered solution.

Preparation of Formulation B

Formulation B according to Table 2 (below) presents a second exemplary formulation of the invention.

TABLE 2

| Formulation B: PE + KE, Excluding Chelating Agent | | |
|---|---|---|
| Sr. No. | Ingredient | Qty/mL |
| 1 | Phenylephrine HCl | 12.4 mg |
| 2 | Ketorolac Tromethamine | 4.24 mg |
| 3 | 1N HCl/NaOH | Adjust pH to 6.3 |
| 4 | Water for Injection (WFI) | QS to 1.0 mL |

The following manufacturing process was performed to generate Formulation B.

A first, clean 2 L container was filled with 1500 mL of hot (about 120° F.) water for injection (WFI). The hot WFI was then subjected to a nitrogen purging process to remove excess dissolved oxygen.

The nitrogen purging process was performed until the WFI reached oxygen levels of below 2 ppm.

Once such oxygen levels were met, 1 L of the then cooled, low dissolved oxygen WFI was transferred to a second, clean container and re-sealed under a nitrogen blanket.

The remaining 500 mL of cooled, nitrogen purged WFI was then transferred into a third, clean 1 L container; nitrogen purging was continued in this container.

While purging, the solution was continuously stirred while ketorolac tromethamine was added and completely dissolved.

Upon complete dissolution of the ketorolac tromethamine, phenylephrine HCL was added under continuous stirring until completely dissolved.

Once the phenylephrine HCL was completely dissolved, 400 mL of the previously cooled nitrogen purged WFI was added from the container having been under continuous nitrogen purge prior to addition.

The solution was then stirred for an additional 10 minutes to ensure complete mixing.

The pH of the solution was then adjusted to pH 6.3 using pH adjusting agent(s) (1 N HCl or NaOH).

Finally, the volume of the final solution was brought to 1 L using remaining WFI and the final solution was sterile filtered into single use 5 mL vials such that each 5 mL single use vial contained 4 mL of sterile filtered solution.

Formulations prepared according to the process above were tested for stability under typical (25° C./60% relative humidity) and at least in part under accelerated conditions (40° C./75% relative humidity) to determine stability of formulations.

Stability Test Procedure

Formulations A and B (according to Tables 1 and 2 above) were subjected to the following stability test. Multiple single use vials of each of formulation A and B were collected and stored under two separate conditions: standard, room temperature (25° C., 60% relative humidity (RH)) and accelerated (40° C., 75% RH) testing conditions. The stability test was designed to measure both (a) remaining API at each time point (Table 3), and (b) specific API-related impurities at each time point (Table 4).

The two formulations were each then tested at specific time points under standard (25° C., 60% relative humidity (RH)) and accelerated (40° C., 75% RH) conditions, and the percentage of API remaining as well as impurity results recorded at each time period. Results are shown in Tables 3 and 4 below.

TABLE 4

Impurities of Formulation A & B

| | | Formulation-A Lot P0051-4-1 Description: APIs + EDTA | | Formulation-B Lot P0051-4-2 Description: Only APIs | |
|---|---|---|---|---|---|
| Cond. | Time | Phenyl-ephrine C** | Ketorolac C‡ | Phenyl-ephrine C | Ketorolac C |
| 40° C., 75% RH | Initial | N/A | N/A | N/A | N/A |
| | 2 Weeks | N/A | N/A | N/A | N/A |
| | 1 Month | N/A | N/A | N/A | N/A |
| | 2 Month | N/A | N/A | N/A | N/A |
| | 3 months | BQL* | 0.054 | BQL | 0.103 |
| | 6 months | BQL | 0.248 | BLQ | 0.263 |
| | 8 months | BQL | 0.27 | BLQ | 0.306 |
| 25° C., 60% RH | Initial | N/A | N/A | N/A | N/A |
| | 1 Month | N/A | N/A | N/A | N/A |
| | 2 Month | N/A | N/A | N/A | N/A |
| | 3 Month | BQL | BQL | BQL | BQL |

*BQL = Below quantification limits;
**Phenylephrine C = Phenylephrine impurity C (1-(3-hydroxyphenyl)-2-(methylamino)ethan-1-one hydrochloride);
‡Ketorolac C = Ketorolac impurity C ((5-benzoyl-2,3-dihydro-lH-pyrrolizine-lH-one)).

Based on 8 months of collected and analyzed data, it is demonstrated that, surprisingly and unexpectedly, even though the Formulations A and B do not contain a buffer component meeting the above defined definition of a buffer, the formulations remain stable over the course of 8 months under accelerated conditions at 40° C. and 75% RH. Formulations were demonstrated to remain stable over the course of at least 3 months when stored under typical conditions of 25° C. and 60% relative humidity (extended periods of time under this condition were not tested as samples remained stable under the accelerated conditions at such time points). The data demonstrate that formulations lacking a buffer and either with or without a chelating agent can maintain extended stability, e.g., up to 8 months under such conditions, without detection of significant levels of impurities. This data further demonstrates, despite both formulations not containing any buffers/buffer component, no substantial change in pH occurs when stored for such periods under such conditions (formulations maintain a stable pH).

TABLE 3

Stability of Formulation A & B

| | | Formulation-A Lot P0051-4-1 Description: APIs + EDTA | | | Formulation-B Lot P0051-4-2 Description: Only APIs | | |
|---|---|---|---|---|---|---|---|
| Cond. | Time | Remaining Phenylephrine (%) | Remaining Ketorolac (%) | pH | Remaining Phenylephrine (%) | Remaining Ketorolac (%) | pH |
| 40° C., 75% RH | Initial | 99 | 99.1 | 6.44 | 101.1 | 99.2 | 6.59 |
| | 2 Weeks | 98.5 | 98.3 | 6.38 | 99.9 | 99.6 | 6.51 |
| | 1 Month | 99.2 | 99.8 | 6.42 | 99.6 | 99.7 | 6.62 |
| | 2 Month | 98.2 | 98.2 | 6.46 | 98.9 | 98.3 | 6.63 |
| | 3 months | 101.3 | 101.1 | 6.40 | 101.0 | 100.6 | 6.55 |
| | 6 months | 99.8 | 99.1 | 6.53 | 98.7 | 97.6 | 6.67 |
| | 8 months | 101.7 | 101.5 | 6.50 | 101.4 | 101 | 6.68 |
| 25° C., 60% RH* | Initial | 99 | 99.1 | 6.44 | 101.1 | 99.2 | 6.59 |
| | 1 Month | 99.5 | 100 | 6.47 | 99.2 | 99.3 | 6.62 |
| | 2 Month | 99.5 | 99.2 | 6.47 | 98.6 | 98.2 | 6.59 |
| | 3 Month | 101.3 | 100.7 | 6.37 | 101.0 | 100.5 | 6.46 |

*Note:
6 month and 8 month time periods for samples stored at 25° C. and 60% RH were not tested due to the demonstrated stability under accelerated conditions.

What is claimed is:

1. A method of promoting dilation of a pupil comprising administering a therapeutically effective amount of an ophthalmologically suitable composition comprising therapeutically effective amounts of each of ketorolac tromethamine and phenylephrine hydrochloride, wherein the composition (1) lacks any combination of a weak base and its conjugate acid that effectively acts as a buffer in the composition at a pH of about 6.3, (2) maintains a pH of between about 6-7 when stored under storage conditions for a period of at least about one month, and (3) retains at least 97% of the one or more ketorolac compounds and at least 97% of the one or more phenylephrine compounds when the composition is stored under storage conditions for at least one month, wherein the storage conditions comprise storage at about 25° C.+/−2° C., at about 25° C. and about 60% relative humidity, storage at about 40° C. and about 75% relative humidity, or storage under any combination of such conditions.

2. The method of claim 1, wherein the composition lacks a buffer component (a) in which a weak base and conjugate acid are present in a ratio of ≤1:10; (b) having a pKa of between 5.3-7.3; and (c) that can detectably prevent a change in pH of the composition of more than 2% when 0.1 moles of HCl or 0.1 moles of NaOH are added to 1 L of the composition at a pH of 6.3.

3. The method of claim 1, wherein the composition comprises a carrier and the carrier is composed of at least about 50 w/v. % water.

4. The method of claim 1, wherein the ketorolac tromethamine is present in an amount of between 0.1-0.5 w/v. %.

5. The method of claim 4, wherein the phenylephrine hydrochloride is present in an amount of between 0.1-2% w/v. %.

6. The method of claim 5, wherein the ketorolac tromethamine is present in an amount of between about 0.3 w/v. % and about 0.5 w/v. % and the phenylephrine hydrochloride is present in an amount of between about 1 w/v. % and about 1.5 w/v. %.

7. The method of claim 5, wherein at least about 98% of the starting amount of ketorolac tromethamine and at least 98% of the starting amount phenylephrine hydrochloride remain present in the composition after a storage period of at least 3 months at about 25° C.+/−2° C., at about 25° C. and about 60% relative humidity, at about 40° C. and about 75% relative humidity, or when stored under any combination of such conditions.

8. The method of claim 7, wherein the composition comprises less than about 0.4% 1-(3-hydroxyphenyl)-2-(methylamino) ethan-1-one hydrochloride, less than 0.4% 5-benzoyl-2,3-dihydro-1H-pyrrolizine-1H-one, or the composition comprises less than about 0.4% of the combination of 1-(3-hydroxyphenyl)-2-(methylamino) ethan-1-one hydrochloride and 5-benzoyl-2,3-dihydro-1H-pyrrolizine-1H-one, after a storage period of at least 3 months at about 25° C.+/−2° C., at about 25° C. and about 60% relative humidity, at about 40° C. and about 75% relative humidity, or when stored under any combination of such conditions.

9. The method of claim 5, wherein the composition is provided in aqueous form for combination with an ocular irrigation solution prior to administration of the combined composition to an eye of subjects, wherein the irrigation solution makes up more than about 99% of the volume of the combined composition formed by the combination of the composition and the irrigation solution.

10. A method of promoting dilation of a pupil comprising administering a therapeutically effective amount of an ophthalmologically suitable composition comprising therapeutically effective amounts of each of ketorolac tromethamine and phenylephrine hydrochloride, wherein the composition (1) lacks any combination of a weak base and its conjugate acid that effectively acts as a buffer in the composition at a pH of about 6.3, (2) maintains a pH of between 5.5-7 for a period of at least one month under storage conditions, and (3) retains at least 99.5% pure ketorolac tromethamine and at least 99.5% pure phenylephrine hydrochloride when the composition is stored under storage conditions for at least one month, wherein the storage conditions comprise storage at about 25° C.+/−2° C., at about 25° C. and about 60% relative humidity, storage at about 40° C. and about 75% relative humidity, or storage under any combination of such conditions.

11. A method of promoting dilation of a pupil comprising administering a therapeutically effective amount of an ophthalmologically suitable composition comprising therapeutically effective amounts of each of ketorolac tromethamine and phenylephrine hydrochloride, wherein the composition (1) lacks any combination of a weak base and its conjugate acid that effectively acts as a buffer in the composition at a pH of about 6.3 (2) maintains a pH of between about 6-7 when stored under storage conditions for a period of at least about one month, and (3) retains at least 97% of the one or more ketorolac compounds and at least 97% of the one or more phenylephrine compounds when the composition is stored under storage conditions for at least one month, wherein the storage conditions comprise storage at about 25° C.+/−2° C., at about 25° C. and about 60% relative humidity, storage at about 40° C. and about 75% relative humidity, or storage under any combination of such conditions, and wherein the pH of the composition upon administration is between about 6.2 and about 6.4.

* * * * *